(12) United States Patent
Breitenkamp et al.

(10) Patent No.: US 7,638,558 B2
(45) Date of Patent: Dec. 29, 2009

(54) POLYMERIC MICELLES FOR DRUG DELIVERY

(75) Inventors: Kurt Breitenkamp, Northampton, MA (US); Kevin N. Sill, Tampa, FL (US); Habib Skaff, Tampa, FL (US); Rebecca Breitenkamp, Northampton, MA (US)

(73) Assignee: Intezyne Technologies, Inc., Tampa, FL (US)

( * ) Notice: Subject to any disclaimer, the term of this patent is extended or adjusted under 35 U.S.C. 154(b) by 719 days.

(21) Appl. No.: 11/396,872

(22) Filed: Apr. 3, 2006

(65) Prior Publication Data

US 2006/0240092 A1 Oct. 26, 2006

Related U.S. Application Data

(60) Provisional application No. 60/667,260, filed on Apr. 1, 2005, provisional application No. 60/741,780, filed on Dec. 1, 2005.

(51) Int. Cl.
*A61K 47/00* (2006.01)

(52) U.S. Cl. ............... 514/772.1; 514/772; 514/72.3; 514/773

(58) Field of Classification Search ............ None
See application file for complete search history.

(56) References Cited

U.S. PATENT DOCUMENTS

| | | | |
|---|---|---|---|
| 5,449,513 A | 9/1995 | Kataoka | |
| 5,510,103 A | 4/1996 | Kataoka | |
| 6,881,484 B2 | 4/2005 | Kataoka | |
| 7,223,419 B2 | 5/2007 | Yokoyama et al. | |
| 7,311,901 B2 * | 12/2007 | Seo et al. | 424/78.27 |
| 2003/0175313 A1 | 9/2003 | Garrec et al. | |
| 2004/0048782 A1 | 3/2004 | Flamel | |
| 2004/0126900 A1 | 7/2004 | Barry et al. | |
| 2004/0138095 A1 | 7/2004 | Soula et al. | |
| 2005/0119193 A1 | 6/2005 | Motoyama | |
| 2005/0214375 A1 | 9/2005 | Nakanishi et al. | |
| 2005/0249786 A1 | 11/2005 | Goldshtein et al. | |
| 2006/0142506 A1 | 6/2006 | Breitenkamp et al. | |
| 2006/0172914 A1 | 8/2006 | Breitenkamp et al. | |
| 2006/0269613 A1 | 11/2006 | Ogawa et al. | |

(Continued)

FOREIGN PATENT DOCUMENTS

EP 1230934 8/2002

(Continued)

OTHER PUBLICATIONS

Nishiyama et al., "Preparation and Characterization of Self-Assembled Polymer-Metal Complex Micelle from *cis*-Dichlorodiammineplatinum(II) and Poly(ethylene glycol)-Poly(α,β-aspartic acid) Block Copolymer in an Aqueous Medium," Langmuir, 15:377-383 (1999).

(Continued)

*Primary Examiner*—Eric E. Silverman
(74) *Attorney, Agent, or Firm*—Choate, Hall & Stewart LLP; Andrea L. C. Robidoux, Esq.

(57) ABSTRACT

The present invention relates to the field of polymer chemistry and more particularly to multiblock copolymers and micelles comprising the same.

14 Claims, 14 Drawing Sheets

U.S. PATENT DOCUMENTS

2007/0059271 A1    3/2007    Kataoka et al.

FOREIGN PATENT DOCUMENTS

WO    2006054288    5/2006

OTHER PUBLICATIONS

Y. Kakizawa: "Glutathione-sensitive stabilization of block copolymer micelles composed of antisense DNA and thiolated poly(ethylene glycol)-block-poly(L-lysine): A potential carrier for systemic delivery of antisense DNA" Biomacromolecules, vol. 2, 2001, pp. 491-497.

Nishiyama, et al. "Preparation and characterization of self-assembled polymer-metal complex micelle from cis-dichlorodiammineplatinum(II) and poly(ethylene glycol)-poly(alpha, beta-aspartic acid) block copolymer in an aqueous medium" Langmuir & Langmuir ACS, vol. 15, No. 2, 1999, pp. 377-383.

Y. Kakizawa: "Environment-sensitive stabilization of core-shell structured polyion complex micelle by reversible cross-linking of the core through disulfide bond" J. Am. Chem. Soc., vol. 121, 1999, pp. 11247-11248.

Yokoyama, et al.: "Preparation of Micelle-Forming Polymer-Drug Conjugates" Bioconjugate Chem. 1992, 3, 295-301.

Li, et. al.: "RAFT Synthesis of a Thermally Responsive ABC Triblock Copolymer Incorporating N-Acryloxysuccinimide for Facile in Situ Formation of Shell Cross-Linked Micelles in Aqueous Media" Macromolecules 2006, 39, 81-89.

Pilon, et al.: "Synthesis and Characterization of Shell Cross-Linked Micelles with Hydroxy-Functional Coronas: A Pragmatic Alternative to Dendrimers?" Langmuir 2005, 21, 3808-3813.

Liu, et al.: "Synthesis of Shell Cross-Linked Micelles with pH-Responsive Cores Using ABC Triblock Copolymers" Macromolecules 2002, 35, 6121-6131.

Butun, et al.: "Synthesis of Shell Cross-Linked Micelles at High Solids in Aqueous Media" Macromolecules, vol. 33, No. 1 Jan. 11, 2000.

Deming: "Methodologies for preparation of synthetic block copolypeptides: materials with future promise in drug delivery" Advanced Drug Delivery Reviews, vol. 54, 2002, 1145-1155.

Ferrari: "Cancer Nanotechnology: Opportunities and Challenges" Nature Reviews | Cancer, vol. 5, Mar. 2005, pp. 161.

Cammas-Marion, et al.: "Functional and site-specific macromolecular micelles as high potential drug carriers" Colloids and Surfaces B: Biointerfaces 16 (1999) 207-215.

Bronich, et al.: "Polymer Micelle with Cross-Linked Ionic Core" J. Am. Chem. Soc., published on the web.

Fukushima, et al.: "PEGylated Polyplex Micelles from Triblock Catiomers with Spatially Ordered Layering of Condensed pDNA and Buffering Units for Enhanced Intracellular Gene Delivery" J. Am. Chem. Soc., published on the web.

Rosler, et al.: "Advanced drug delivery devices via self-assembly of amphiphilic block copolymers" Advanced Drug Delivery Reviews 53 (2001) 95-108.

Adams, et al.: "Amphiphilic Block Copolymers for Drug Delivery" Journal of Pharmaceutical Sciences, vol. 92, No. 7, Jul. 2003.

Thunemann, et al.: "Two-Compartment Micellar Assemblies Obtained via Aqueous Self-Organization of Synthetic Polymer Building Blocks" Langmuir, Published on Web Feb. 16, 2006.

Li, et. al.: "Synthesis of Reversible Shell Cross-Linked Micelles for Controlled Release of Bioactive Agents" Macromoleucles, 2006, 39, 2726-2728.

Pitarresi, et. al.: "Composite Nanoparticles Based on Hyaluronic Acid Chemically Cross-Linked with a,b-Polyaspartylhydrazide" Biomacromolecules 2007, 8, 1890-1898.

Kim, et. al.: "Core-stabilized Polymeric Micelle as Potential Drug Carrier: Increased Solubilization of Taxol" Polym. Adv. Technol. 10, 647-654 (1999).

Iijima, et. al.: "Core-Polymerized Reactive Micelles from Heterotelechelic Amphiphilic Block Copolymers" Macromolecules 1999, 32, 1140-1146.

Lokitz, et. al.: Aqueous RAFT Synthesis of Micelle-Forming Amphiphilic Block Copolymers Containing N-Acryloylvaline. Dual Mode, Temperature/pH Responsiveness, and "Locking" of Micelle Structure through Interpolyelectrolyte Complexation Macromolecules 2007, 40, 6473-6480.

Yuan, et. al.: "Characterization of stable lysozyme-entrapped polyion complex (PIC) micelles with crosslinked core by glutaraldehyde" Polymer 46 (2005) 7749-7758.

Read, et. al.: "Recent advances in shell cross-linked micelles" Chem. Commun., 2007, 3021-3035.

Bae, et. al: "Oil-Encapsulating PEO-PPO-PEO/PEG Shell Cross-Linked Nanocapsules for Target-Specific Delivery of Paclitaxel" Biomacromolecules 2007, 8, 650-656.

Jiang, et. al.: "Polymer Micelles Stabilization on Demand through Reversible Photo-Cross-Linking" Macromolecules 2007, 40, 790-792.

Joralemon, et. al.: "Synthesis, Characterization, and Bioavailability of Mannosylated Shell Cross-Linked Nanoparticles" Biomacromolecules 2004, 5, 903-913.

Zhang, et. al.: "Shell Cross-Linked Nanoparticles Containing Hydrolytically Degradable, Crystalline Core Domains" J. Am. Chem. Soc. 2000, 122, 3642-3651.

Thurmond, et. al.: "Shell Cross-Linked Knedels: A Synthetic Study of the Factors Affecting the Dimensions and Properties of Amphiphilic Core-Shell Nanospheres" J. Am. Chem. Soc. 1997, 119, 6656-6665.

International Search Report for PCT/US2006/012382.

* cited by examiner

POLYMERIC MICELLES FOR DRUG DELIVERY

CROSS-REFERENCE TO RELATED APPLICATIONS

This application claims priority to U.S. provisional applications Ser. No. 60/667,260, filed Apr. 1, 2005, and 60/741,780, filed Dec. 1, 2005, the entirety of each of which is hereby incorporated herein by reference.

FIELD OF THE INVENTION

The present invention relates to the field of polymer chemistry and more particularly to micelles and uses thereof.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs in response to the physiological environment encountered in diseased tissues, such as solid tumors.

DETAILED DESCRIPTION OF CERTAIN EMBODIMENTS OF THE INVENTION

Figure 1:
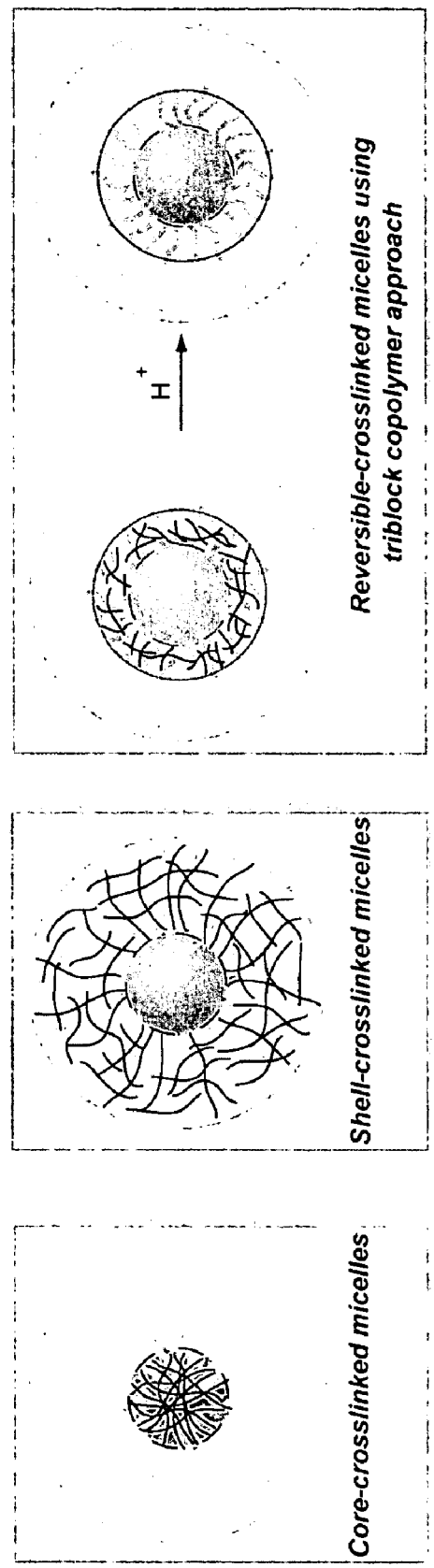
FIG. 1 depicts a representation of a core crosslinked micelle, a shell crosslinked micelle, and an outer-core crosslinked micelle of the present invention.
Figure 2:
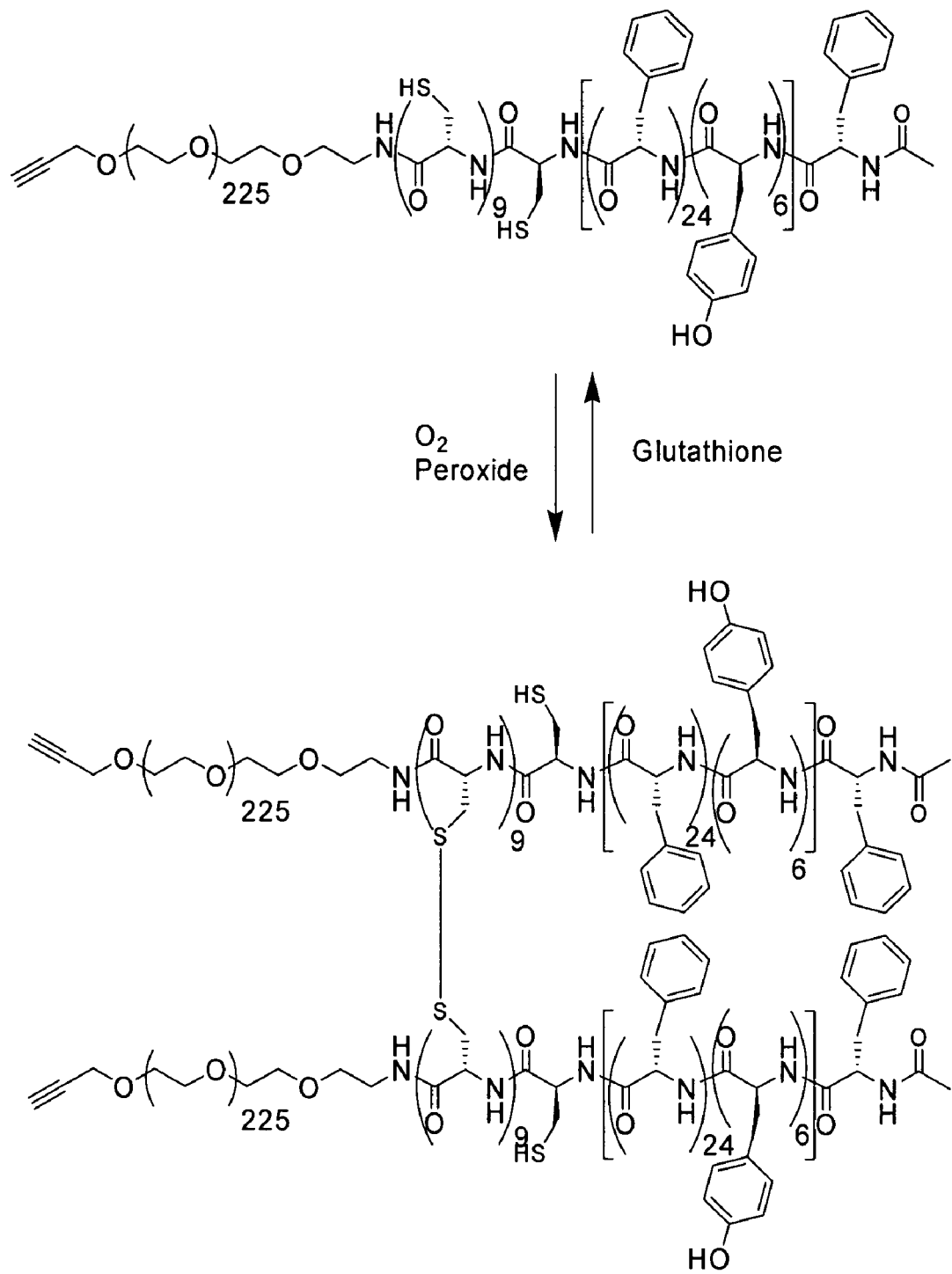
FIG. 2 depicts an exemplary disulfide crosslinking reaction.
Figure 3:
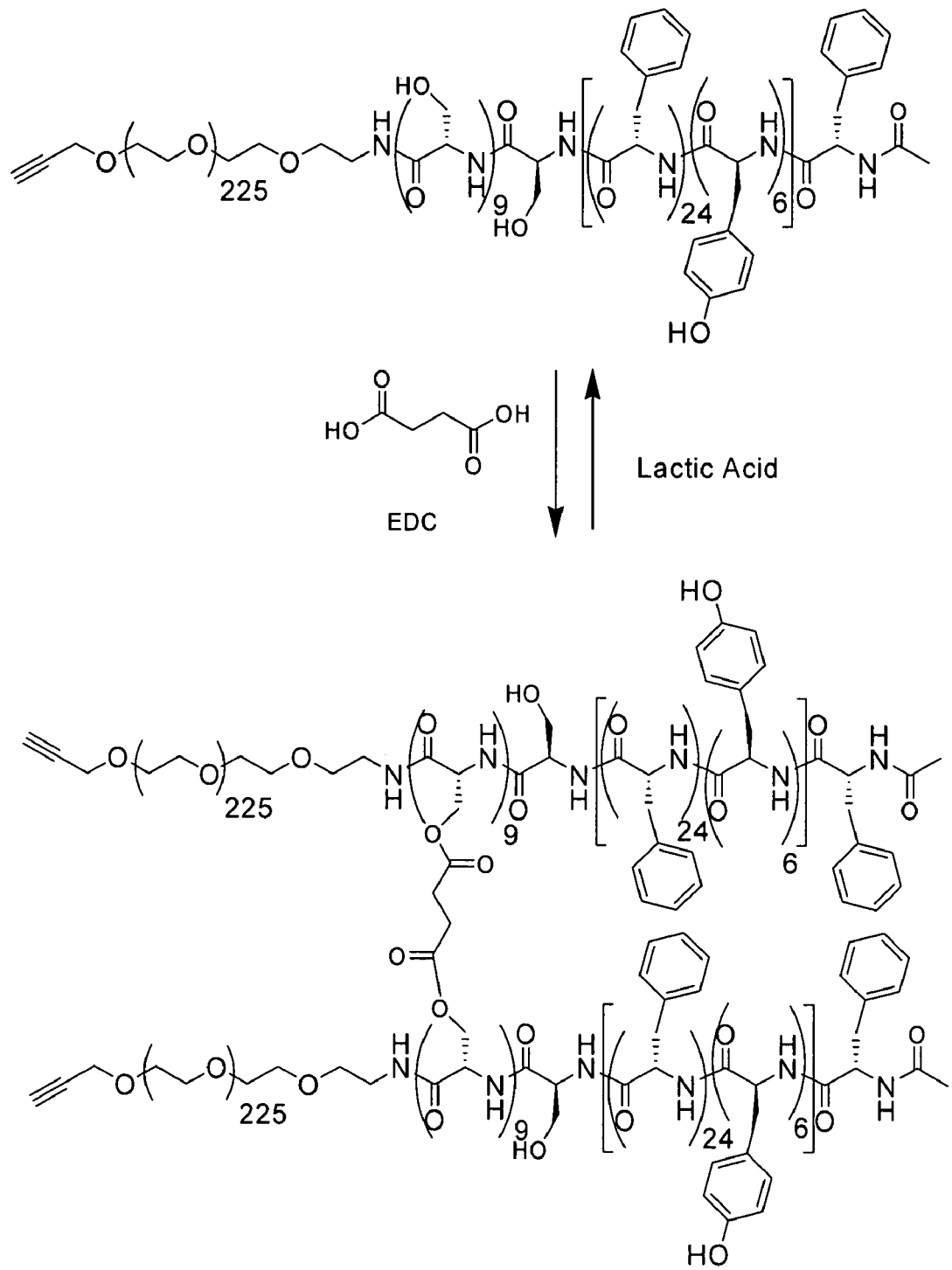
FIG. 3 depicts an exemplary ester crosslinking reaction.
Figure 4:
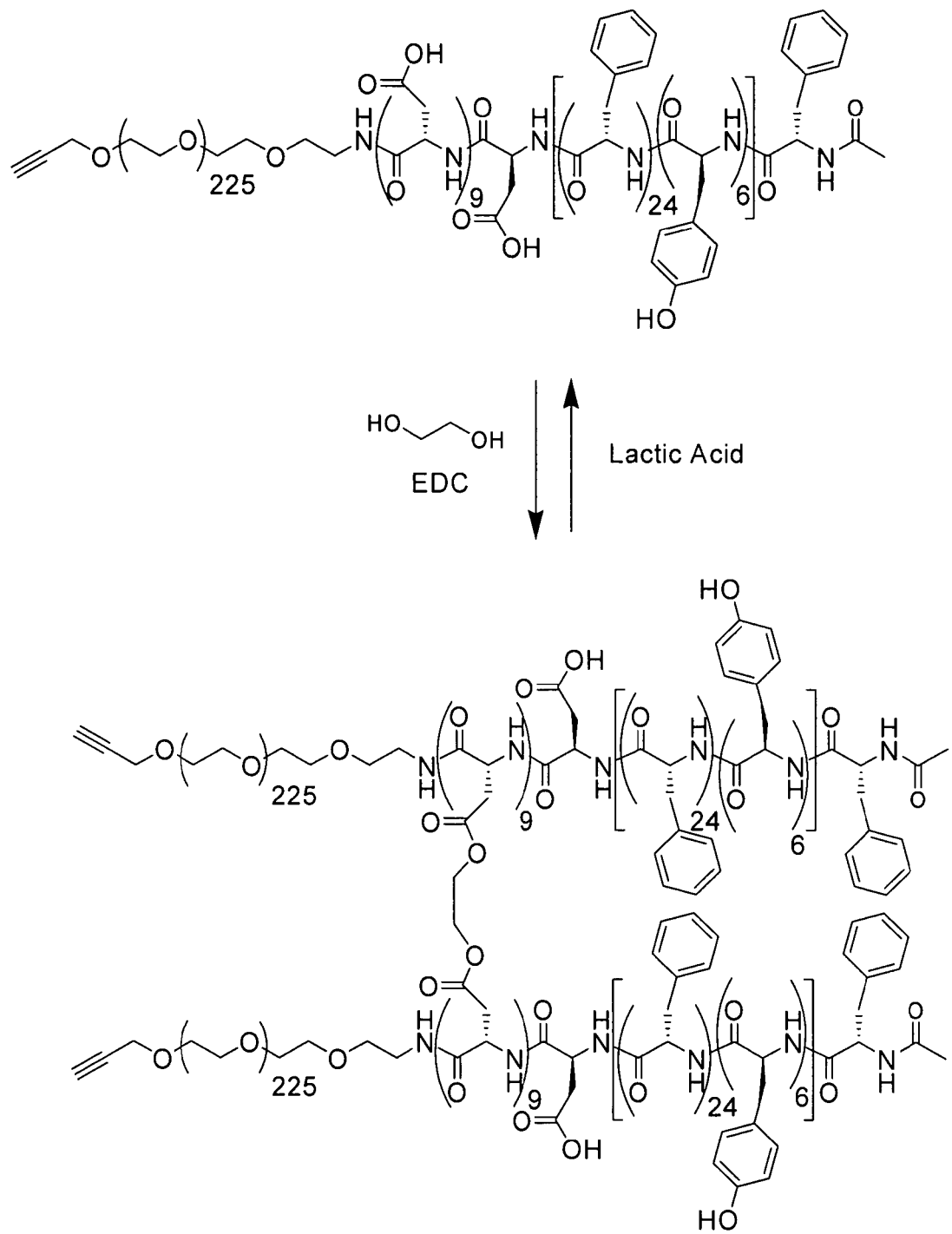
FIG. 4 depicts an exemplary ester crosslinking reaction.
Figure 5:
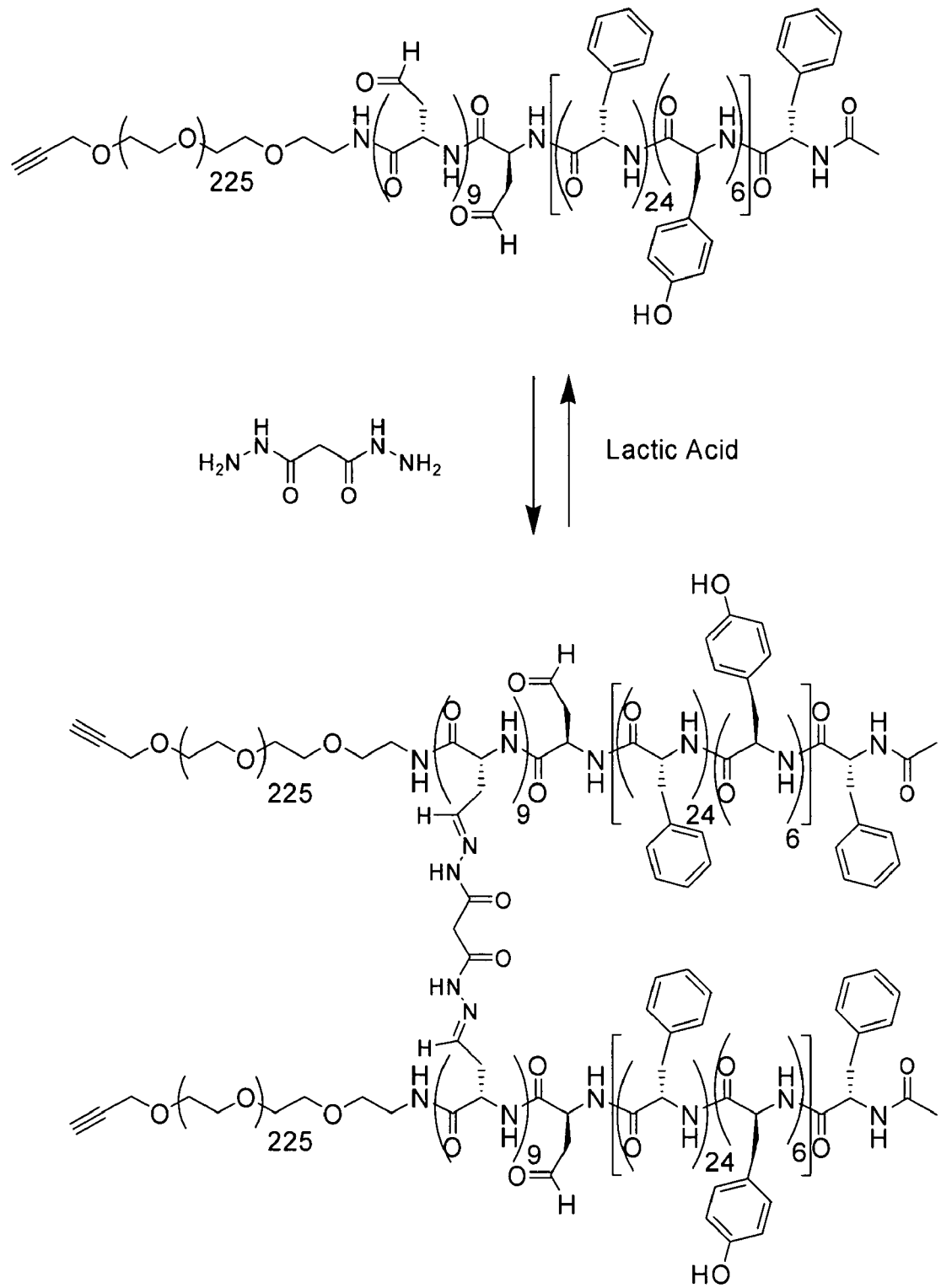
FIG. 5 depicts an exemplary hydrazone crosslinking reaction.
Figure 6:
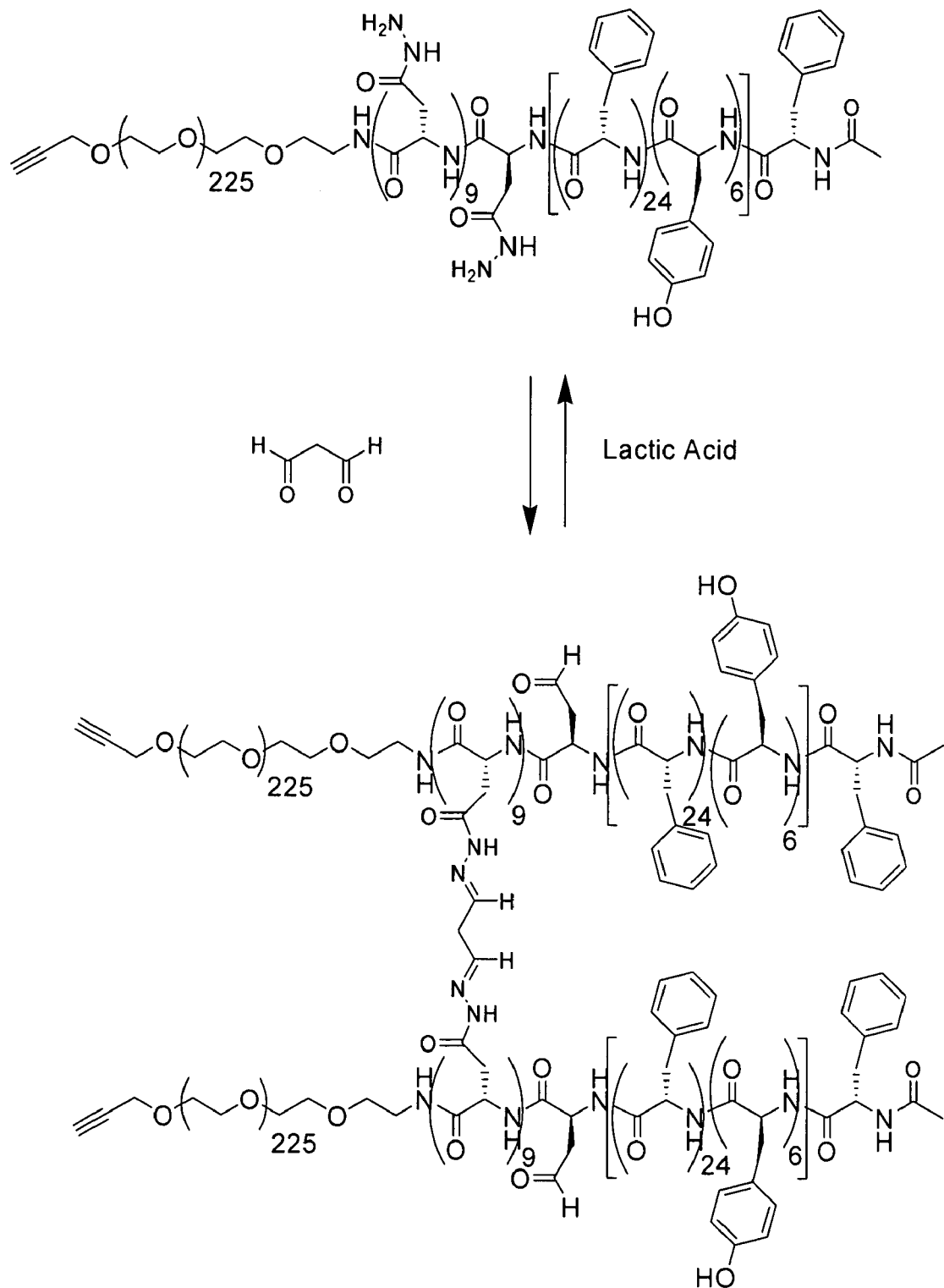
FIG. 6 depicts an exemplary hydrazone crosslinking reaction.
Figure 7:
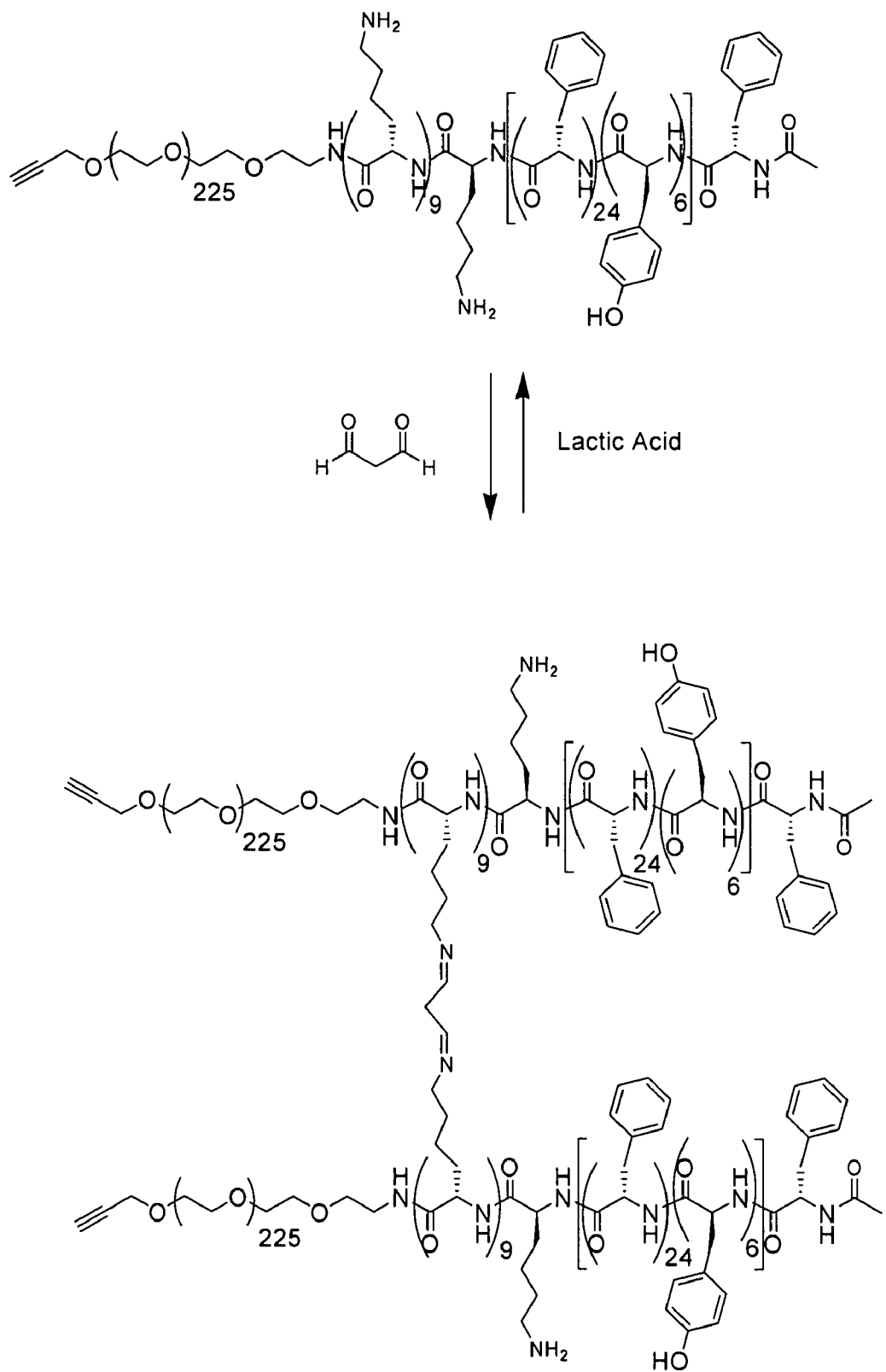
FIG. 7 depicts an exemplary Schiff base crosslinking reaction.
Figure 8:
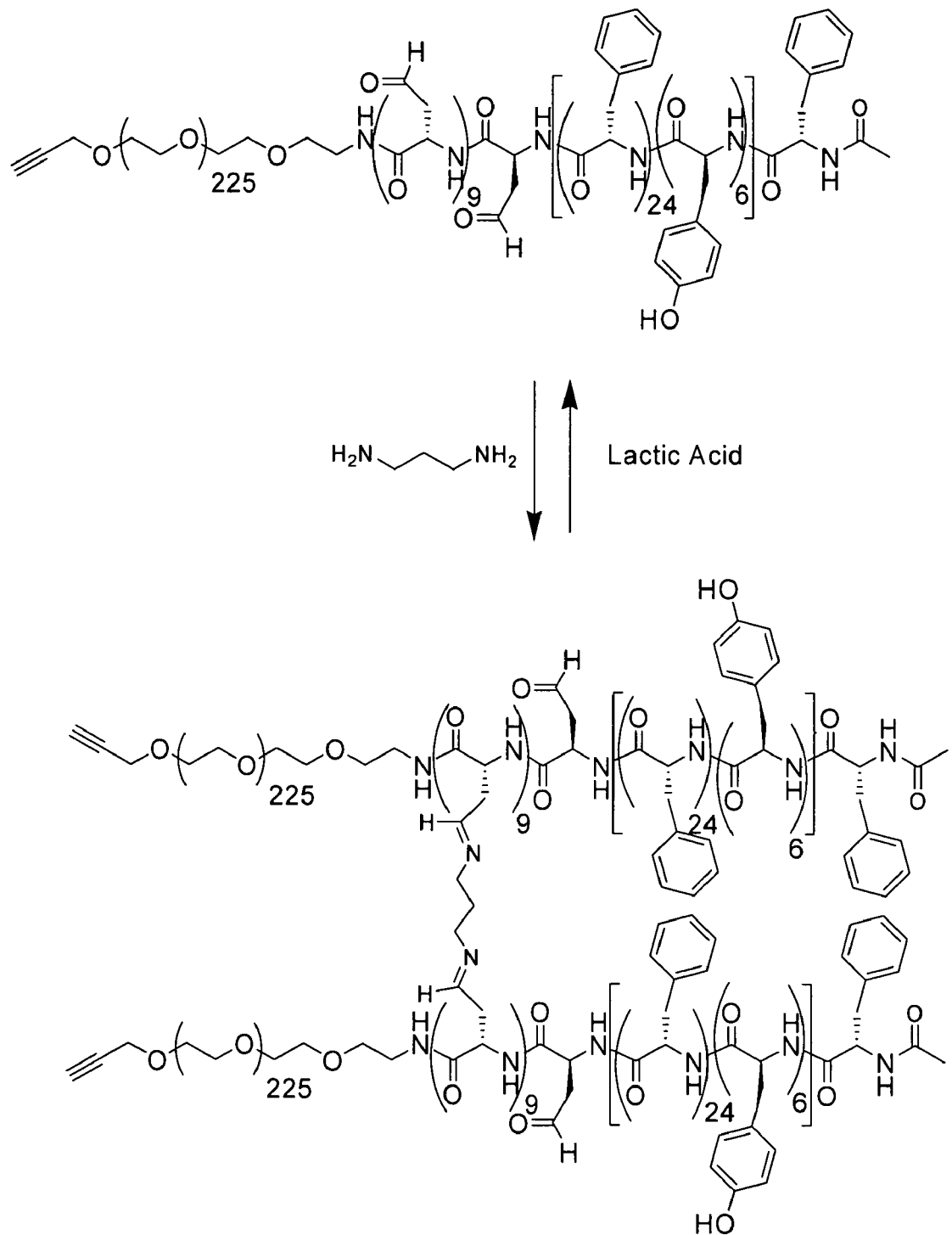
FIG. 8 depicts an exemplary Schiff base crosslinking reaction.
Figure 9:
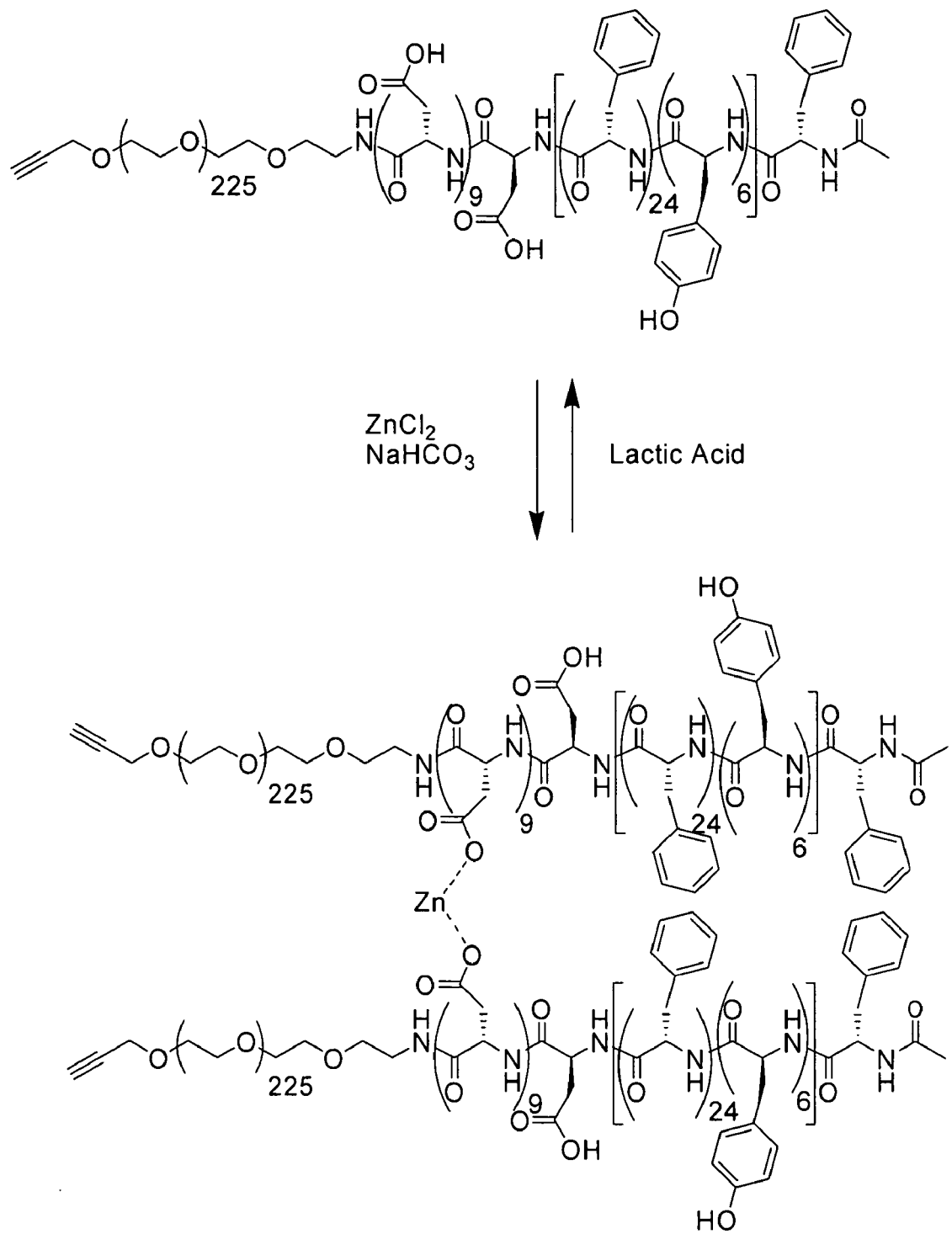
FIG. 9 depicts an exemplary zinc crosslinking reaction.
Figure 10:
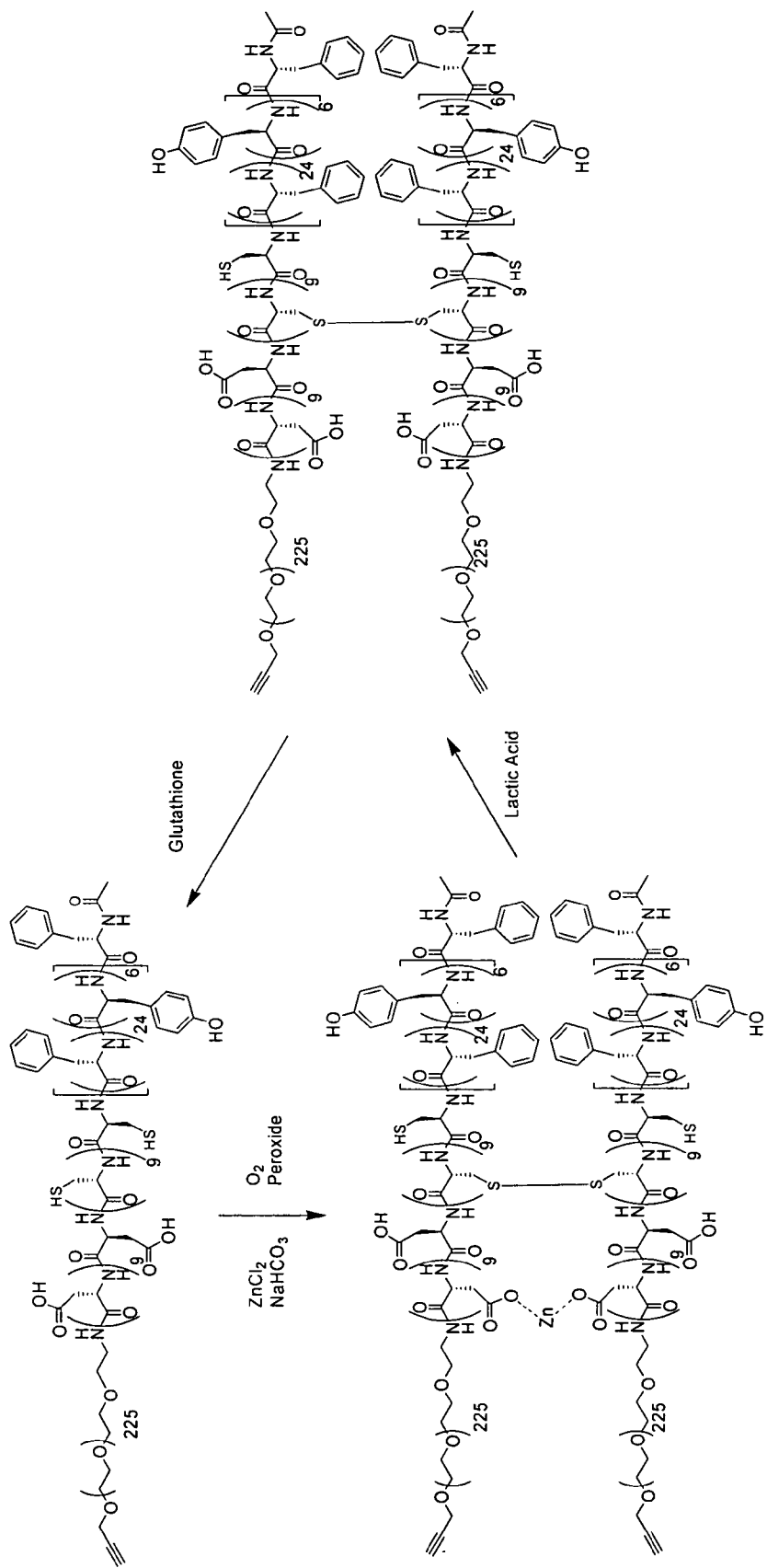
FIG. 10 depicts an exemplary dual crosslinking reaction.

1. General Description:

Bionanotechnology is a broad, multi-disciplinary field encompassing the biological, chemical, physical, and engineering sciences and is dedicated to the design and manipulation of biomaterials on the nanometer size scale. These "nanodevices" offer the potential to become highly advanced, multi-functional tools capable of detection, diagnosis, and personalized treatment of diseases, such as cancer. In the case of drug delivery, nanoscopic therapeutic carriers, or "nanovectors," are a potentially promising method to selectively deliver chemotherapeutic agents to cancerous and other diseased tissue. The advantages of nano-sized encapsulation devices are numerous. For example, when compared to single molecule drugs or diagnostic agents, "nanovectors" can transport much larger quantities of such agents. Nanoscopic drug delivery systems are generally more apt to elude biological barriers, resulting in reduced inactivation or excretion of the encapsulated therapeutic. Multi-functionality is a common feature of nanovectors whereby multiple drugs, diagnostic agents, and targeting groups can be packaged into a single system. The bottom-up design of nanoscopic drug delivery systems often involves the precise self assembly of single molecules or polymeric units to create complex, multi-functional devices.

Polymer micelles are one type of nanovector formed by the aqueous assembly of block copolymers that are polymer chains containing both hydrophilic and hydrophobic portions. These structures often exist as spherical particles with a core-shell morphology and sub-micron diameter. Their size and structural uniformity impart a striking resemblance to virus particles, which are Nature's version of the perfect delivery system and are capable of highly efficient delivery to cells and tissue. It is believed that the nanoscopic size of viruses (approximately 20 to 400 nanometers in diameter) contributes to their ability to elude the body's natural defense mechanisms while proteins on the virus surface enable highly selective targeting and infection of specific cells. The design of nanovectors, such as block copolymer micelles, that effectively mimic the selectivity and evasiveness of viral particles remains a major goal of drug delivery research. Polymer micelles present a viable alternative due to the inherent modularity of block copolymers, which offer considerable tuning of the micelle size and surface functionality. In certain embodiments, micelles of the present invention, as described in detail infra, are about 20 to about 200 nanometers in diameter. In other embodiments, micelles of the present invention, as described in detail infra, are about 20 to about 250 nanometers in diameter.

One advantage of the polymer micelle modularity is the ability to tune the core and shell components. This is particularly useful for drug delivery because the core of the assembly can serve as a reservoir for a variety of therapeutic agents while the hydrophilic shell imparts solubility and stability to the aqueous assemblies. From a pharmacokinetic viewpoint, the distribution of drug-loaded micelles is largely determined by the size and surface chemistry of the micelle and not by the drug itself. Thus, polymer micelles possessing a hydrophobic core are utilized for the encapsulation of potent, small molecule drugs that were previously shelved due to poor aqueous solubility. The isolation of hydrophobic chemotherapeutics in the micelle core has also provided new strategies to overcome multi-drug resistance (MDR) mechanisms in cancer cells. Polymer micelles with cationically charged, core-forming blocks are used to encapsulate biomolecules such as plasmid DNA and siRNA. Therapeutics of this type are normally susceptible to rapid in vivo degradation, and their encapsulation in polymer micelles improves their biodistribution profiles thus leading to future clinical successes.

One biological barrier to any drug delivery system and another issue which cell-responsive nanovectors addresses is the non-specific uptake by the reticuloendothelial system. The RES consists of a host of cells which are designed to remove cellular debris and foreign particles from the bloodstream. Like viruses, synthetic nanovectors are more apt at escaping RES detection by the nature of their size. In addition, the covalent attachment of poly(ethylene glycol) is a commonly used method to reduce opsonization and non-specific RES uptake of small molecule, protein, and nanoparticulate drug carriers. See Harris, J. M.; Martin, N. E.; Modi, M. *Clin. Pharmacokin.* 2001, 40, 539-551; Bhadra, D.; Bhadra, S.; Jain, P.; Jain, N. K. *Pharmazie* 2002, 57, 5-29; Shenoy, D. B.; Amiji, M. A. *Int. J. Pharm.* 2005, 293, 261-270; and Torchilin, V. *Adv. Drug. Del. Rev.* 2002, 54, 235-252.

PEG has become a standard choice for the hydrophilic, corona-forming segment of block copolymer micelles, and numerous studies have confirmed its ability to reduce RES uptake of micellar delivery systems. See Kwon, G.; Suwa, S.; Yokoyama, M.; Okano, T.; Sakurai, Y.; Kataoka, K. *J. Cont. Rel.* 1994, 29, 17-23; Caliceti, P.; Veronese, F. M. *Adv. Drug Del. Rev.* 2003, 55, 1261-1277; Ichikawa, K.; Hikita, T.; Maeda, N.; Takeuchi, Y.; Namba, Y.; Oku, N. *Bio. Pharm. Bull.* 2004, 27, and 443-444. The ability to tailor PEG chain lengths offers numerous advantages in drug carrier design since studies have shown that circulation times and RES uptake are influenced by the length of the PEG block. In general, longer PEG chains lead to longer circulation times and enhanced stealth properties. In a systematic study of PEG-b-poly(lactic-co-glycolic acid) (PLGA) micelles with PEG molecular weights ranging from 5,000-20,000 Da, Langer and coworkers found that micelles coated with 20,000 Da PEG chains were the least susceptible to liver uptake. After 5 hours of circulation, less than 30% of the micelles had accumulated in the liver. See Gref, R.; Minamitake, Y.; Peracchia, M. T.; Trubetskoy, V.; Torchilin, V.; Langer, R. *Science* 1994, 263, 1600-1603.

While PEGylation of nanovectors is an effective method to reduce RES uptake and extend in vivo circulation lifetime, other challenges exist which limit the ultimate effectiveness of colloidal drug carriers. One such barrier relates to their self assembly and subsequent in vivo stability. Self assembly represents a convenient, bottom-up approach to nanovector design. The hydrophobic forces that drive the aqueous assembly of colloidal drug carriers, such as polymer micelles and liposomes, are relatively weak, and these assembled structures dissociate below a finite concentration known as the critical micelle concentration ("CMC"). The CMC value of these systems is of great importance in clinical applications since drug-loaded colloidal carriers are diluted in the bloodstream following administration and rapidly reach concentrations below the CMC (μM or less) leading to micelle dissociation. In addition, non-specific interactions with surfactant-like components in the blood (e.g. proteins, lipids, etc.) also act to destabilize drug-loaded micelles. See Savić, R.; Azzam, T.; Eisenberg, A.; Maysinger, D. *Langmuir* 2006, ASAP article. These events often lead to premature drug release outside the targeted area, rendering the drug carrier and cell-targeting strategies ineffective.

Despite the large volume of work on micellar drug carriers, little effort has focused on improving their in vivo stability to dilution. In most cases, amphiphilic block copolymers lack the functionality necessary for post-assembly crosslinking strategies. Wooley and coworkers have addressed this issue by crosslinking the poly(acrylic acid) corona of the polymer micelles, forming shell-crosslinked nanoparticles. See Thurmond, K. B.; Huang, H. Y.; Clark, C. G.; Kowalewski, T.; Wooley, K. L. *Coll. Surf. B.* 1999, 16, 45-54. Covalent crosslinking produces nanoparticles with improved stability and offers the additional benefit of enhanced therapeutic payload since the core-forming block is chemically removed after crosslinking. See Zhang, Q.; Remsen, E. E.; Wooley, K. L. *J. Am. Chem. Soc.* 2000, 122, 3642-3651.

In a separate approach, Kataoka and coworkers have developed methods to reversibly crosslink the core of diblock polymer micelles to improve stability. For example, the chemotherapy drug cisplatin was encapsulated using PEG-b-poly(aspartic acid) copolymers, forming reversible chemical bonds in the micelle core. See Nishiyama, N.; Yokoyama, M.; Aoyagi, T.; Okano, T.; Sakurai, Y.; Kataoka, K. *Langmuir* 1999, 15, 377-383. The micelles were stable to dilution as determined by dynamic light scattering studies, and the core-crosslinking was reversible in the presence of chloride ions, resulting in dissociation of the polymer micelles and release of cisplatin. However, in vivo studies using tumor-bearing mice showed remarkably fast decay of the cisplatin-loaded micelles, which resulted in accumulation of the drug in the liver and spleen. See Nishiyama, N.; Kato, Y.; Sugiyama, Y.; Kataoka, K. *Pharm. Res.* 2001, 18, 1035-1041. Kataoka's group has also reported alternative core crosslinking strategies that utilize disulfide chemistry. In this case, cysteine units were randomly incorporated into the lysine portion of PEG-b-poly(L-lysine) copolymers and used for encapsulation of antisense RNA. See Kakizawa, Y.; Harada, A.; Kataoka, K. *J. Am. Chem. Soc.* 1999, 121, 11247-11248; and Kakizawa, Y.; Harada, A.; Kataoka, K. *Biomacromolecules* 2001, 2, 491-

497. The cysteine side chains were subsequently oxidized in the core to form disulfide crosslinked, RNA-loaded micelles. These micelles were shown to selectively dissociate in the presence of glutathione (GSH), a reducing agent found in appreciable quantities in the cell cytoplasm, offering an effective method for intracellular delivery of the therapeutic. Other core crosslinking techniques have been devised that utilize polymer end-groups, such as methacrylate and olefinic functionality, which are crosslinked by free radicals. See Iijima, M.; Nagasaki, Y.; Okada, T.; Kato, M.; Kataoka, K. *Macromolecules* 1999, 32, 1140-1146; and Tian, L.; Yam, L.; Wang, J. Z.; Tat, H.; Uhrich, K. E. *J. Mat. Chem.* 2004, 14, 2317-2324. One notable disadvantage of the core crosslinking approach is the inherent reduction of free-volume in the micelle core, which ultimately limits drug loading in the micelle.

Armes and coworkers have used covalent chemistries to crosslink the outer core of micelles made from poly[(ethylene oxide)-block-2-(dimethylamino)ethyl methacrylate-block-2-(diethylamino) methacrylate] copolymers. The addition of the bifunctional crosslinker, 1,2-bis(2-iodoethoxy)ethane, was shown to effectively crosslink the 2-(dimethylamino) ethyl methacrylate block, forming irreversible quaternary ammonium crosslinks. See Liu, S.; Weaver, J. V. M.; Tang, Y.; Billingham, N. C.; Armes, S. P. *Macromolecules,* 2002, 35, 6121-6131. McCormick and coworkers have synthesized poly(ethylene oxide)-block-[(N,N-dimethylacrylaride)-stat-(N-acryloxysuccinimide)]-block-(N-isopropylacrylamide) copolymers where the N-acryloxysuccinimide units are reacted with cystamine to crosslink the outer core of the micelle through reversible disulfide bonds. See Li, Y.; Lokitz, B. S.; Armes, S. P.; McCormick, C. L. *Macromolecules* 2006, ASAP article.

To address these pressing issues and develop improved disease-fighting systems, the present application describes the design and synthesis of "smart," drug-loaded polymer micelles which are stable to dilution in circulation, can more effectively accumulate in diseased cells, and dissociate in response to the range of environmental changes commonly found in diseased tissue and cells.

In certain embodiments, the present invention provides crosslinked micelles which effectively encapsulate hydrophobic or ionic therapeutic agents at pH 7.4 (blood) but dissociate and release the drug at targeted, acidic pH values ranging from 5.0 (endosomal pH) to 6.8 (extracellular tumor pH). In yet other embodiements, the pH value can be adjusted between 4.0 and 7.4. These pH-targeted nanovectors will dramatically improve the cancer-specific delivery of chemotherapeutic agents and minimize the harmful side effects commonly encountered with potent chemotherapy drugs. In addition, the utilization of chemistries which can be tailored to dissociate across a range of pH values make these drug-loaded micelles applicable in treating solid tumors and malignancies that have become drug resistant.

The pH-responsive block copolymers and polymer micelles described herein are designed with an emphasis on modularity and multi-functionality. Although the encapsulation and delivery of doxorubicin and camptothecin are exemplified, it is contemplated that the present invention also provides a technology platform whereby a multitude of nanovectors are designed and tailored by simple variations in poly(amino acid) type and length, crosslinking chemistries, and surface targeting functionalities. Examples include polymer micelles with tailored ionic blocks for siRNA and protein encapsulation, reversible metal crosslinking strategies which incorporate MRI contrast agents (e.g. iron and gadolinium derivatives), and the application of micelles with reactive surface functionality for attachment of drugs, permeation enhancers, and targeting groups.

According to one embodiment, the present invention provides a micelle comprising a multiblock copolymer which comprises a polymeric hydrophilic block, a crosslinked poly (amino acid block), and a poly(amino acid block), characterized in that said micelle has an inner core, a crosslinked outer core, and a hydrophilic shell. It will be appreciated that the polymeric hydrophilic block corresponds to the hydrophilic shell, the crosslinked poly(amino acid block) corresponds to the crosslinked outer core, and the poly(amino acid) block corresponds to the inner core. According to another aspect, the present invention provides a drug-loaded micelle comprising a multiblock copolymer which comprises a polymeric hydrophilic block, a crosslinked poly(amino acid block), and a poly(amino acid block), characterized in that said micelle has a drug-loaded inner core, a crosslinked outer core, and a hydrophilic shell.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "sequential polymerization", and variations thereof, refers to the method wherein, after a first monomer (e.g. NCA, lactam, or imide) is incorporated into the polymer, thus forming an amino acid "block", a second monomer (e.g. NCA, lactam, or imide) is added to the reaction to form a second amino acid block, which process may be continued in a similar fashion to introduce additional amino acid blocks into the resulting multi-block copolymers.

As used herein, the term "multiblock copolymer" refers to a polymer comprising one synthetic polymer portion and two or more poly(amino acid) portions. Such multi-block copolymers include those having the format W—X'—X", wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

As used herein, the term "triblock copolymer" refers to a polymer comprising one synthetic polymer portion and two poly(amino acid) portions.

As used herein, the term "tetrablock copolymer" refers to a polymer comprising one synthetic polymer portion and either two poly(amino acid) portions, wherein 1 poly(amino acid) portion is a mixed block or a polymer comprising one synthetic polymer portion and three poly(amino acid) portions.

As used herein, the term "inner core" as it applies to a micelle of the present invention refers to the center of the micelle formed by the second (i.e., terminal) poly(amino acid) block. In accordance with the present invention, the inner core is not crosslinked. By way of illustration, in a triblock polymer of the format W—X'—X", as described above, the inner core corresponds to the X" block. It is contemplated that the X" block can be a mixed block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W—X'—X", as described above, the outer core corresponds to the X' block. It is contemplated that the X' block can be a mixed block.

As used herein, the terms "drug-loaded" and "encapsulated", and derivatives thereof, are used interchangeably. In accordance with the present invention, a "drug-loaded" micelle refers to a micelle having a drug, or therapeutic agent, situated within the core of the micelle. This is also refered to as a drug, or therapeutic agent, being "encapsulated" within the micelle.

As used herein, the term "polymeric hydrophilic block" refers to a polymer that is not a poly(amino acid) and is hydrophilic in nature. Such hydrophilic polymers are well known in the art and include polyethyleneoxide (also referred to as polyethylene glycol or PEG), and derivatives thereof, poly(N-vinyl-2-pyrolidone), and derivatives therof, poly(N-isopropylacrylamide), and derivatives thereof, poly(hydroxyethyl acrylate), and derivatives thereof, poly(hydroxyethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit is in the L-configuration. Such poly(amino acids) include those having suitably protected functional groups. For example, amino acid monomers may have hydroxyl or amino moieties which are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In other embodiments, an amino acid block comprises one or more monomers such that the overall block is hydrophobic. In still other embodiments, amino acid blocks of the present invention include random amino acid blocks, ie blocks comprising a mixture of amino acid residues.

As used herein, the phrase "natural amino acid side-chain group" refers to the side-chain group of any of the 20 amino acids naturally occuring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to amino acids not included in the list of 20 amino acids naturally occuring in proteins, as described above. Such amino acids include the D-isomer of any of the 20 naturally occuring amino acids. Unnatural amino acids also include homoserine, ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is the compound that reacts with an alkylene oxide to afford a polyalkylene oxide block. In other embodiments, the polymerization initiator is the amine salt described herein.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^+$)— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR•; —(CH$_2$)$_{0-4}$S(O)$_2$R•; —(CH$_2$)$_{0-4}$S(O)$_2$OR°; —(CH$_2$)$_{0-4}$OS(O)$_2$R•; —S(O)$_2$NR°$_2$; —(CH$_2$)$_{0-4}$S(O)R•; —N(R°)S(O)$_2$NR°$_2$; —N(R°)S(O)$_2$R•; —N(OR°)R•; —C(NH)NR°$_2$; —P(O)$_2$R•; —P(O)R$_{12}$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{500}$, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

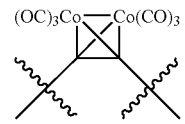

when depicted with the methylenes which bear it.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable monoprotected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —$CH_2CH_2O$—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

Other primary labels include those useful for positron emission tomography including molecules containing radioisotopes (e.g. $^{18}F$) or ligands with bound radioactive metals (e.g. $^{62}Cu$). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erytlrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4', 5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate", as used herein refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metalic or chemical coating, membranes (eg., nylon, polysulfone, silica), micro-beads (eg., latex, polystyrene, or other polymer), porous polymer matrices (eg., polyacrylamide gel, polysaccharide, polymethacrylate), macromolecular complexes (eg., protein, polysaccharide).

3. Description of Exemplary Embodiments:
   A. Multiblock Copolymers

As described generally above, one embodiment of the present invention provides a micelle comprising a multiblock copolymer which comprises a polymeric hydrophilic block, a crosslinked poly(amino acid block), and a poly(amino acid) block, characterized in that said micelle has an inner core, a crosslinked outer core, and a hydrophilic shell.

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the hydrophobic poly(amino acid) portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In addition, these multiblock polymers comprise a poly(amino acid) block which contains functionality suitable for crosslinking. It will be appreciated that this functionality is found on the corresponding amino acid side-chain.

Multiblock copolymers of the present invention contain poly(amino acid) blocks and a water-soluble polymer block. Poly(amino acid) (PAA) segments possess a wide range of functionality and are natural building blocks with inherent biocompatibility. In addition, PAA copolymers are hydrolytically stable and can tolerate most chemical transformation conditions yet can be enzymatically degradable.

In certain embodiments, the PEG block possesses a molecular weight of approx. 10,000 Da (225 repeat units) and contains at least one terminal amine hydrochloride salt used to initiate the synthesis of poly(amino acid) multi-block copolymers. Without wishing to be bound by theory, it is believed that this particular PEG chain length imparts adequate water-solubility to the micelles and provides relatively long in vivo circulation times.

In certain embodiments, the present invention provides a micelle comprising a multiblock copolymer of formula I:

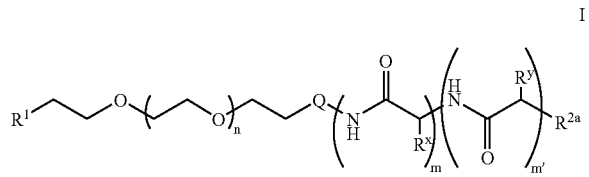

wherein:
   n is 10-2500;
   m is 1 to 1000;
   m' is 1 to 1000;
   $R^x$ is a natural or unnatural amino acid side-chain group that is capable of crosslinking;
   $R^y$ is a hydrophobic or ionic, natural or unnatural amino acid side-chain group;
   $R^1$ is -Z(CH$_2$CH$_2$Y)$_p$(CH$_2$)$_t$R$^3$, wherein:
      Z is —O—, —S—, —C≡C—, or —CH$_2$—;
      each Y is independently —O— or —S—;
      p is 0-10;
      t is 0-10; and
   $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the present invention provides compounds of formula I, as described above, wherein said compounds have a polydispersity index ("PDI") of about 1.0 to about 1.2. According to another embodiment, the present invention provides compounds of formula I, as described above, wherein said compound has a polydispersity index ("PDI") of about 1.03 to about 1.15. According to yet another embodiment, the present invention provides compounds of formula I, as described above, wherein said compound has a polydispersity index ("PDI") of about 1.10 to about 1.20. According to other embodiments, the present invention provides compounds of formula I having a PDI of less than about 1.10.

In certain embodiments, the present invention provides compounds of formula I, as described above, wherein n is about 225. In other embodiments, n is about 200 to about 300. In still other embodiments, n is about 200 to about 250. In still other embodiments, n is about 100 to about 150. In still other embodiments, n is about 400 to about 500. In other embodiments, n is about 10 to about 40. In other embodiments, n is about 40 to about 60. In still other embodiments, n is about 90 to about 150. In still other embodiments, n is about 200 to about 250. In other embodiments, n is about 300 to about 375. In still other embodiments, n is about 650 to about 750.

In certain embodiments, the m' group of formula I is about 5 to about 500. In certain embodiments, the m' group of formula I is about 10 to about 250. In other embodiments, m' is about 10 to about 50. According to yet another embodiment, m' is about 15 to about 40. In other embodiments, m' is about 20 to about 40. According to yet another embodiment, m' is about 50 to about 75. According to other embodiments, m and m' are independently about 10 to about 100. In certain embodiments, m' is 5-50. In other embodiments, m' is 5-25. In certain embodiments, m' is 5-50. In other embodiments, m' is 5-10. In other embodiments, m' is 10-20. In certain embodiments, m and m' add up to about 30 to about 60. In still other embodiments, m' is 1-20 repeat units and m' is 10-50 repeat units.

In certain embodiments, the $R^3$ moiety of the $R^1$ group of formula I is —N$_3$.

In other embodiments, the $R^3$ moiety of the $R^1$ group of formula I is —CN.

In still other embodiments, the $R^3$ moiety of the $R^1$ group of formula I is a mono-protected amine or a di-protected amine.

In certain embodiments, the $R^3$ moiety of the $R^1$ group of formula I is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, N$_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methylpropargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula I is an optionally substituted aryl group. Examples include optionally substituted phenyl and optionally substituted pyridyl. When said $R^3$ moiety is a substituted aryl group, suitable substituents on $R^3$ include CN, N$_3$, NO$_2$, —CH$_3$, —CH$_2$N$_3$, —CH=CH$_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embofiments, the $R^3$ moiety is an aryl group substituted with a suitably protected amino group. According to another aspect, the $R^3$ moiety is phenyl substituted with a suitably protected amino group.

In other embodiments, the $R^3$ moiety of the $R^1$ group of formula I is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula I is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula I is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula I is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiments, the $R^3$ moiety of the $R^1$ group of formula I is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—SCH$_3$, or —S—S(p-ethynylbenzyl). In other embodmients, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula I is a crown ether. Examples of such crown ethers include 12-crown-4, 15-crown-5, and 18-crown-6.

In still other embodiments, the $R^3$ moiety of the $R^1$ group of formula I is a detectable moiety. According to one aspect of the invention, the $R^3$ moiety of the $R^1$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343. In certain embodiments, the $R^3$ moiety of the $R^1$ group of formula I is a detectable moiety selected from:

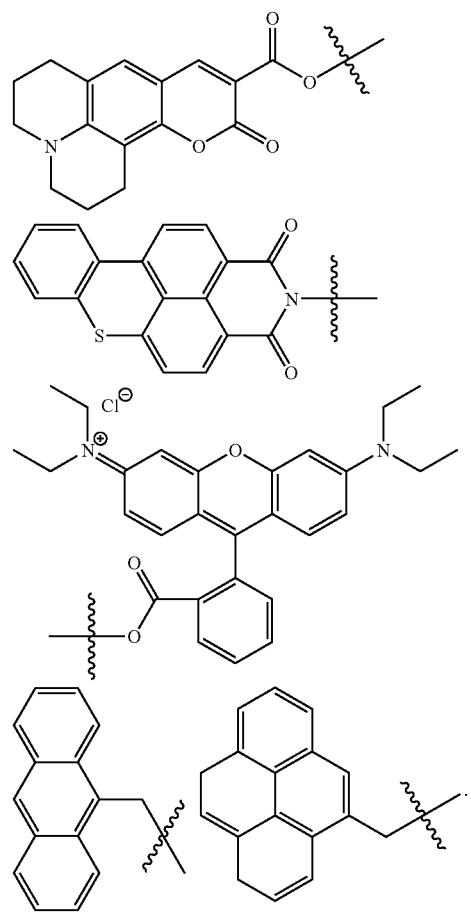

In certain embodiments, the $R^3$ moiety of the $R^1$ group of formula I is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula I having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula I to a macromolecule via Click chemistry. Yet another embodiment of the present invention provides a macromolecule conjugated to a compound of formula I via the $R^1$ group.

According to one embodiment, the $R^3$ moiety of the $R^1$ group of formula I is an azide-containing group. According to another embodiment, the $R^3$ moiety of the $R^1$ group of formula I is an alkyne-containing group. In certain embodiments, the $R^3$ moiety of the $R^1$ group of formula I has a terminal alkyne moiety. In other embodiments, $R^3$ moiety of the $R^1$ group of formula I is an alkyne moiety having an electron withdrawing group. Accordingly, in such embodiments, the $R^3$ moiety of the $R^1$ group of formula I is

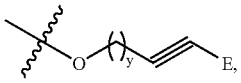

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula I is

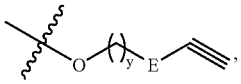

wherein E is an electron withdrawing group, such as a —C(O)O— group and y is 0-6.

As defined generally above, Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^x$ is a crosslinkable amino acid side-chain group and $R^y$ is a hydrophobic amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. In other embodiments, $R^y$ is an ionic amino acid side-chain group. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid non-polar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH$_2$C(O)CH, an aspartic acid side-chain, —CH$_2$CH$_2$C(O)OH, a cystein side-chain, —CH$_2$SH, a serine side-chain, —$CH_2OH$, an aldehyde containing side-chain, —$CH_2C(O)$H, a lysine side-chain, —$(CH_2)_4NH_2$, an arginine side-chain, —$(CH_2)_3NHC(=NH)NH_2$, a histidine side-chain, —$CH_2$-imidazol-4-yl.

As defined generally above, the $R^{2a}$ group of formula I is a mono-protected amine, a di-protected amine, —$NHR^4$, —$N(R^4)_2$, —$NHC(O)R^4$, —$NR^4C(O)R^4$, —$NHC(O)NHR^4$, —$NHC(O)N(R^4)_2$, —$NR^4C(O)NHR^4$, —$NR^4C(O)N(R^4)_2$, —$NHC(O)OR^4$, —$NR^4C(O)OR^4$, —$NHSO_2R^4$, or —$NR^4SO_2R^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula I is —$NHR^4$ or —$N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula I is —$NHR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^{2a}$ group of formula I is —$NHR^4$ wherein $R^4$ is an optionally substituted $C_{2-6}$ alkynyl group. Examples include —$CC\equiv CH$, —$CH_2C\equiv CH$, —$CH_2C\equiv CCH_3$, and —$CH_2CH_2C\equiv CH$.

In certain embodiments, the $R^{2a}$ group of formula I is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{1a}$ group of formula I is —$NHR^4$ wherein $R^4$ is an optionally substituted phenyl ring. Suitable substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$(CH_2)_{0-4}SC(O)R^\circ$; —$(CH_2)_{0-4}C(O)NR^\circ_2$; —$C(S)NR^\circ_2$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; $SiR^\circ_3$; wherein each independent occurrence of $R^\circ$ is as defined herein supra. In other embodiments, the $R^{2a}$ group of formula I is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C\equiv CCH_3$, or —$CH_2C\equiv CH$.

In certain embodiments, the $R^{2a}$ group of formula I is —$NHR^4$ wherein $R^4$ is phenyl substituted with $N_3$, $N(R^\circ)_2$, $CO_2R_\circ$, or $C(O)R^\circ$ wherein each $R^\circ$ is independently as defined herein supra.

In certain embodiments, the $R^{2a}$ group of formula I is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula I is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula I is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula I comprises a group suitable for Click chemistry. One of ordinary skill in the art would recognize that certain $R^{2a}$ groups of the present invention are suitable for Click chemistry.

Compounds of formula I having $R^{2a}$ groups comprising groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the $R^1$ moiety of formula I, can be used to attach targeting groups for cell specific delivery including, but not limited to, fluorescent dyes, covalent attachment to surfaces, and incorporation into hydrogels. Thus, another embodiment of the present invention provides a method of conjugating the $R^{2a}$ group of a compound of formula I to a fluorescent dye, small molecule drug, or macromolecule via Click chemistry. Yet another embodiment of the present invention provides a macromolecule conjugated to a compound of formula I via the $R^{2a}$ group.

According to one embodiment, the $R^{2a}$ group of formula I is an azide-containing group. According to another embodiment, the $R^{2a}$ group of formula I is an alkyne-containing group.

In certain embodiments, the $R^{2a}$ group of formula I has a terminal alkyne moiety. In other embodiments, the $R^{2a}$ group of formula I is an alkyne-containing moiety having an electron withdrawing group. Accordingly, in such embodiments, the $R^{2a}$ group of formula I is

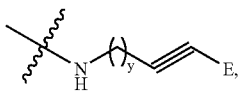

wherein E is an electron withdrawing group and y is 0-6. Such electron withdrawing groups are known to one of ordinary skill in the art. In certain embodiments, E is an ester. In other embodiments, the $R^{2a}$ group of formula I is

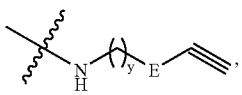

wherein E is an electron withdrawing group, such as a —C(O) O— group and y is 0-6.

In other embodiments, the present invention provides a micelle comprising a multiblock copolymer of formula II:

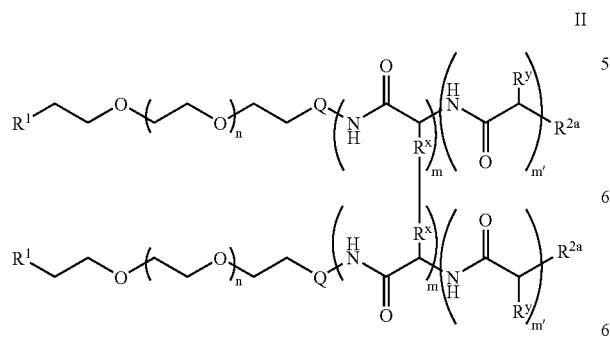

wherein:
n is 10-2500;
m is 1 to 1000;
m' is 1 to 1000;
$R^x$ is a crosslinked natural or unnatural amino acid side-chain group;
$R^y$ is a hydrophobic or ionic, natural or unnatural, amino acid side-chain group;
$R^1$ is -Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched C$_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the present invention provides compounds of formula II, as described above, wherein said compounds have a polydispersity index ("PDI") of about 1.0 to about 1.2. According to another embodiment, the present invention provides compounds of formula II, as described above, wherein said compound has a polydispersity index ("PDI") of about 1.03 to about 1.15. According to yet another embodiment, the present invention provides compounds of formula II, as described above, wherein said compound has a polydispersity index ("PDI") of about 1.10 to about 1.20. According to other embodiments, the present invention provides compounds of formula II having a PDI of less than about 1.10.

As defined generally above, the n group of formula II is 10-2500. In certain embodiments, the present invention provides compounds of formula II, as described above, wherein n is about 225. In other embodiments, n is about 10 to about 40. In other embodiments, n is about 40 to about 60. In still other embodiments, n is about 90 to about 150. In still other embodiments, n is about 200 to about 250. In other embodiments, n is about 300 to about 375. In other embodiments, n is about 400 to about 500. In still other embodiments, n is about 650 to about 750.

In certain embodiments, the m' group of formula II is about 5 to about 500. In certain embodiments, the m' group of formula II is about 10 to about 250. In other embodiments, m' is about 10 to about 50. In other embodiments, m' is about 20 to about 40. According to yet another embodiment, m' is about 50 to about 75. According to other embodiments, m and m' are independently about 10 to about 100. In certain embodiments, m' is 5-50. In other embodiments, m' is 5-10. In other embodiments, m' is 10-20. In certain embodiments, m and m' add up to about 30 to about 60. In still other embodiments, m' is 1-20 repeat units and m' is 10-50 repeat units.

In certain embodiments, the $R^3$ moiety of the $R^1$ group of formula II is —$N_3$.

In other embodiments, the $R^3$ moiety of the $R^1$ group of formula II is —CN.

In still other embodiments, the $R^3$ moiety of the $R^1$ group of formula II is a mono-protected amine or a di-protected amine.

In certain embodiments, the $R^3$ moiety of the $R^1$ group of formula II is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula II is an optionally substituted aryl group. Examples include optionally substituted phenyl and optionally substituted pyridyl. When said $R^3$ moiety is a substituted aryl group, suitable substituents on $R^3$ include CN, $N_3$, $NO_2$, —$CH_3$, —$CH_2N_3$, —$CH=CH_2$, —C≡CH, Br, I, F, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embofiments, the $R^3$ moiety is an aryl group substituted with a suitably protected amino group. According to another aspect, the $R^3$ moiety is phenyl substituted with a suitably protected amino group.

In other embodiments, the $R^3$ moiety of the $R^1$ group of formula II is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula II is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula II is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula II is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiment, the $R^3$ moiety of the $R^1$ group of formula II is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—SCH$_3$, or —S—S(p-ethynylbenzyl). In other embodmients, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula II is a crown ether. Examples of such crown ethers include 12-crown-4, 15-crown-5, and 18-crown-6.

In still other embodiments, the $R^3$ moiety of the $R^1$ group of formula II is a detectable moiety. According to one aspect of the invention, the $R^3$ moiety of the $R^1$ group of formula II is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of formula II is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

In certain embodiments, the $R^3$ moiety of the $R^1$ group of formula II is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula II having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula II to a macromolecule via Click chemistry. Yet another embodiment of the present invention provides a macromolecule conjugated to a compound of formula II via the $R^1$ group.

According to one embodiment, the $R^3$ moiety of the $R^1$ group of formula II is an azide-containing group. According to another embodiment, the $R^3$ moiety of the $R^1$ group of formula II is an alkyne-containing group. In certain embodiments, the $R^3$ moiety of the $R^1$ group of formula II has a terminal alkyne moiety. In other embodiments, $R^3$ moiety of the $R^1$ group of formula II is an alkyne moiety having an electron withdrawing group. Accordingly, in such embodiments, the $R^3$ moiety of the $R^1$ group of formula II is

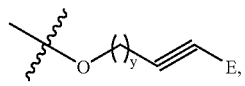

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula II is

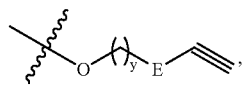

wherein E is an electron withdrawing group, such as a —C(O)O— group and y is 0-6.

As defined generally above, the Q group of formula II is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $R^x$ group of formula II is a crosslinkable amino acid side-chain group and $R^y$ is a hydrophobic amino acid side-chain group. Such hydrophilic, or crosslinkable, amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, a suitably protected aspartic acid or glutamic acid side-chain, histidine or a suitably protected histidine side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, the $R^y$ group of formula II comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —$CH_2C(O)CH$, an aspartic acid side-chain, —$CH_2CH_2C(O)OH$, a cystein side-chain, —$CH_2SH$, a serine side-chain, —$CH_2OH$, an aldehyde containing side-chain, —$CH_2C(O)H$, a lysine side-chain, —$(CH_2)_4NH_2$, an arginine side-chain, —$(CH_2)_3NHC(=NH)NH_2$, a histidine side-chain, —$CH_2$-imidazol-4-yl.

In other embodiments, $R^x$ comprises a mixture of hydrophilic amino acid side-chain groups. Such mixtures of amino acid side-chain groups include those having a carboxylic acid functionality, a hydroxyl functionality, a thiol functionality, and/or amine functionality. It will be appreciated that when $R^x$ comprises a mixture of hydrophilic amino acid side-chain functionalities, then multiple crosslinking can occur. For example, when $R^x$ comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of therapeutic drugs to the cytosol of diseased cells. When $R^x$ comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in drug release exclusively in the cytoplasm.

As defined generally above, the $R^{2a}$ group of formula II is a mono-protected amine, a di-protected amine, —$NHR^4$, —$N(R^4)_2$, —$NHC(O)R^4$, —$NR^4C(O)R^4$, —$NHC(O)NHR^4$, —$NHC(O)N(R^4)_2$, —$NR^4C(O)NHR^4$, —$NR^4C(O)N(R^4)_2$, —$NHC(O)OR^4$, —$NR^4C(O)OR^4$, —$NHSO_2R^4$, or —$NR^4SO_2R^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula II is —$NHR^4$ or —$N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula II is —$NHR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^{2a}$ group of formula II is —$NHR^4$ wherein $R^4$ is an optionally substituted $C_{2-6}$ alkynyl group. Examples include —$CC\equiv CH$, —$CH_2C\equiv CH$, —$CH_2C\equiv CCH_3$, and —$CH_2CH_2C\equiv CH$.

In certain embodiments, the $R^{2a}$ group of formula II is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula II is —$NHR^4$ wherein $R^4$ is an optionally substituted phenyl ring. Suitable substituents on the $R^4$ phenyl ring include halogen; —$(CH_2)_{0-4}R°$; —$(CH_2)_{0-4}OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$(CH_2)_{0-4}SC(O)R°$; —$(CH_2)_{0-4}C(O)NR°_2$; —$C(S)NR°_2$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; $SiR°_3$; wherein each independent occurrence of $R°$ is as defined herein supra. In other embodiments, the $R^{2a}$ group of formula II is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C\equiv CCH_3$, or —$CH_2C\equiv CH$.

In certain embodiments, the $R^{2a}$ group of formula II is —$NHR^4$ wherein $R^4$ is phenyl substituted with $N_3$, $N(R°)_2$, $CO_2R°$, or $C(O)R°$ wherein each $R°$ is independently as defined herein supra.

In certain embodiments, the $R^{2a}$ group of formula II is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula II is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula II is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula II comprises a group suitable for Click chemistry. One of ordinary skill in the art would recognize that certain $R^{2a}$ groups of the present invention are suitable for Click chemistry.

Compounds of formula II having $R^{2a}$ groups comprising groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the $R^1$ moiety of formula II, can be used to attach targeting groups for cell specific delivery including, but not limited to, fluorescent dyes, covalent attachment to surfaces, and incorporation into hydrogels. Thus, another embodiment of the present invention provides a method of conjugating the $R^{2a}$ group of a compound of formula II to a macromolecule via Click chemistry. Yet another embodiment of the present invention provides a macromolecule conjugated to a compound of formula II via the $R^{2a}$ group.

According to one embodiment, the $R^{2a}$ group of formula II is an azide-containing group. According to another embodiment, the $R^{2a}$ group of formula II is an alkyne-containing group.

In certain embodiments, the $R^{2a}$ group of formula II has a terminal alkyne moiety. In other embodiments, the $R^{2a}$ group of formula II is an alkyne-containing moiety having an electron withdrawing group. Accordingly, in such embodiments, the $R^{2a}$ group of formula II is

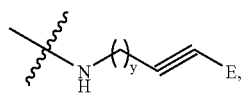

wherein E is an electron withdrawing group and y is 0-6. Such electron withdrawing groups are known to one of ordinary skill in the art. In certain embodiments, E is an ester. In other embodiments, the $R^{2a}$ group of formula II is

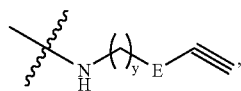

wherein E is an electron withdrawing group, such as a —(O)O— group and y is 0-6.

Exemplary compounds of the present invention are set forth in Tables 1 to 4, below. Table 1 sets forth exemplary compounds of the formula:

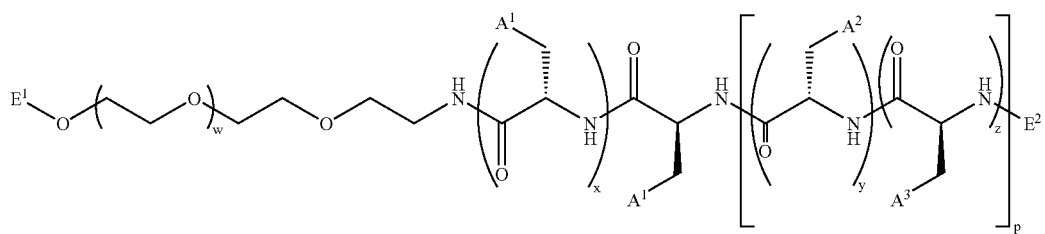

wherein each w is 25-1000, each x is 1-50, each y is 1-50, each z is 1-100, p is the sum of y and z, and each dotted bond represents the point of attachment to the rest of the molecule.

TABLE 1

| Compound | $A^1$ | $A^2$ | $A^3$ | $E^1$ | $E^2$ |
|---|---|---|---|---|---|
| 1 | -C(=O)OH | phenyl | 4-hydroxyphenyl | HC≡C- | -C(=O)CH₃ |
| 2 | -C(=O)OH | phenyl | 4-hydroxyphenyl | N₃-CH₂CH₂- | -C(=O)CH₃ |
| 3 | -C(=O)OH | phenyl | 4-hydroxyphenyl | H₂N-CH₂CH₂- | -C(=O)CH₃ |
| 4 | -C(=O)OH | phenyl | 4-hydroxyphenyl | OHC-CH₂CH₂- | -C(=O)CH₃ |
| 5 | -C(=O)OH | phenyl | 4-hydroxyphenyl | H₃C- | -C(=O)CH₃ |
| 6 | -C(=O)OH | phenyl | 4-hydroxyphenyl | N₃-CH₂CH₂- | -H |
| 7 | -C(=O)OH | phenyl | 4-hydroxyphenyl | H₂N-CH₂CH₂- | -H |
| 8 | -C(=O)OH | phenyl | 4-hydroxyphenyl | OHC-CH₂CH₂- | -H |
| 9 | -C(=O)OH | phenyl | 4-hydroxyphenyl | HC≡C- | -H |

TABLE 1-continued

| Compound | A¹ | A² | A³ | E¹ | E² |
|---|---|---|---|---|---|
| 10 | -COOH | phenyl | 4-hydroxyphenyl | H₃C- | -H |
| 11 | -SH | phenyl | 4-hydroxyphenyl | HC≡C-CH₂- | -C(O)CH₃ |
| 12 | -SH | phenyl | 4-hydroxyphenyl | N₃-CH₂CH₂- | -C(O)CH₃ |
| 13 | -SH | phenyl | 4-hydroxyphenyl | H₂N-CH₂CH₂- | -C(O)CH₃ |
| 14 | -SH | phenyl | 4-hydroxyphenyl | OHC-CH₂CH₂- | -C(O)CH₃ |
| 15 | -SH | phenyl | 4-hydroxyphenyl | H₃C- | -C(O)CH₃ |
| 16 | -SH | phenyl | 4-hydroxyphenyl | N₃-CH₂CH₂- | -H |
| 17 | -SH | phenyl | 4-hydroxyphenyl | H₂N-CH₂CH₂- | -H |
| 18 | -SH | phenyl | 4-hydroxyphenyl | OHC-CH₂CH₂- | -H |
| 19 | -SH | phenyl | 4-hydroxyphenyl | HC≡C-CH₂- | -H |
| 20 | -SH | phenyl | 4-hydroxyphenyl | H₃C- | -H |
| 21 | -COOH | phenyl | -CH₂CH₂CH₂NH₂ | HC≡C-CH₂- | -C(O)CH₃ |
| 22 | -COOH | phenyl | -CH₂CH₂CH₂NH₂ | N₃-CH₂CH₂- | -C(O)CH₃ |

TABLE 1-continued

| Compound | A¹ | A² | A³ | E¹ | E² |
|---|---|---|---|---|---|
| 23 | -C(=O)OH | phenyl | -CH₂CH₂CH₂NH₂ | H₂N-CH₂CH₂- | -C(=O)CH₃ |
| 24 | -C(=O)OH | phenyl | -CH₂CH₂CH₂NH₂ | OHC-CH₂CH₂- | -C(=O)CH₃ |
| 25 | -C(=O)OH | phenyl | -CH₂CH₂CH₂NH₂ | H₃C- | -C(=O)CH₃ |
| 26 | -C(=O)OH | phenyl | -CH₂CH₂CH₂NH₂ | N₃-CH₂CH₂- | H |
| 27 | -C(=O)OH | phenyl | -CH₂CH₂CH₂NH₂ | H₂N-CH₂CH₂- | H |
| 28 | -C(=O)OH | phenyl | -CH₂CH₂CH₂NH₂ | OHC-CH₂CH₂- | H |
| 29 | -C(=O)OH | phenyl | -CH₂CH₂CH₂NH₂ | HC≡C-CH₂- | H |
| 30 | -C(=O)OH | phenyl | -CH₂CH₂CH₂NH₂ | H₃C- | H |
| 31 | -SH | phenyl | -CH₂CH₂CH₂NH₂ | HC≡C-CH₂- | -C(=O)CH₃ |
| 32 | -SH | phenyl | -CH₂CH₂CH₂NH₂ | N₃-CH₂CH₂- | -C(=O)CH₃ |
| 33 | -SH | phenyl | -CH₂CH₂CH₂NH₂ | H₂N-CH₂CH₂- | -C(=O)CH₃ |
| 34 | -SH | phenyl | -CH₂CH₂CH₂NH₂ | OHC-CH₂CH₂- | -C(=O)CH₃ |
| 35 | -SH | phenyl | -CH₂CH₂CH₂NH₂ | H₃C- | -C(=O)CH₃ |
| 36 | -SH | phenyl | -CH₂CH₂CH₂NH₂ | N₃-CH₂CH₂- | H |

TABLE 1-continued

| Compound | A¹ | A² | A³ | E¹ | E² |
|---|---|---|---|---|---|
| 37 | —SH | phenyl | —CH₂CH₂CH₂NH₂ | H₂N-CH₂CH₂— | —H |
| 38 | —SH | phenyl | —CH₂CH₂CH₂NH₂ | OHC-CH₂CH₂— | —H |
| 39 | —SH | phenyl | —CH₂CH₂CH₂NH₂ | HC≡C-CH₂— | —H |
| 40 | —SH | phenyl | —CH₂CH₂CH₂NH₂ | H₃C— | —H |
| 41 | —CH₂COOH | phenyl | —C₆H₄-OH | HC≡C-CH₂— | —C(O)CH₃ |
| 42 | —CH₂COOH | phenyl | —C₆H₄-OH | N₃-CH₂CH₂— | —C(O)CH₃ |
| 43 | —CH₂COOH | phenyl | —C₆H₄-OH | H₂N-CH₂CH₂— | —C(O)CH₃ |
| 44 | —CH₂COOH | phenyl | —C₆H₄-OH | OHC-CH₂CH₂— | —C(O)CH₃ |
| 45 | —CH₂COOH | phenyl | —C₆H₄-OH | H₃C— | —C(O)CH₃ |
| 46 | —CH₂COOH | phenyl | —C₆H₄-OH | N₃-CH₂CH₂— | —H |
| 47 | —CH₂COOH | phenyl | —C₆H₄-OH | H₂N-CH₂CH₂— | —H |
| 48 | —CH₂COOH | phenyl | —C₆H₄-OH | OHC-CH₂CH₂— | —H |
| 49 | —CH₂COOH | phenyl | —C₆H₄-OH | HC≡C-CH₂— | —H |

TABLE 1-continued

| Compound | A¹ | A² | A³ | E¹ | E² |
|---|---|---|---|---|---|
| 50 | CH₂COOH | phenyl | phenyl-OH | H₃C– | –H |
| 51 | CH₂COOH | phenyl | (CH₂)₃NH₂ | HC≡C–CH₂– | –C(O)CH₃ |
| 52 | CH₂COOH | phenyl | (CH₂)₃NH₂ | N₃–(CH₂)₂– | –C(O)CH₃ |
| 53 | CH₂COOH | phenyl | (CH₂)₃NH₂ | H₂N–(CH₂)₂– | –C(O)CH₃ |
| 54 | CH₂COOH | phenyl | (CH₂)₃NH₂ | OHC–(CH₂)₂– | –C(O)CH₃ |
| 55 | CH₂COOH | phenyl | (CH₂)₃NH₂ | H₃C– | –C(O)CH₃ |
| 56 | CH₂COOH | phenyl | (CH₂)₃NH₂ | N₃–(CH₂)₂– | –H |
| 57 | CH₂COOH | phenyl | (CH₂)₃NH₂ | H₂N–(CH₂)₂– | –H |
| 58 | CH₂COOH | phenyl | (CH₂)₃NH₂ | OHC–(CH₂)₂– | –H |
| 59 | CH₂COOH | phenyl | (CH₂)₃NH₂ | HC≡C–CH₂– | –H |
| 60 | CH₂COOH | phenyl | (CH₂)₃NH₂ | H₃C– | –H |
| 61 | COOH | phenyl | CH₂OH | HC≡C–CH₂– | –C(O)CH₃ |
| 62 | COOH | phenyl | CH₂OH | N₃–(CH₂)₂– | –C(O)CH₃ |
| 63 | COOH | phenyl | CH₂OH | H₂N–(CH₂)₂– | –C(O)CH₃ |

TABLE 1-continued

| Compound | A¹ | A² | A³ | E¹ | E² |
|---|---|---|---|---|---|
| 64 | COOH (acetic acid) | phenyl | OCH₃ | CHO-CH₂-CH₂- | acetyl |
| 65 | COOH (acetic acid) | phenyl | OCH₃ | H₃C- | acetyl |
| 66 | CH₂COOH | phenyl | OCH₃ | HC≡C-CH₂- | acetyl |
| 67 | CH₂COOH | phenyl | OCH₃ | N₃-CH₂-CH₂- | acetyl |
| 68 | CH₂COOH | phenyl | OCH₃ | H₂N-CH₂-CH₂- | acetyl |
| 69 | CH₂COOH | phenyl | OCH₃ | CHO-CH₂-CH₂- | acetyl |
| 70 | CH₂COOH | phenyl | OCH₃ | H₃C- | acetyl |
| 71 | COOH | phenyl | imidazolyl | HC≡C-CH₂- | acetyl |
| 72 | COOH | phenyl | indolyl | HC≡C-CH₂- | acetyl |
| 73 | SH | phenyl | imidazolyl | HC≡C-CH₂- | acetyl |
| 74 | SH | phenyl | indolyl | HC≡C-CH₂- | acetyl |
| 75 | CH₂CH₂CH₂NH₂ | phenyl | 4-hydroxyphenyl | HC≡C-CH₂- | acetyl |
| 76 | CH₂CH₂CH₂NH₂ | phenyl | 4-hydroxyphenyl | N₃-CH₂-CH₂- | acetyl |
| 77 | CH₂CH₂CH₂NH₂ | phenyl | 4-hydroxyphenyl | H₂N-CH₂-CH₂- | acetyl |

TABLE 1-continued

| Compound | A¹ | A² | A³ | E¹ | E² |
|---|---|---|---|---|---|
| 78 | propylamine | phenyl | 4-hydroxyphenyl | -CH₂CH₂CHO | -C(O)CH₃ |
| 79 | propylamine | phenyl | 4-hydroxyphenyl | -CH₃ | -C(O)CH₃ |
| 80 | propylamine | phenyl | 4-hydroxyphenyl | -CH₂CH₂N₃ | -H |
| 81 | propylamine | phenyl | 4-hydroxyphenyl | -CH₂CH₂NH₂ | -H |
| 82 | propylamine | phenyl | 4-hydroxyphenyl | -CH₂CH₂CHO | -H |
| 83 | propylamine | phenyl | 4-hydroxyphenyl | -CH₂C≡CH | -H |
| 84 | propylamine | phenyl | 4-hydroxyphenyl | -CH₃ | -H |
| 85 | 1H-imidazol-4-yl | phenyl | 4-hydroxyphenyl | -CH₂C≡CH | -C(O)CH₃ |
| 86 | 1H-imidazol-4-yl | phenyl | 4-hydroxyphenyl | -CH₂CH₂N₃ | -C(O)CH₃ |
| 87 | 1H-imidazol-4-yl | phenyl | 4-hydroxyphenyl | -CH₂CH₂NH₂ | -C(O)CH₃ |
| 88 | 1H-imidazol-4-yl | phenyl | 4-hydroxyphenyl | -CH₂CH₂CHO | -C(O)CH₃ |
| 89 | 1H-imidazol-4-yl | phenyl | 4-hydroxyphenyl | -CH₃ | -C(O)CH₃ |
| 90 | 1H-imidazol-4-yl | phenyl | 4-hydroxyphenyl | -CH₂CH₂N₃ | -H |

TABLE 1-continued

| Compound | A¹ | A² | A³ | E¹ | E² |
|---|---|---|---|---|---|
| 91 | imidazole | phenyl | 4-hydroxyphenyl | H₂N-CH₂CH₂- | H |
| 92 | imidazole | phenyl | 4-hydroxyphenyl | OHC-CH₂CH₂- | H |
| 93 | imidazole | phenyl | 4-hydroxyphenyl | HC≡C-CH₂- | H |
| 94 | imidazole | phenyl | 4-hydroxyphenyl | H₃C- | H |
| 95 | -CH(COOH)- | phenyl | 4-hydroxyphenyl | HS-CH₂CH₂- | C(=O)CH₃ |
| 96 | -CH₂COOH | phenyl | 4-hydroxyphenyl | HS-CH₂CH₂- | C(=O)CH₃ |
| 97 | imidazole | phenyl | 4-hydroxyphenyl | HS-CH₂CH₂- | C(=O)CH₃ |
| 98 | indole | phenyl | 4-hydroxyphenyl | HS-CH₂CH₂- | C(=O)CH₃ |

Table 2 sets forth exemplary compounds of the formula:

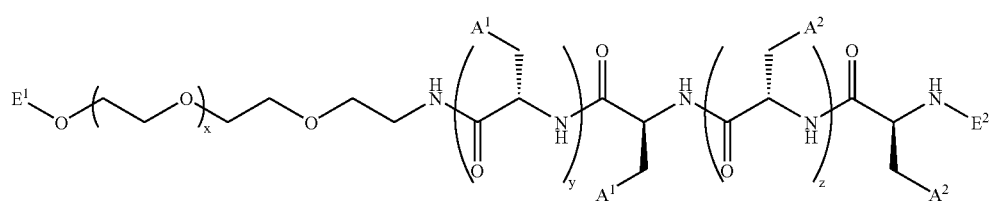

wherein each x is 100-500, each y is 4-20, each z is 5-50, and each dotted bond represents the point of attachment to the rest of the molecule.

TABLE 2

| Compound | A¹ | A² | E¹ | E² |
|---|---|---|---|---|
| 99 | -COOH | phenyl | -C≡C- | -C(=O)- |
| 100 | -COOH | -C(=O)O-CH₂-phenyl | -C≡C- | -C(=O)- |
| 101 | -COOH | -CH(-)-C(=O)O-CH₂-phenyl | -C≡C- | -C(=O)- |
| 102 | -COOH | -(CH₂)₃-NH₂ | -C≡C- | -C(=O)- |
| 103 | -COOH | 1H-imidazol-4-yl | -C≡C- | -C(=O)- |
| 104 | -COOH | 1H-indol-2-yl | -C≡C- | -C(=O)- |
| 105 | -CH₂-COOH | phenyl | -C≡C- | -C(=O)- |
| 106 | -CH₂-COOH | -C(=O)O-CH₂-phenyl | -C≡C- | -C(=O)- |
| 107 | -CH₂-COOH | -CH(-)-C(=O)O-CH₂-phenyl | -C≡C- | -C(=O)- |
| 108 | -CH₂-COOH | -(CH₂)₃-NH₂ | -C≡C- | -C(=O)- |
| 109 | -CH₂-COOH | 1H-imidazol-4-yl | -C≡C- | -C(=O)- |
| 110 | -CH₂-COOH | 1H-indol-2-yl | -C≡C- | -C(=O)- |

TABLE 2-continued

| Compound | A¹ | A² | E¹ | E² |
|---|---|---|---|---|
| 111 | SH | phenyl | alkyne | C(=O)CH₃ |
| 112 | SH | benzyl ester (-C(=O)O-CH₂-Ph) | alkyne | C(=O)CH₃ |
| 113 | SH | -CH₂-C(=O)O-CH₂-Ph | alkyne | C(=O)CH₃ |
| 114 | SH | -(CH₂)₂-NH₂ | alkyne | C(=O)CH₃ |
| 115 | SH | 1H-imidazol-4-yl | alkyne | C(=O)CH₃ |
| 116 | SH | 1H-indol-2-yl | alkyne | C(=O)CH₃ |
| 117 | C(=O)OH | phenyl | H₂N-CH₂CH₂- | C(=O)CH₃ |
| 118 | C(=O)OH | -C(=O)O-CH₂-Ph | H₂N-CH₂CH₂- | C(=O)CH₃ |
| 119 | C(=O)OH | -CH₂-C(=O)O-CH₂-Ph | H₂N-CH₂CH₂- | C(=O)CH₃ |
| 120 | C(=O)OH | -(CH₂)₂-NH₂ | H₂N-CH₂CH₂- | C(=O)CH₃ |
| 121 | C(=O)OH | 1H-imidazol-4-yl | H₂N-CH₂CH₂- | C(=O)CH₃ |
| 122 | C(=O)OH | 1H-indol-2-yl | H₂N-CH₂CH₂- | C(=O)CH₃ |

TABLE 2-continued

| Compound | A¹ | A² | E¹ | E² |
|---|---|---|---|---|
| 123 | -CH₂-C(=O)OH | phenyl | H₂N-CH₂CH₂- | -C(=O)CH₃ |
| 124 | -CH₂-C(=O)OH | -C(=O)O-CH₂-phenyl | H₂N-CH₂CH₂- | -C(=O)CH₃ |
| 125 | -CH₂-C(=O)OH | -CH₂-C(=O)O-CH₂-phenyl | H₂N-CH₂CH₂- | -C(=O)CH₃ |
| 126 | -CH₂-C(=O)OH | -CH₂CH₂CH₂-NH₂ | H₂N-CH₂CH₂- | -C(=O)CH₃ |
| 127 | -CH₂-C(=O)OH | 1H-imidazol-4-yl | H₂N-CH₂CH₂- | -C(=O)CH₃ |
| 128 | -CH₂-C(=O)OH | 1H-indol-2-yl | H₂N-CH₂CH₂- | -C(=O)CH₃ |
| 129 | -SH | phenyl | H₂N-CH₂CH₂- | -C(=O)CH₃ |
| 130 | -SH | -C(=O)O-CH₂-phenyl | H₂N-CH₂CH₂- | -C(=O)CH₃ |
| 131 | -SH | -CH₂-C(=O)O-CH₂-phenyl | H₂N-CH₂CH₂- | -C(=O)CH₃ |
| 132 | -SH | -CH₂CH₂CH₂-NH₂ | H₂N-CH₂CH₂- | -C(=O)CH₃ |
| 133 | -SH | 1H-imidazol-4-yl | H₂N-CH₂CH₂- | -C(=O)CH₃ |
| 134 | -SH | 1H-indol-2-yl | H₂N-CH₂CH₂- | -C(=O)CH₃ |

TABLE 2-continued

| Compound | A¹ | A² | E¹ | E² |
|---|---|---|---|---|
| 135 | -COOH | -phenyl | N₃-CH₂CH₂- | -C(O)CH₃ |
| 136 | -COOH | -C(O)O-CH₂-phenyl | N₃-CH₂CH₂- | -C(O)CH₃ |
| 137 | -COOH | -CH₂C(O)O-CH₂-phenyl | N₃-CH₂CH₂- | -C(O)CH₃ |
| 138 | -COOH | -CH₂CH₂CH₂NH₂ | N₃-CH₂CH₂- | -C(O)CH₃ |
| 139 | -COOH | -imidazolyl | N₃-CH₂CH₂- | -C(O)CH₃ |
| 140 | -COOH | -(1H-indol-2-yl) | N₃-CH₂CH₂- | -C(O)CH₃ |
| 141 | -CH₂COOH | -phenyl | N₃-CH₂CH₂- | -C(O)CH₃ |
| 142 | -CH₂COOH | -C(O)O-CH₂-phenyl | N₃-CH₂CH₂- | -C(O)CH₃ |
| 143 | -CH₂COOH | -CH₂C(O)O-CH₂-phenyl | N₃-CH₂CH₂- | -C(O)CH₃ |
| 144 | -CH₂COOH | -CH₂CH₂CH₂NH₂ | N₃-CH₂CH₂- | -C(O)CH₃ |
| 145 | -CH₂COOH | -imidazolyl | N₃-CH₂CH₂- | -C(O)CH₃ |
| 146 | -CH₂COOH | -(1H-indol-2-yl) | N₃-CH₂CH₂- | -C(O)CH₃ |

TABLE 2-continued

| Compound | A¹ | A² | E¹ | E² |
| --- | --- | --- | --- | --- |
| 147 | -SH | phenyl | N₃-CH₂CH₂- | -C(O)CH₃ |
| 148 | -SH | -OC(O)-CH₂-C₆H₅ (benzyl ester) | N₃-CH₂CH₂- | -C(O)CH₃ |
| 149 | -SH | -CH₂-C(O)O-CH₂-C₆H₅ | N₃-CH₂CH₂- | -C(O)CH₃ |
| 150 | -SH | -(CH₂)₃-NH₂ | N₃-CH₂CH₂- | -C(O)CH₃ |
| 151 | -SH | imidazol-4-yl | N₃-CH₂CH₂- | -C(O)CH₃ |
| 152 | -SH | 1H-indol-2-yl | N₃-CH₂CH₂- | -C(O)CH₃ |
| 153 | imidazol-4-yl | phenyl | HC≡C-CH₂- | -C(O)CH₃ |
| 154 | imidazol-4-yl | -OC(O)-CH₂-C₆H₅ | HC≡C-CH₂- | -C(O)CH₃ |
| 155 | imidazol-4-yl | -CH₂-C(O)O-CH₂-C₆H₅ | HC≡C-CH₂- | -C(O)CH₃ |
| 156 | imidazol-4-yl | -(CH₂)₃-NH₂ | HC≡C-CH₂- | -C(O)CH₃ |
| 157 | imidazol-4-yl | phenyl | N₃-CH₂CH₂- | -C(O)CH₃ |
| 158 | imidazol-4-yl | -OC(O)-CH₂-C₆H₅ | N₃-CH₂CH₂- | -C(O)CH₃ |

TABLE 2-continued

| Compound | A¹ | A² | E¹ | E² |
|---|---|---|---|---|
| 159 | imidazole | benzyl ester acetate | N₃-CH₂CH₂- | acetyl |
| 160 | imidazole | propylamine | N₃-CH₂CH₂- | acetyl |
| 161 | carboxylic acid | phenyl | HS-CH₂CH₂- | acetyl |
| 162 | carboxylic acid | benzyl ester | HS-CH₂CH₂- | acetyl |
| 163 | carboxylic acid | benzyl ester acetate | HS-CH₂CH₂- | acetyl |
| 164 | carboxylic acid | propylamine | HS-CH₂CH₂- | acetyl |
| 165 | carboxylic acid | imidazole | HS-CH₂CH₂- | acetyl |
| 166 | carboxylic acid | indole | HS-CH₂CH₂- | acetyl |
| 167 | -CH₂-COOH | phenyl | HS-CH₂CH₂- | acetyl |
| 168 | -CH₂-COOH | benzyl ester | HS-CH₂CH₂- | acetyl |
| 169 | -CH₂-COOH | benzyl ester acetate | HS-CH₂CH₂- | acetyl |
| 170 | -CH₂-COOH | propylamine | HS-CH₂CH₂- | acetyl |

TABLE 2-continued

| Compound | A¹ | A² | E¹ | E² |
|---|---|---|---|---|
| 171 | acetic acid | imidazole | HS-ethyl | acetyl |
| 172 | acetic acid | 1H-indol-2-yl | HS-ethyl | acetyl |
| 173 | propylamine | phenyl | HS-ethyl | acetyl |
| 174 | propylamine | benzyl ester | HS-ethyl | acetyl |
| 175 | propylamine | benzyl acetate | HS-ethyl | acetyl |
| 176 | propylamine | imidazole | HS-ethyl | acetyl |
| 177 | propylamine | 1H-indol-2-yl | HS-ethyl | acetyl |
| 178 | propylamine | phenyl | propargyl | acetyl |
| 179 | propylamine | benzyl ester | propargyl | acetyl |
| 180 | propylamine | benzyl acetate | propargyl | acetyl |
| 181 | propylamine | imidazole | propargyl | acetyl |
| 182 | propylamine | 1H-indol-2-yl | propargyl | acetyl |

TABLE 2-continued

| Compound | A¹ | A² | E¹ | E² |
|---|---|---|---|---|
| 183 | propylamine | phenyl | azidoethyl | acetyl |
| 184 | propylamine | benzyloxycarbonyl | azidoethyl | acetyl |
| 185 | propylamine | benzyloxycarbonylmethyl | azidoethyl | acetyl |
| 186 | propylamine | 1H-imidazol-4-yl | azidoethyl | acetyl |
| 187 | propylamine | 1H-indol-2-yl | azidoethyl | acetyl |
| 188 | propylamine | phenyl | 3-oxopropyl | acetyl |
| 189 | propylamine | benzyloxycarbonyl | 3-oxopropyl | acetyl |
| 190 | propylamine | benzyloxycarbonylmethyl | 3-oxopropyl | acetyl |
| 191 | propylamine | 1H-imidazol-4-yl | 3-oxopropyl | acetyl |
| 192 | propylamine | 1H-indol-2-yl | 3-oxopropyl | acetyl |

Table 3 sets forth exemplary compounds of the formula:

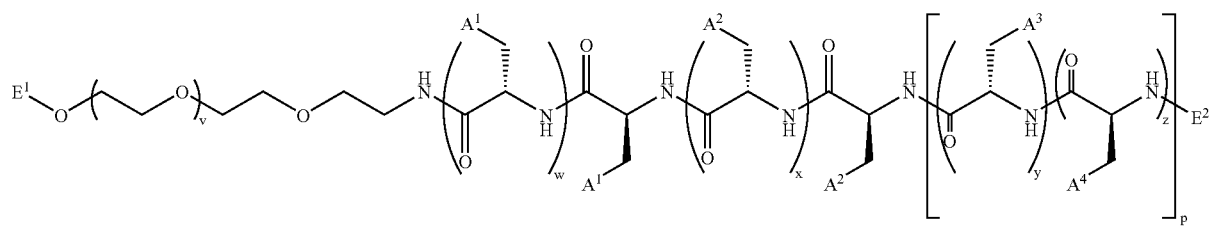

wherein each v is 100-500, each w is 4-20, x is 4-20, each y is 5-50, each z is 5-50, p is the sum of y and z, and each dotted bond represents the point of attachment to the rest of the molecule.

TABLE 3

| Compound | $A^1$ | $A^2$ | $A^3$ | $A^4$ | $E^1$ | $E^2$ |
|---|---|---|---|---|---|---|
| 193 | -C(=O)OH | -SH | phenyl | 4-hydroxyphenyl | HC≡C-CH2- | -C(=O)CH3 |
| 194 | -C(=O)OH | -SH | phenyl | 4-hydroxyphenyl | H2N-CH2CH2- | -C(=O)CH3 |
| 195 | -C(=O)OH | -SH | phenyl | 4-hydroxyphenyl | N3-CH2CH2- | -C(=O)CH3 |
| 196 | -C(=O)OH | -SH | phenyl | 4-hydroxyphenyl | OHC-CH2CH2- | -C(=O)CH3 |
| 197 | -C(=O)OH | -SH | phenyl | 4-hydroxyphenyl | H3C- | -C(=O)CH3 |
| 198 | -CH2-C(=O)OH | -SH | phenyl | 4-hydroxyphenyl | HC≡C-CH2- | -C(=O)CH3 |
| 199 | -CH2-C(=O)OH | -SH | phenyl | 4-hydroxyphenyl | H2N-CH2CH2- | -C(=O)CH3 |
| 200 | -CH2-C(=O)OH | -SH | phenyl | 4-hydroxyphenyl | N3-CH2CH2- | -C(=O)CH3 |
| 201 | -CH2-C(=O)OH | -SH | phenyl | 4-hydroxyphenyl | OHC-CH2CH2- | -C(=O)CH3 |

TABLE 3-continued

| Compound | A¹ | A² | A³ | A⁴ | E¹ | E² |
|---|---|---|---|---|---|---|
| 202 | -CH₂-C(=O)OH | -SH | phenyl | 4-hydroxyphenyl | H₃C- | -C(=O)CH₃ |
| 203 | -C(=O)OH | -SH | phenyl | 4-hydroxyphenyl | HC≡C-CH₂-CH₂- | -H |
| 204 | -C(=O)OH | -SH | phenyl | 4-hydroxyphenyl | H₂N-CH₂-CH₂- | -H |
| 205 | -C(=O)OH | -SH | phenyl | 4-hydroxyphenyl | N₃-CH₂-CH₂- | -H |
| 206 | -C(=O)OH | -SH | phenyl | 4-hydroxyphenyl | OHC-CH₂-CH₂- | -H |
| 207 | -C(=O)OH | -SH | phenyl | 4-hydroxyphenyl | H₃C- | -H |
| 208 | -CH₂-C(=O)OH | -SH | phenyl | 4-hydroxyphenyl | HC≡C-CH₂-CH₂- | -H |
| 209 | -CH₂-C(=O)OH | -SH | phenyl | 4-hydroxyphenyl | H₂N-CH₂-CH₂- | -H |
| 210 | -CH₂-C(=O)OH | -SH | phenyl | 4-hydroxyphenyl | N₃-CH₂-CH₂- | -H |
| 211 | -CH₂-C(=O)OH | -SH | phenyl | 4-hydroxyphenyl | OHC-CH₂-CH₂- | -H |
| 212 | -CH₂-C(=O)OH | -SH | phenyl | 4-hydroxyphenyl | H₃C- | -H |

Table 4 sets forth exemplary compounds of the formula:

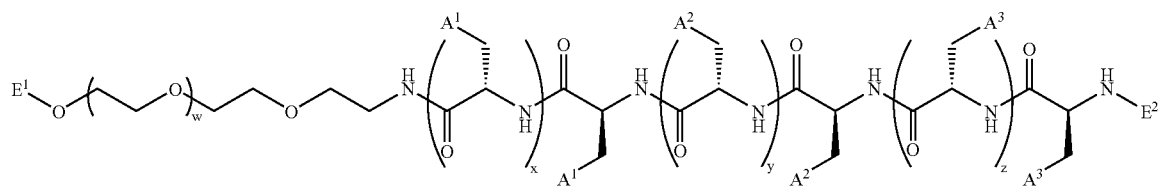

wherein each w is 25-1000, each x is 1-50, y is 1-50, each z is 1-100, and each dotted bond represents the point of attachment to the rest of the molecule.

TABLE 4

| Compound | A¹ | A² | A³ | E¹ | E² |
|---|---|---|---|---|---|
| 213 | -COOH | -SH | phenyl | propynyl | acetyl |
| 214 | -COOH | -SH | 4-hydroxyphenyl | propynyl | acetyl |
| 215 | -COOH | -SH | -CH₂CH₂CH₂NH₂ | propynyl | acetyl |
| 216 | -COOH | -SH | imidazolyl | propynyl | acetyl |
| 217 | -COOH | -SH | indolyl | propynyl | acetyl |
| 218 | -COOH | -SH | -C(O)OCH₂-phenyl | propynyl | acetyl |
| 219 | -COOH | -SH | -CH₂C(O)OCH₂-phenyl | propynyl | acetyl |
| 220 | -CH₂COOH | -SH | phenyl | propynyl | acetyl |
| 221 | -CH₂COOH | -SH | 4-hydroxyphenyl | propynyl | acetyl |

TABLE 4-continued

| Compound | A¹ | A² | A³ | E¹ | E² |
|---|---|---|---|---|---|
| 222 | CH₂COOH | SH | CH₂CH₂CH₂NH₂ | alkyne | C(=O)CH₃ |
| 223 | CH₂COOH | SH | imidazolyl | alkyne | C(=O)CH₃ |
| 224 | CH₂COOH | SH | indolyl | alkyne | C(=O)CH₃ |
| 225 | CH₂COOH | SH | OC(=O)-CH₂-phenyl | alkyne | C(=O)CH₃ |
| 226 | CH₂COOH | SH | CH₂C(=O)O-CH₂-phenyl | alkyne | C(=O)CH₃ |
| 227 | COOH | SH | phenyl | alkyne | H |
| 228 | COOH | SH | 4-hydroxyphenyl | alkyne | H |
| 229 | COOH | SH | CH₂CH₂CH₂NH₂ | alkyne | H |
| 230 | COOH | SH | imidazolyl | alkyne | H |
| 231 | COOH | SH | indolyl | alkyne | H |
| 232 | COOH | SH | OC(=O)-CH₂-phenyl | alkyne | H |
| 233 | COOH | SH | CH₂C(=O)O-CH₂-phenyl | alkyne | H |

TABLE 4-continued

| Compound | A¹ | A² | A³ | E¹ | E² |
|---|---|---|---|---|---|
| 234 | CH₂COOH | SH | phenyl | alkyne-CH₂ | H |
| 235 | CH₂COOH | SH | 4-hydroxyphenyl | alkyne-CH₂ | H |
| 236 | CH₂COOH | SH | (CH₂)₃NH₂ | alkyne-CH₂ | H |
| 237 | CH₂COOH | SH | imidazol-2-yl | alkyne-CH₂ | H |
| 238 | CH₂COOH | SH | 1H-indol-2-yl | alkyne-CH₂ | H |
| 239 | CH₂COOH | SH | -C(=O)O-CH₂-phenyl | alkyne-CH₂ | H |
| 240 | CH₂COOH | SH | -CH₂-C(=O)O-CH₂-phenyl | alkyne-CH₂ | H |
| 241 | COOH | SH | phenyl | N₃-CH₂CH₂- | -C(=O)CH₃ |
| 242 | COOH | SH | 4-hydroxyphenyl | N₃-CH₂CH₂- | -C(=O)CH₃ |
| 243 | COOH | SH | (CH₂)₃NH₂ | N₃-CH₂CH₂- | -C(=O)CH₃ |
| 244 | COOH | SH | imidazol-4-yl | N₃-CH₂CH₂- | -C(=O)CH₃ |
| 245 | COOH | SH | 1H-indol-2-yl | N₃-CH₂CH₂- | -C(=O)CH₃ |

TABLE 4-continued

| Compound | A¹ | A² | A³ | E¹ | E² |
|---|---|---|---|---|---|
| 246 | COOH | SH | C(=O)O-CH2-Ph | N3-CH2CH2CH2- | C(=O)CH3 |
| 247 | COOH | SH | CH2-C(=O)O-CH2-Ph | N3-CH2CH2CH2- | C(=O)CH3 |
| 248 | CH2-COOH | SH | Ph | N3-CH2CH2CH2- | C(=O)CH3 |
| 249 | CH2-COOH | SH | 4-HO-C6H4- | N3-CH2CH2CH2- | C(=O)CH3 |
| 250 | CH2-COOH | SH | -CH2CH2CH2-NH2 | N3-CH2CH2CH2- | C(=O)CH3 |
| 251 | CH2-COOH | SH | imidazol-4-yl | N3-CH2CH2CH2- | C(=O)CH3 |
| 252 | CH2-COOH | SH | indol-2-yl | N3-CH2CH2CH2- | C(=O)CH3 |
| 254 | CH2-COOH | SH | C(=O)O-CH2-Ph | N3-CH2CH2CH2- | C(=O)CH3 |
| 255 | CH2-COOH | SH | CH2-C(=O)O-CH2-Ph | N3-CH2CH2CH2- | C(=O)CH3 |
| 256 | COOH | SH | Ph | N3-CH2CH2CH2- | H |
| 257 | COOH | SH | 4-HO-C6H4- | N3-CH2CH2CH2- | H |
| 258 | COOH | SH | -CH2CH2CH2-NH2 | N3-CH2CH2CH2- | H |

TABLE 4-continued

| Compound | A¹ | A² | A³ | E¹ | E² |
|---|---|---|---|---|---|
| 259 | COOH | SH | imidazole | N₃-CH₂CH₂- | H |
| 260 | COOH | SH | 1H-indol-2-yl | N₃-CH₂CH₂- | H |
| 261 | COOH | SH | -C(=O)O-CH₂-Ph | N₃-CH₂CH₂- | H |
| 262 | COOH | SH | -CH₂-C(=O)O-CH₂-Ph | N₃-CH₂CH₂- | H |
| 263 | -CH₂-COOH | SH | phenyl | N₃-CH₂CH₂- | H |
| 264 | -CH₂-COOH | SH | 4-hydroxyphenyl | N₃-CH₂CH₂- | H |
| 265 | -CH₂-COOH | SH | -CH₂CH₂-NH₂ | N₃-CH₂CH₂- | H |
| 266 | -CH₂-COOH | SH | imidazole | N₃-CH₂CH₂- | H |
| 267 | -CH₂-COOH | SH | 1H-indol-2-yl | N₃-CH₂CH₂- | H |
| 268 | -CH₂-COOH | SH | -C(=O)O-CH₂-Ph | N₃-CH₂CH₂- | H |
| 269 | -CH₂-COOH | SH | -CH₂-C(=O)O-CH₂-Ph | N₃-CH₂CH₂- | H |
| 270 | COOH | SH | phenyl | OHC-CH₂CH₂- | -C(=O)CH₃ |

TABLE 4-continued

| Compound | A¹ | A² | A³ | E¹ | E² |
|---|---|---|---|---|---|
| 271 | -COOH | -SH | -C₆H₄-OH (para) | -CH₂CH₂CHO | -C(=O)CH₃ |
| 272 | -COOH | -SH | -CH₂CH₂NH₂ | -CH₂CH₂CHO | -C(=O)CH₃ |
| 273 | -COOH | -SH | -(imidazol-4-yl) | -CH₂CH₂CHO | -C(=O)CH₃ |
| 274 | -COOH | -SH | -(1H-indol-2-yl) | -CH₂CH₂CHO | -C(=O)CH₃ |
| 275 | -COOH | -SH | -C(=O)-O-CH₂-C₆H₅ | -CH₂CH₂CHO | -C(=O)CH₃ |
| 276 | -COOH | -SH | -CH₂-C(=O)-O-CH₂-C₆H₅ | -CH₂CH₂CHO | -C(=O)CH₃ |
| 277 | -CH₂COOH | -SH | -C₆H₅ | -CH₂CH₂CHO | -C(=O)CH₃ |
| 278 | -CH₂COOH | -SH | -C₆H₄-OH (para) | -CH₂CH₂CHO | -C(=O)CH₃ |
| 279 | -CH₂COOH | -SH | -CH₂CH₂NH₂ | -CH₂CH₂CHO | -C(=O)CH₃ |
| 280 | -CH₂COOH | -SH | -(imidazol-4-yl) | -CH₂CH₂CHO | -C(=O)CH₃ |
| 281 | -CH₂COOH | -SH | -(1H-indol-2-yl) | -CH₂CH₂CHO | -C(=O)CH₃ |
| 282 | -CH₂COOH | -SH | -C(=O)-O-CH₂-C₆H₅ | -CH₂CH₂CHO | -C(=O)CH₃ |

TABLE 4-continued

| Compound | A¹ | A² | A³ | E¹ | E² |
|---|---|---|---|---|---|
| 283 | CH₂COOH | SH | CH₂C(O)O-CH₂-phenyl | CH₂CH₂CHO | C(O)CH₃ |
| 284 | CH(COOH) | SH | phenyl | CH₂CH₂CHO | H |
| 285 | CH(COOH) | SH | 4-hydroxyphenyl | CH₂CH₂CHO | H |
| 286 | CH(COOH) | SH | CH₂CH₂CH₂NH₂ | CH₂CH₂CHO | H |
| 287 | CH(COOH) | SH | imidazol-4-yl | CH₂CH₂CHO | H |
| 288 | CH(COOH) | SH | 1H-indol-2-yl | CH₂CH₂CHO | H |
| 289 | CH(COOH) | SH | C(O)O-CH₂-phenyl | CH₂CH₂CHO | H |
| 290 | CH(COOH) | SH | CH₂C(O)O-CH₂-phenyl | CH₂CH₂CHO | H |
| 291 | CH₂COOH | SH | phenyl | CH₂CH₂CHO | H |
| 292 | CH₂COOH | SH | 4-hydroxyphenyl | CH₂CH₂CHO | H |
| 293 | CH₂COOH | SH | CH₂CH₂CH₂NH₂ | CH₂CH₂CHO | H |
| 294 | CH₂COOH | SH | imidazol-4-yl | CH₂CH₂CHO | H |

TABLE 4-continued

| Compound | A¹ | A² | A³ | E¹ | E² |
|---|---|---|---|---|---|
| 295 | –CH₂C(O)OH | –SH | (indole structure) | –C(O)CH₂CH₂– H | H |
| 296 | –CH₂C(O)OH | –SH | –OC(O)OCH₂-phenyl | –C(O)CH₂CH₂– H | H |
| 297 | –CH₂C(O)OH | –SH | –OC(O)CH₂O-benzyl | –C(O)CH₂CH₂– H | H |

B. Crosslinking Chemistries

In addition to advances in polymer micelle technology, significant efforts have been made in the development of stimuli-responsive polymeric materials that can respond to environmental pH changes. See Chatteijee, J.; Haik, Y.; Chen, C. J. *J. App. Polym. Sci.* 2004, 91, 3337-3341; Du, J. Z.; Armes, S. P. *J. Am. Chem. Soc.* 2005, 127, 12800-12801; and Twaites, B. R.; de las Heras Alarcon, C.; Cunliffe, D.; Lavigne, M.; Pennadam, S.; Smith, J. R.; Gorecki, D. C.; Alexander, C. *J. Control. Release* 2004, 97, 551-566. This is of importance for sensitive protein and nucleic acid-based drugs where escape from acidic intracellular comparments (i.e. endosome and lysosome) and cytoplasmic release are required to achieve therapeutic value. See Murthy, N.; Campbell, J.; Fausto, N.; Hoffman, A. S.; Stayton, P. S. *J. Control. Release* 2003, 89, 365-374; E1-Sayed, M. E. H.; Hoffman, A. S.; Stayton, P. S. *J. Control. Release* 2005, 104, 417-427; and Liu, Y.; Wenning, L.; Lynch, M.; Reineke, T. *J. Am. Chem. Soc.* 2004, 126, 7422-7423. Acid-sensitive delivery systems that can successfully escape the endosome and transport small-molecule chemotherapeutic drugs into the cytoplasm are also of interest since these carriers can bypass many of the cellular mechanisms responsible for multi-drug resistance. In some of these cases, the polymers are designed to respond to the significant pH gradient between the blood (pH 7.4) and the late-early endosome (pH~5.0-6.0).

There is an additional interest in developing the cancer-specific, pH-sensitive targeting of therapeutics. For example, rapidly growing cells found in solid tumors have elevated glycolytic rates and increased lactic acid production when compared to healthy cells. These factors, along with poor lymphatic drainage present in cancerous tissue result in an excess of lactic acid and a subtle pH gradient between the blood and the solid tumor microenvironment (pH 6.5-7.0). See Kalllinowski, F.; Schlenger, K. H.; Runkel, S.; Kloes, M.; Stohrer, M.; Okunieff, P.; Vaupel, P. *Cancer Res.* 1989, 49, 3759-3764. Although the design of materials which can respond to such small pH variations is clearly challenging, this mechanism, coupled with the EPR effect, represent an effective method for limiting drug release to solid tumors.

In certain embodiments, the amphiphilic block copolymers and cell-responsive polymer micelles of the present invention are designed to combine the concepts of crosslinked polymer micelles and pH-sensitive drug targeting to construct "smart" nanovectors that are infinitely stable to dilution in the bloodstream but are chemically programmed to release their therapeutic payload in response to pH changes commonly found in solid tumors and cancer cells. By utilizing cancer-responsive nanovectors in conjunction with potent chemotherapeutic agents, long-standing clinical problems such as post-injection micelle stability and the targeted delivery of encapsulated therapeutics to cancer cells are addressed. Unlike previous examples of micelle crosslinking (i.e., core and shell crosslinking), the multi-block approach of the present invention allows for the effective crosslinking of polymer segments located at the interface of the hydrophobic and hydrophilic polymer blocks as shown in FIG. 1. This approach is advantageous because stable micelles are prepared without sacrificing loading efficiency or altering the drug molecule during core crosslinking.

In contrast to shell-crosslinked micelles, the crosslinking of multiblock copolymer micelles in accordance with the present invention is accomplished without large dilution volumes because micelle-micelle coupling does not occur. Such crosslinking will enhance post-administration circulation time leading to more efficient passive drug targeting by the EPR effect and improved active targeting using cancer-specific targeting groups. In addition, stimuli-responsive crosslinking may offer another targeting mechanism to isolate the release of the chemotherapy drug exclusively within the tumor tissue and cancer cell cytoplasm.

Crosslinking reactions designed for drug delivery preferably meet a certain set of requirements to be deemed safe and useful for in vivo applications. For example, in other embodiments, the crosslinking reaction would utilize non-cytotoxic reagents, would be insensitive to water, would not alter the drug to be delivered, and in the case of cancer therapy, would be reversible at pH levels commonly encountered in tumor tissue (pH~6.8) or acidic organelles in cancer cells (pH~5.0-6.0).

In certain embodiments, micelles of the present invention comprise a crosslinked multiblock polymer of formula III:

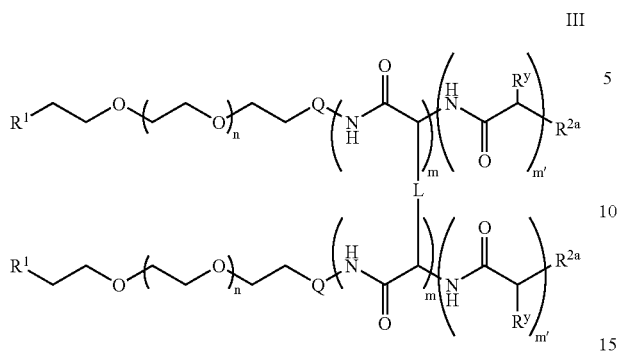

wherein:

n is 10-2500;

m is 1 to 1000;

m' is 1 to 1000;

L is a bivalent, saturated or unsaturated, straight or branched $C_{1-12}$ alkylene chain, wherein 0-6 methylene units of L are independently replaced by -M-, -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-M- is a suitable bivalent metal;

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^y$ is a hydrophobic or ionic, natural or unnatural amino acid side-chain group;

$R^1$ is -Z(CH$_2$CH$_2$Y)$_p$(CH$_2$)$_t$R$^3$, wherein:

Z is —O—, —S—, —C≡C—, or —CH$_2$—;

each Y is independently —O— or —S—;

p is 0-10;

t is 0-10; and $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the present invention provides compounds of formula III, as described above, wherein said compounds have a polydispersity index ("PDI") of about 1.0 to about 1.2. According to another embodiment, the present invention provides compounds of formula III, as described above, wherein said compound has a polydispersity index ("PDI") of about 1.03 to about 1.15. According to yet another embodiment, the present invention provides compounds of formula I, as described above, wherein said compound has a polydispersity index ("PDI") of about 1.10 to about 1.20. According to other embodiments, the present invention provides compounds of formula III having a PDI of less than about 1.10.

As defined generally above, the n group of formula III is 10-2500. In certain embodiments, the present invention provides compounds of formula III, as described above, wherein n is about 225. In other embodiments, n is about 10 to about 40. In other embodiments, n is about 40 to about 60. In still other embodiments, n is about 90 to about 150. In still other embodiments, n is about 200 to about 250. In other embodiments, n is about 300 to about 375. In other embodiments, n is about 400 to about 500. In still other embodiments, n is about 650 to about 750.

In certain embodiments, the m' group of formula III is about 5 to about 500. In certain embodiments, the m' group of formula III is about 10 to about 250. In other embodiments, m' is about 10 to about 50. In other embodiments, m' is about 20 to about 40. According to yet another embodiment, m' is about 50 to about 75. According to other embodiments, m and m' are independently about 10 to about 100. In certain embodiments, m' is 5-50. In other embodiments, m' is 5-10. In other embodiments, m' is 10-20. In certain embodiments, m and m' add up to about 30 to about 60. In still other embodiments, m' is 1-20 repeat units and m' is 10-50 repeat units.

As defined generally above, the L group of formula III is a bivalent, saturated or unsaturated, straight or branched $C_{1-12}$ alkylene chain, wherein 0-6 methylene units of L are independently replaced by -M-, Cy, —O—, NH—, —S—, —C(O)—, —SO—, —SO2—, NHC(O)—, C(O)NH—, OC(O)NH—, or —NHC(O)O—, wherein -M- is a suitable bivalent metal, and -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. It will be appreciated that the L group of formula III represents crosslinked amino acid side-chain groups. In certain embodiments, the crosslinked amino acid side-chain groups correspond to the $R^x$ moiety of compounds of formulae I and II as described herein. In certain embodiments, the L group of formula III represents a metal crosslinked amino acid side-chain group, a hydrazone crosslinked amino acid side-chain group, an ester crosslinked amino acid side-chain group, an amide crosslinked side-chain group, an imine (e.g. Schiff base) crosslinked side-chain group, or a disulfide crosslinked side-chain group.

In certain embodiments, the L group of formula III comprises -M-. In other embodiments, -M- is zinc, calcium, iron or aluminum. In yet other embodiments, -M- is strontium, manganese, palladium, silver, gold, cadmium, chromium, indium, or lead.

In other embodiments, the L group of formula III is a bivalent, saturated or unsaturated, straight or branched $C_{1-12}$ alkylene chain wherein 2 methylene units of L are independently replaced by —C(O)—, —C(O)NH—, —NHC(O)—, —S—, —C(O)O—, —OC(O)—, —C(O)NHN—, -=NNHC(O)—, -=N—, —N=-, -M-OC(O)—, or —C(O)O-M-. According to another embodiment, the L group of formula III is a bivalent, saturated or unsaturated, straight or branched $C_{1-6}$ alkylene chain, wherein two methylene units of L are replaced by —C(O)— or —C(O)NH—. In other embodiments, the L group of formula III is a bivalent, saturated or unsaturated, straight or branched $C_{1-12}$ alkylene chain having at least 2 units of unsaturation. According to yet another embodiment, the L group of formula III is a bivalent, saturated or unsaturated, straight or branched $C_{1-12}$ alkylene chain wherein two methylene units of L are replaced by —NH—. According to yet another embodiment, the L group of formula III is a bivalent, saturated or unsaturated, straight or branched $C_{1-12}$ alkylene chain wherein two methylene units of L are replaced by —C(O)NHN.

In certain embodiments, the -M- moiety of the L group of formula III is zinc. In other embodiments, L forms a zinc-dicarboxylate crosslinking moiety. In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

Scheme 1

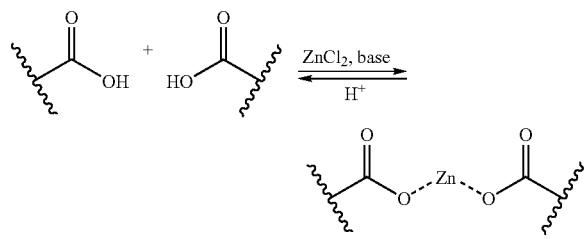

Scheme 1 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 4.0-6.8 to reform $ZnX_2$, where X is the conjugate base. One of ordinary skill in the art will recognize that a variety of natural and unnatural amino acid side-chains have a carboxylic acid moeity that can be crosslinked by zinc or another suitable metal.

In certain embodiments, L represents aspartic acid side-chains crosslinked with zinc. Without wishing to be bound by theory, it is believed that the zinc aspartate crosslinks are stable in the blood compartment (pH 7.4), allowing for effective accumulation of the drug-loaded micelles in solid tumors by passive and active targeting mechanisms. In the presence of lactic acid concentrations commonly encountered in solid tumors or in acidic organelles of cancer cells, rapid degradation of the metal crosslinks leading to micelle dissociation and release of the drug at the tumor site. Preliminary, qualitative studies have shown that crosslinked zinc aspartate segments are reversible in the presence of α-hydroxyacids.

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

The ultimate goal of metal-mediated crosslinking is to ensure micelle stability when diluted in the blood (pH 7.4) followed by rapid dissolution and drug release in response to a finite pH change such as those found in cancer cells. Previous reports suggest a widely variable and tunable dissociation pH for zinc-acid bonds (from approximately 2.0 to 7.0) depending on the carboxylic acid used and number of bonds formed. See Cannan, R. K.; Kibrick, A. *J. Am. Chem. Soc.* 1938, 60, 2314-2320. Without wishing to be bound by theory, it is believed that the concentration of zinc chloride and the number of aspartic acid, or other carboxylic acid-containing amino acid, repeat units in the crosslinking block will ultimately control the pH at which complete micelle disassembly occurs. The synthetic versatility of the block copolymer design is advantageous since one or more variables are tuned to achieve the desired pH reversibility. By simple adjustment of zinc chloride/polymer stoichiometry, pH-reversible crosslinking is finely tuned across the pH range of interest. For example, higher zinc concentrations yield more zinc crosslinks which require higher acid concentrations (i.e. lower pH) to dissociate. Adjustments in zinc/polymer stoichiometry will yield the desired pH reversibility, however other variables such as increasing the poly(aspartic acid) block length (i.e. 15-25 repeat units) further tune the reversible crosslinking reaction if necessary.

In other embodiments, L comprises a mixture of crosslinked hydrophilic amino acid side-chain groups. Such mixtures of amino acid side-chain groups include those having a carboxylic acid functionality, a hydroxyl functionality, a thiol functionality, and/or amine functionality. It will be appreciated that when L comprises a mixture of crosslinked hydrophilic amino acid side-chain functionalities, then multiple crosslinking can occur. For example, when L comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of therapeutic drugs to the cytosol of diseased cells because a second stimuli must be present to allow for drug reslease. For example, micelles possessing both carboxylic acid-zinc crosslinking and cysteine dithiol crosslinking would be required to enter an acidic environment (e.g. a tumor) and enter an environment with a high concentration of glutathione (e.g. in the cell cytoplasm). When L comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in drug release exclusively in the cytoplasm.

Exemplary crosslinking reactions and resulting L groups are depicted in FIGS. 2 through 10.

In certain embodiments, the $R^3$ moiety of the $R^1$ group of formula III is —$N_3$.

In other embodiments, the $R^3$ moiety of the $R^1$ group of formula III is —CN.

In still other embodiments, the $R^3$ moiety of the $R^1$ group of formula III is a mono-protected amine or a di-protected amine.

In certain embodiments, the $R^3$ moiety of the $R^1$ group of formula III is an optionally substituted aliphatic group. Examples include t-butyl, 5-norbornene-2-yl, octane-5-yl, acetylenyl, trirethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula III is an optionally substituted aryl group. Examples include optionally substituted phenyl and optionally substituted pyridyl. When said $R^3$ moiety is a substituted aryl group, suitable substituents on $R^3$ include CN, $N_3$, $NO_2$, —$CH_3$, —$CH_2N_3$, —CH=$CH_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embofiments, the $R^3$ moiety is an aryl group substituted with a suitably protected amino group. According to another aspect, the $R^3$ moiety is phenyl substituted with a suitably protected amino group.

In certain embodiments, the $R^3$ moiety of the $R^1$ group of formula III is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula III is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula I is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula III is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiments, the $R^3$ moiety of the $R^1$ group of formula III is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodmients, $R^3$ is —S—S-pyridin-2-yl, —S—SBn, —S—SCH$_3$, or —S—S(p-ethynylbenzyl). In other embodmients, $R^3$ is —S—S-pyridin-2-yl. In still other embodiments, the $R^1$ group is 2-triphenyl-methylsulfanyl-ethoxy.

In certain embodiments, the $R^3$ moiety of the $R^1$ group of formula III is a crown ether. Examples of such crown ethers include 12-crown-4, 15-crown-5, and 18-crown-6.

In still other embodiments, the $R^3$ moiety of the $R^1$ group of formula III is a detectable moiety. According to one aspect of the invention, the $R^3$ moiety of the $R^1$ group of formula III is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343.

In certain embodiments, the $R^3$ moiety of the $R^1$ group of formula III is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

In certain embodiments, the $R^3$ moiety of the $R^1$ group of formula III is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula III to a macromolecule via Click chemistry. Yet another embodiment of the present invention provides a macromolecule conjugated to a compound of formula III via the $R^1$ group.

According to one embodiment, the $R^3$ moiety of the $R^1$ group of formula III is an azide-containing group. According to another embodiment, the $R^3$ moiety of the $R^1$ group of formula III is an alkyne-containing group. In certain embodiments, the $R^3$ moiety of the $R^1$ group of formula III has a terminal alkyne moiety. In other embodiments, $R^3$ moiety of the $R^1$ group of formula III is an alkyne moiety having an electron withdrawing group. Accordingly, in such embodiments, the $R^3$ moiety of the $R^1$ group of formula III is

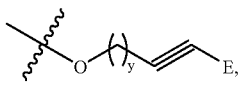

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula III is

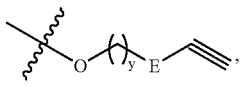

wherein E is an electron withdrawing group, such as a —C(O)O— group and y is 0-6.

As defined generally above, Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^y$ is a hydrophobic amino acid side-chain group. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol functional groups of $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined generally above, the $R^{2a}$ group of formula III is a mono-protected amine, a di-protected amine, $-NHR^4$, $-N(R^4)_2$, $-NHC(O)R^4$, $-NR^4C(O)R^4$, $-NHC(O)NHR^4$, $-NHC(O)N(R^4)_2$, $-NR^4C(O)NHR^4$, $-NR^4C(O)N(R^4)_2$, $-NHC(O)OR^4$, $-NR^4C(O)OR^4$, $-NHSO_2R^4$, or $-NR^4SO_2R^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula III is $-NHR^4$ or $-N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula III is $-NHR^4$ wherein $R^4$ is a $C_{1-6}$ aliphatic group substituted with $N_3$. Examples include $-CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is $-CH_2CN$, $-CH_2CH_2CN$, $-CH_2CH(OCH_3)_2$, 4-(bisbenzyloxymethyl)phenylmethyl, and the like.

According to another aspect of the present invention, the $R^{2a}$ group of formula III is $-NHR^4$ wherein $R^4$ is an optionally substituted $C_{2-6}$ alkynyl group. Examples include $-CC\equiv CH$, $-CH_2C\equiv CH$, $-CH_2C\equiv CCH_3$, and $-CH_2CH_2C\equiv CH$.

In certain embodiments, the $R^{2a}$ group of formula III is $-NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula III is $-NHR^4$ wherein $R^4$ is an optionally substituted phenyl ring. Suitable substituents on the $R^4$ phenyl ring include halogen; $-(CH_2)_{0-4}R°$; $-(CH_2)_{0-4}OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-(CH_2)_{0-4}SC(O)R°$; $-(CH_2)_{0-4}C(O)NR°_2$; $-C(S)NR°_2$; $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R_{12}$; $-OP(O)R_{12}$; $SiR°_3$; wherein each independent occurrence of $R°$ is as defined herein supra. In other embodiments, the $R^{2a}$ group of formula III is $-NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, $-CH_2N_3$, $-CH_2CH_2N_3$, $-CH_2C\equiv CCH_3$, or $-CH_2C\equiv CH$.

In certain embodiments, the $R^{2a}$ group of formula III is $-NHR^4)_2$ wherein $R^4$ is phenyl substituted with $N_3$, $N(R°)_2$, $CO_2R°$, or $C(O)R°$ wherein each $R°$ is independently as defined herein supra.

In certain embodiments, the $R^{2a}$ group of formula III is $-N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula III is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula III is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxycarbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula III comprises a group suitable for Click chemistry. One of ordinary skill in the art would recognize that certain $R^{2a}$ groups of the present invention are suitable for Click chemistry.

Compounds of formula III having $R^{2a}$ groups comprising groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the $R^1$ moiety of formula III, can be used to attach targeting groups for cell specific delivery including, but not limited to, fluorescent dyes, covalent attachment to surfaces, and incorporation into hydrogels. Thus, another embodiment of the present invention provides a method of conjugating the $R^{2a}$ group of a compound of formula III to a macromolecule via Click chemistry. Yet another embodiment of the present invention provides a macromolecule conjugated to a compound of formula III via the $R^{2a}$ group.

According to one embodiment, the $R^{2a}$ group of formula III is an azide-containing group. According to another embodiment, the $R^{2a}$ group of formula III is an alkyne-containing group.

In certain embodiments, the $R^{2a}$ group of formula III has a terminal alkyne moiety. In other embodiments, the $R^{2a}$ group of formula III is an alkyne-containing moiety having an electron withdrawing group. Accordingly, in such embodiments, the $R^{2a}$ group of formula III is

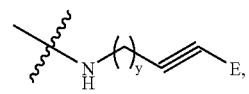

wherein E is an electron withdrawing group and y is 0-6. Such electron withdrawing groups are known to one of ordinary skill in the art. In certain embodiments, E is an ester. In other embodiments, the $R^{2a}$ group of formula III is

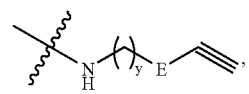

wherein E is an electron withdrawing group, such as a —(O)O— group and y is 0-6.

Exemplary $R^1$ groups of any of formulae I, II, and III are set forth in Table 5, below.

TABLE 5

Representative $R^1$ Groups

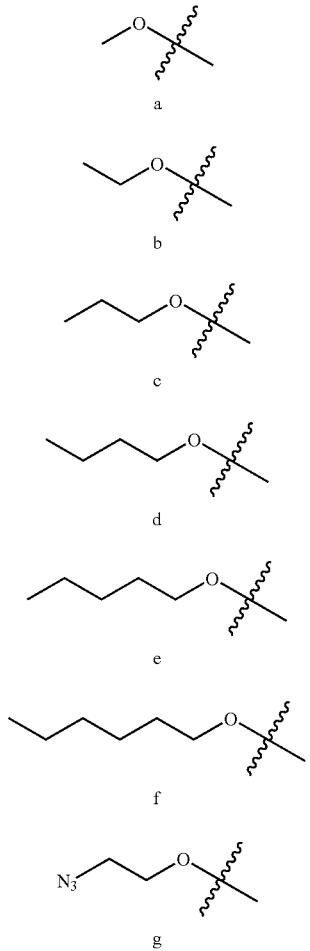

TABLE 5-continued
Representative R¹ Groups
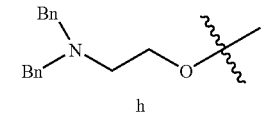
h
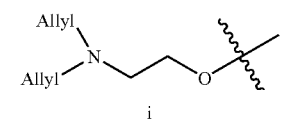
i
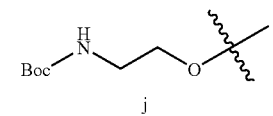
j
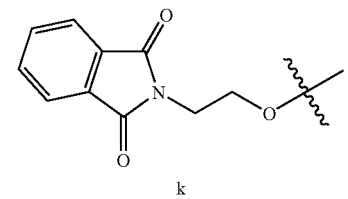
k
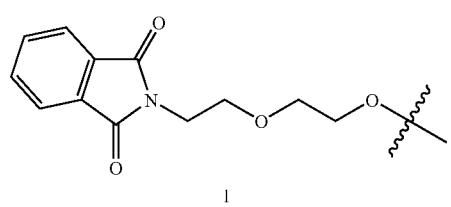
l
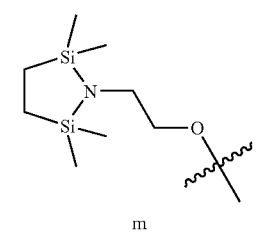
m
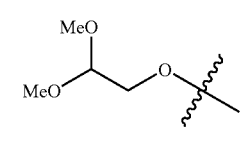
n
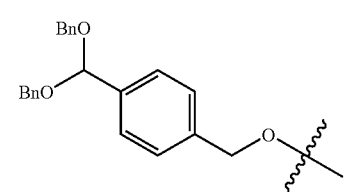
o
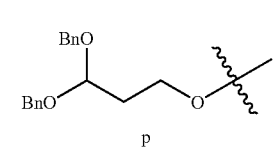
p
TABLE 5-continued
Representative R¹ Groups
q
r
s
t
u
v
w
x
y TABLE 5-continued
Representative R¹ Groups
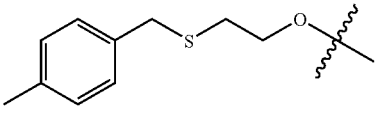
z
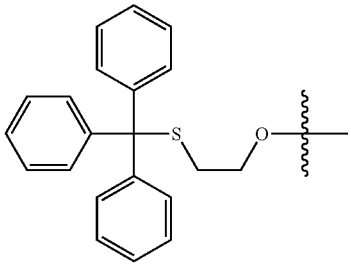
aa
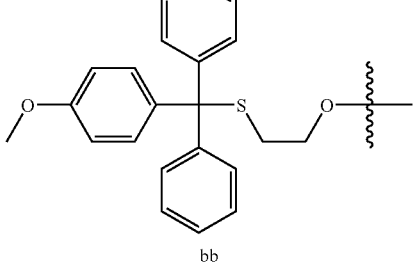
bb
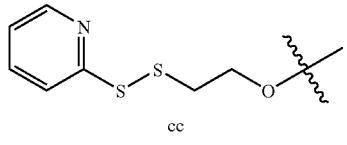
cc
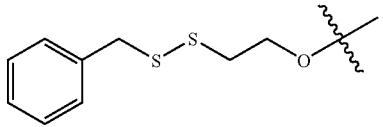
dd
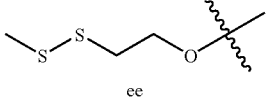
ee
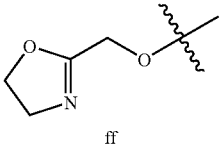
ff
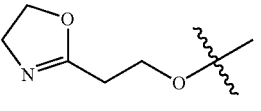
gg
TABLE 5-continued
Representative R¹ Groups
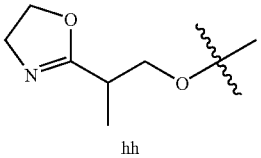
hh
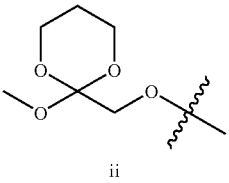
ii
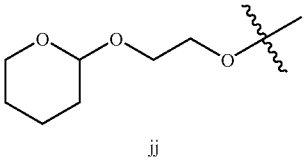
jj
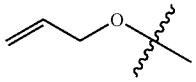
kk
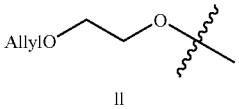
ll
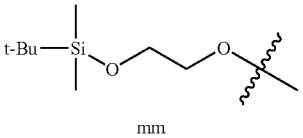
mm
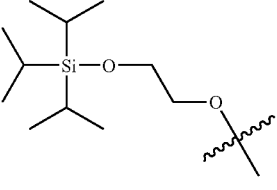
nn
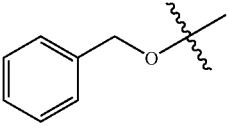
oo
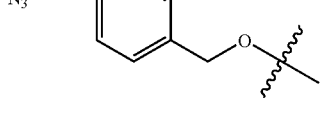
pp

TABLE 5-continued
Representative R[1] Groups
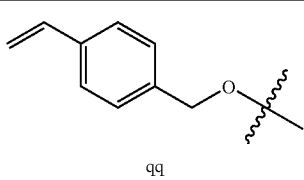
qq
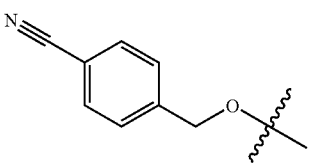
rr
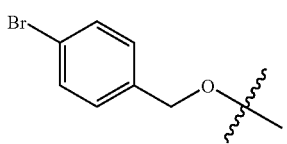
ss
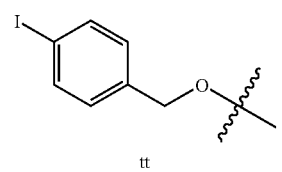
tt
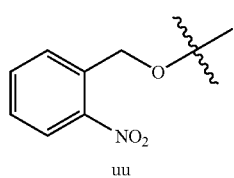
uu
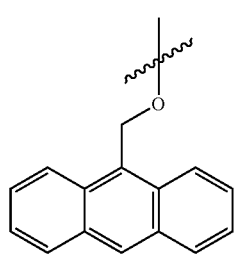
vv
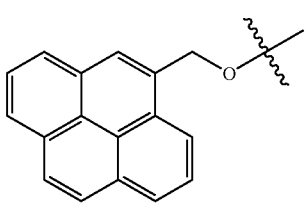
ww
TABLE 5-continued
Representative R[1] Groups
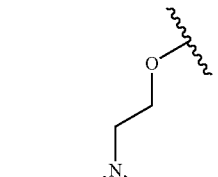
xx
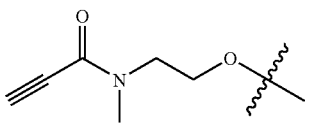
yy
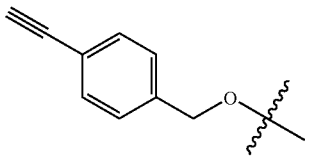
zz
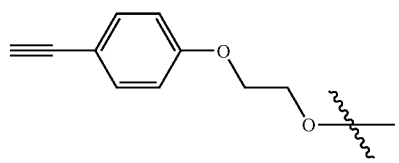
aaa
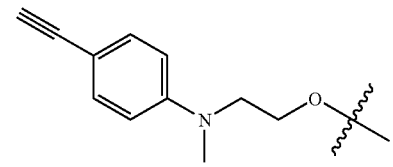
bbb
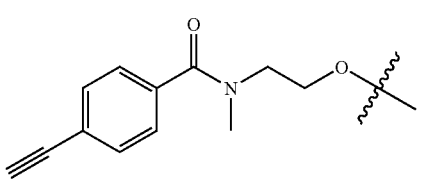
ccc
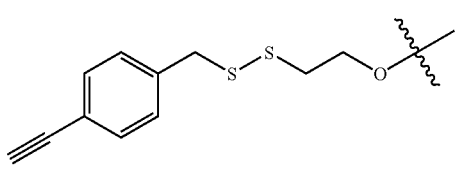
ddd TABLE 5-continued
Representative R¹ Groups
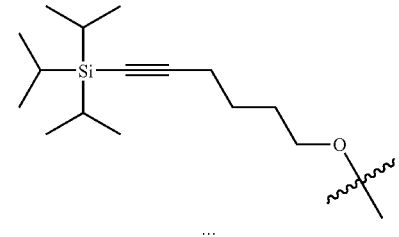
eee
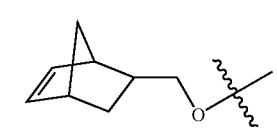
fff
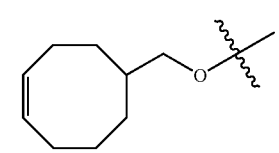
ggg
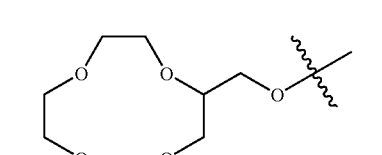
hhh
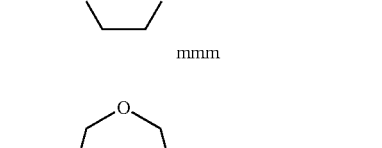
iii
TABLE 5-continued
Representative R¹ Groups
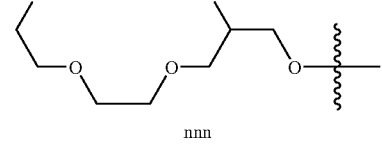
jjj
kkk
lll
mmm
nnn
ooo
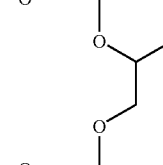
ppp TABLE 5-continued Representative R¹ Groups

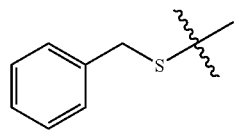
qqq

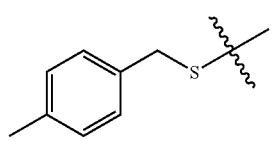
rrr

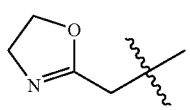
sss

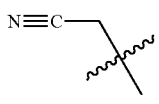
ttt

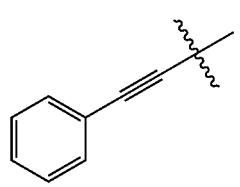
uuu

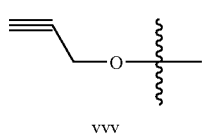
vvv

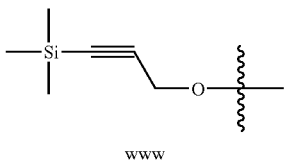
www

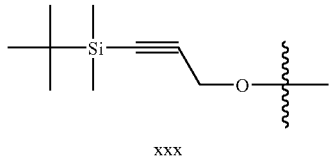
xxx

TABLE 5-continued

Representative R¹ Groups

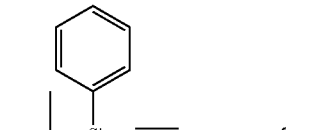
yyy

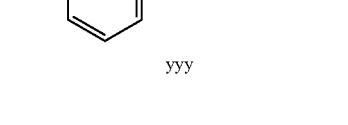
zzz

One of ordinary skill in the art would recognize that certain R¹ groups depicted in Table 5 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 5 are also contemplated. According to another embodiment, the R¹ group of any of formulae I, II, and III is selected from a deprotected group of Table 5.

Additional exemplary R¹ groups of any of formulae I, II, and III are set forth in Table 5a, below.

TABLE 5a

Representative R¹ Groups

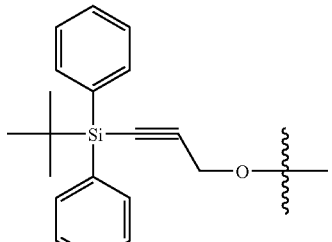

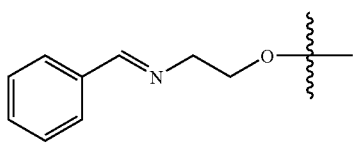

TABLE 5a-continued
Representative R¹ Groups
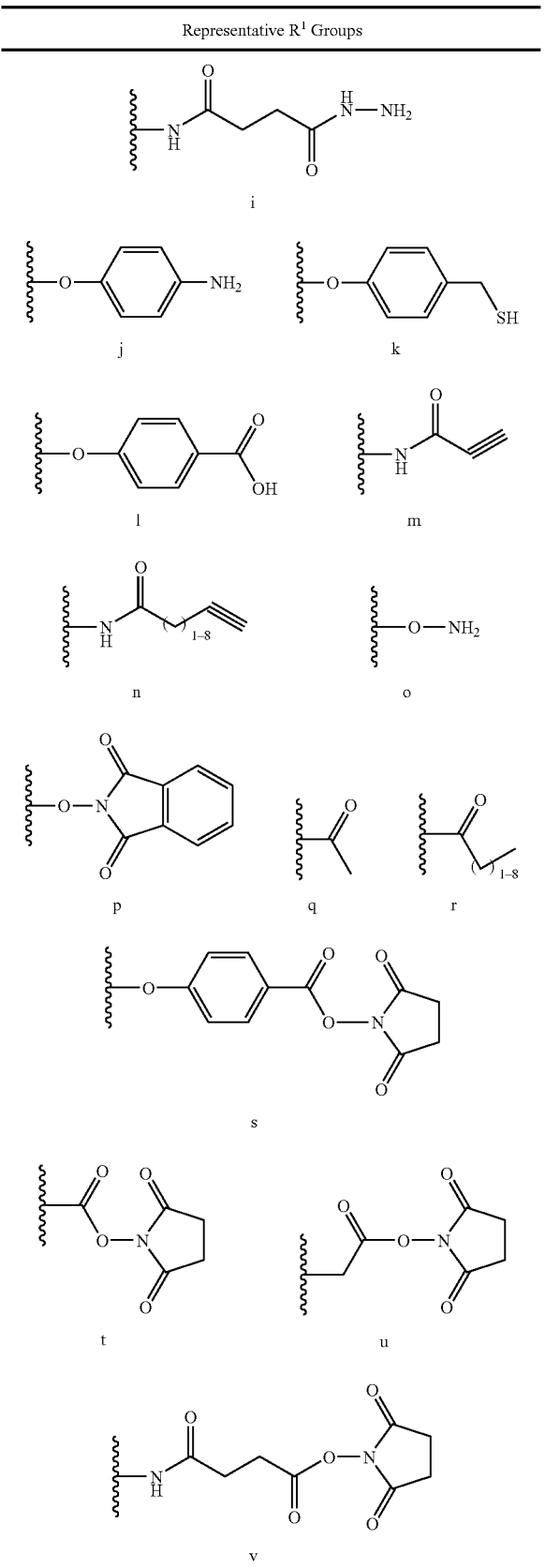
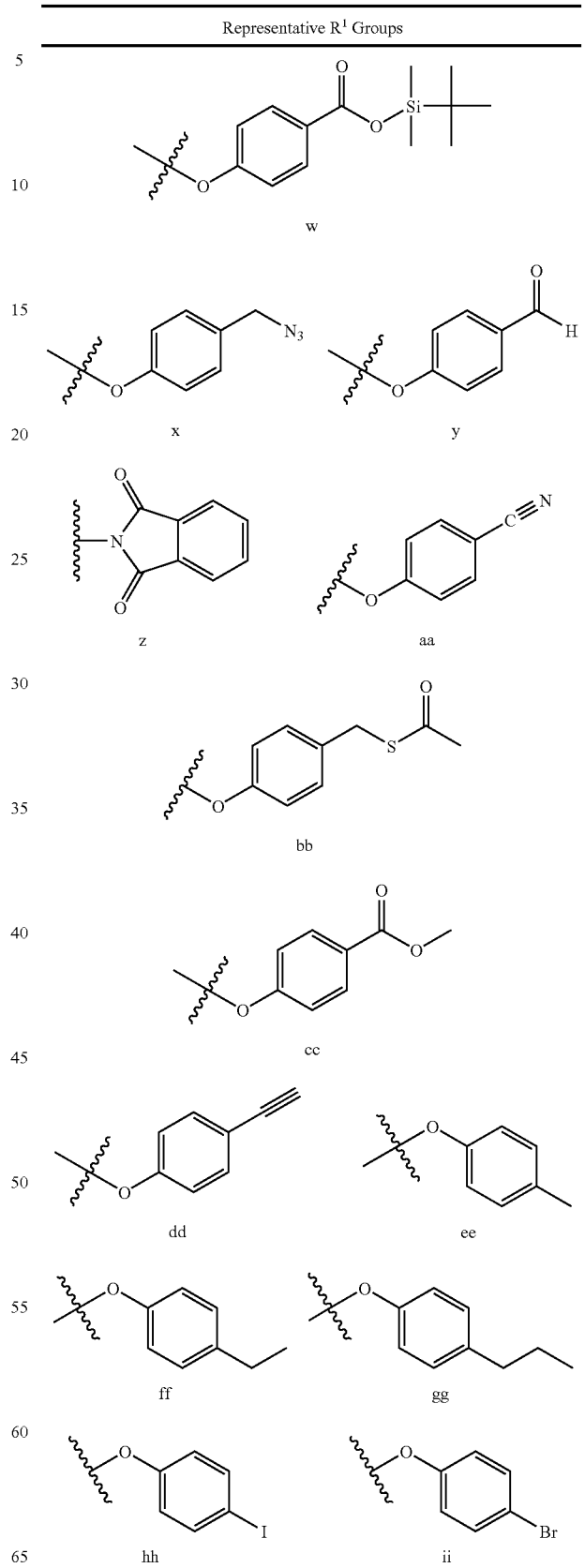

TABLE 5a-continued
Representative R¹ Groups
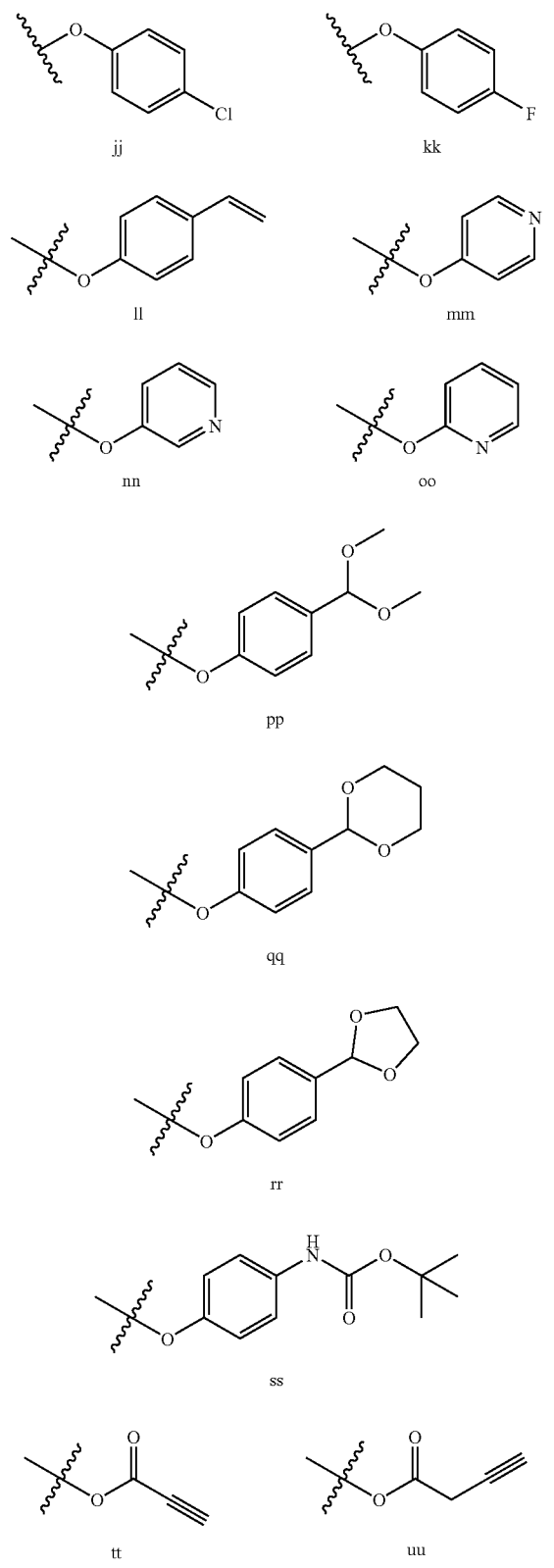
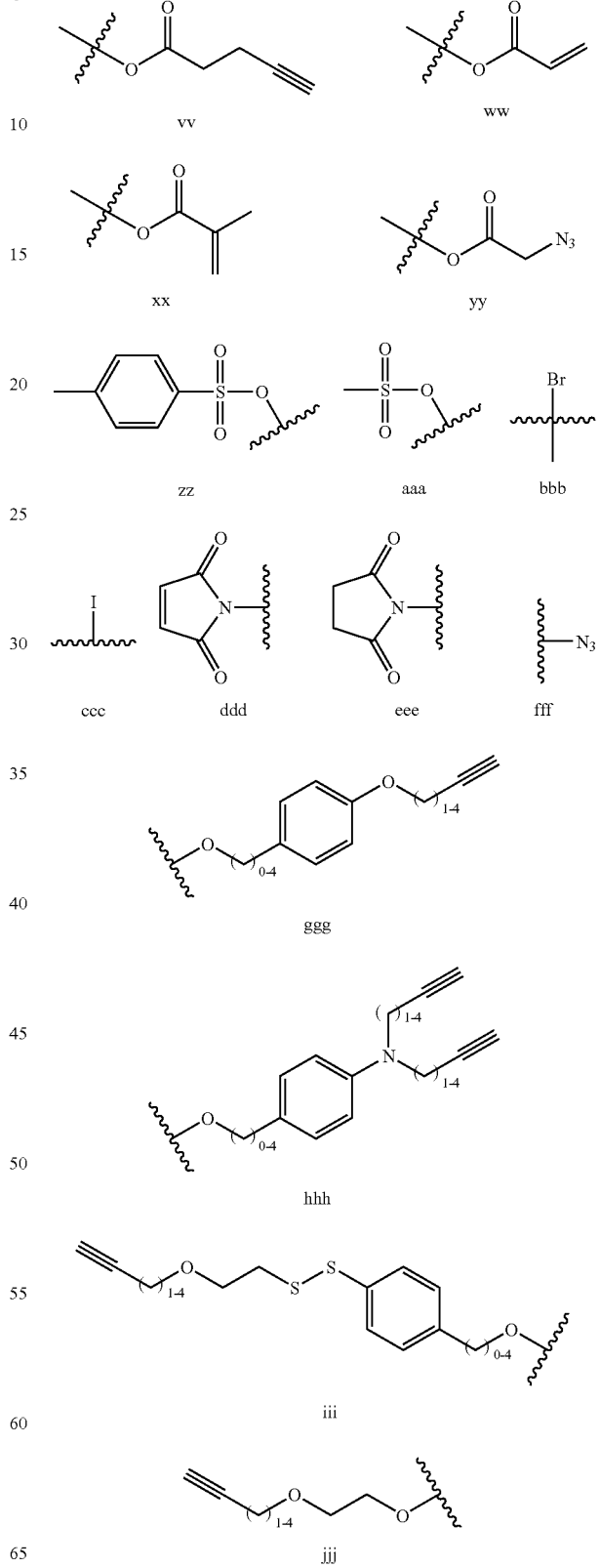

TABLE 5a-continued

Representative R¹ Groups

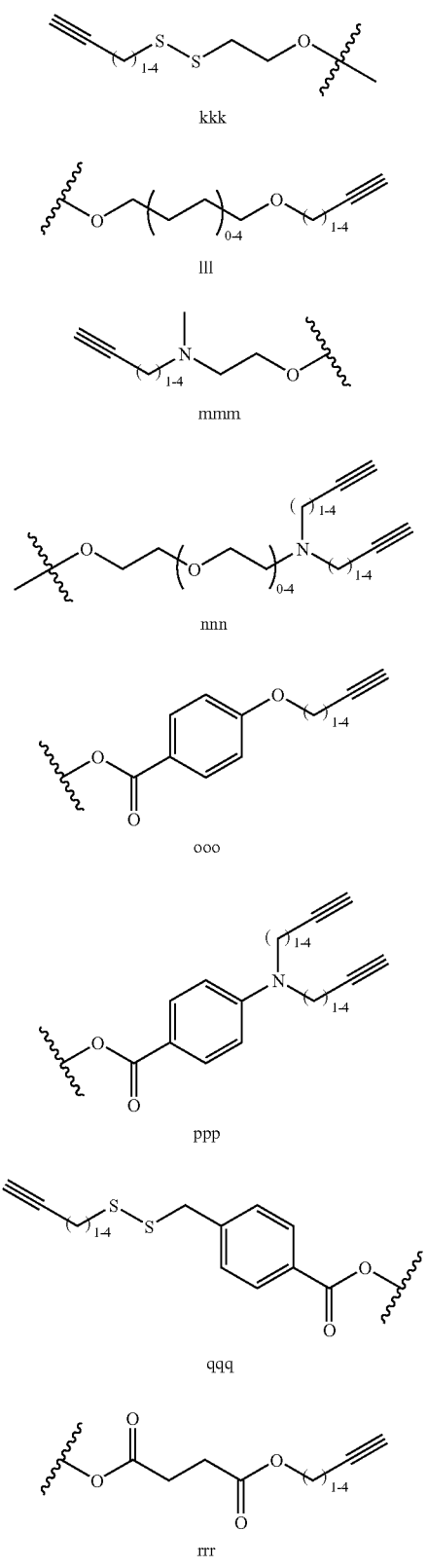

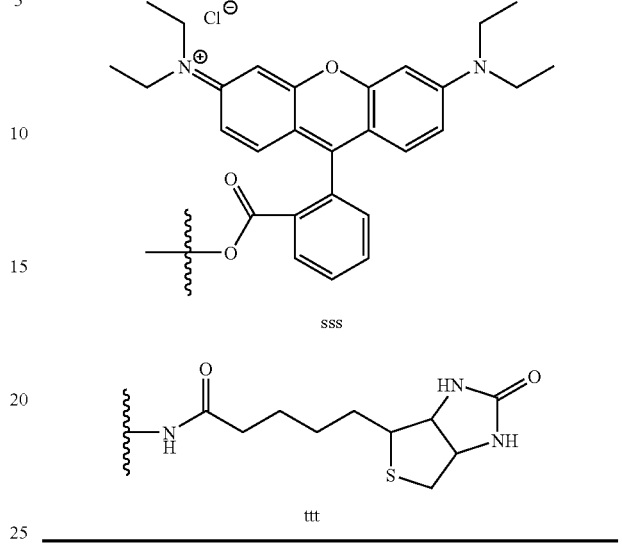

In certain embodiments, the R¹ group of any of formulae I, II, and III is selected from any of those R¹ groups depicted in Table 5, supra. In other embodiments, the R¹ group of any of formulae I, II, and III is group k or l. In yet other embodiments, the R¹ group of any of formulae I, II, and III is n, o, cc, dd, ee, ff, hh, h, ii, jj, ll, or uu. In still other embodiments, the R¹ group of any of formulae I, II, and III is h, aa, yy, zz, or aaa.

According to another aspect of the present invention, the R¹ group of any of formulae I, II, and III is q, r, s, t, www, xxx, or yy.

In other embodiments, the R¹ group of any of formulae I, II, and III is selected from any of those R¹ groups depicted in Tables 1-4, supra.

Exemplary $R^{2a}$ groups of any of formulae I, II, and III are set forth in Table 6, below.

TABLE 6

Representative $R^{2a}$ Groups

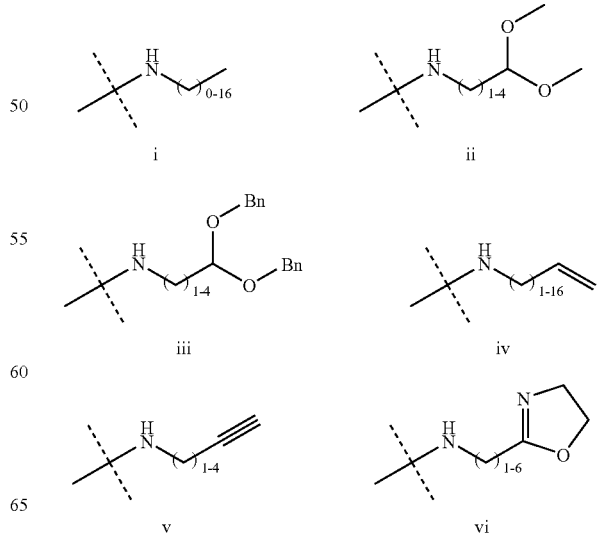

TABLE 6-continued
Representative $R^{2a}$ Groups
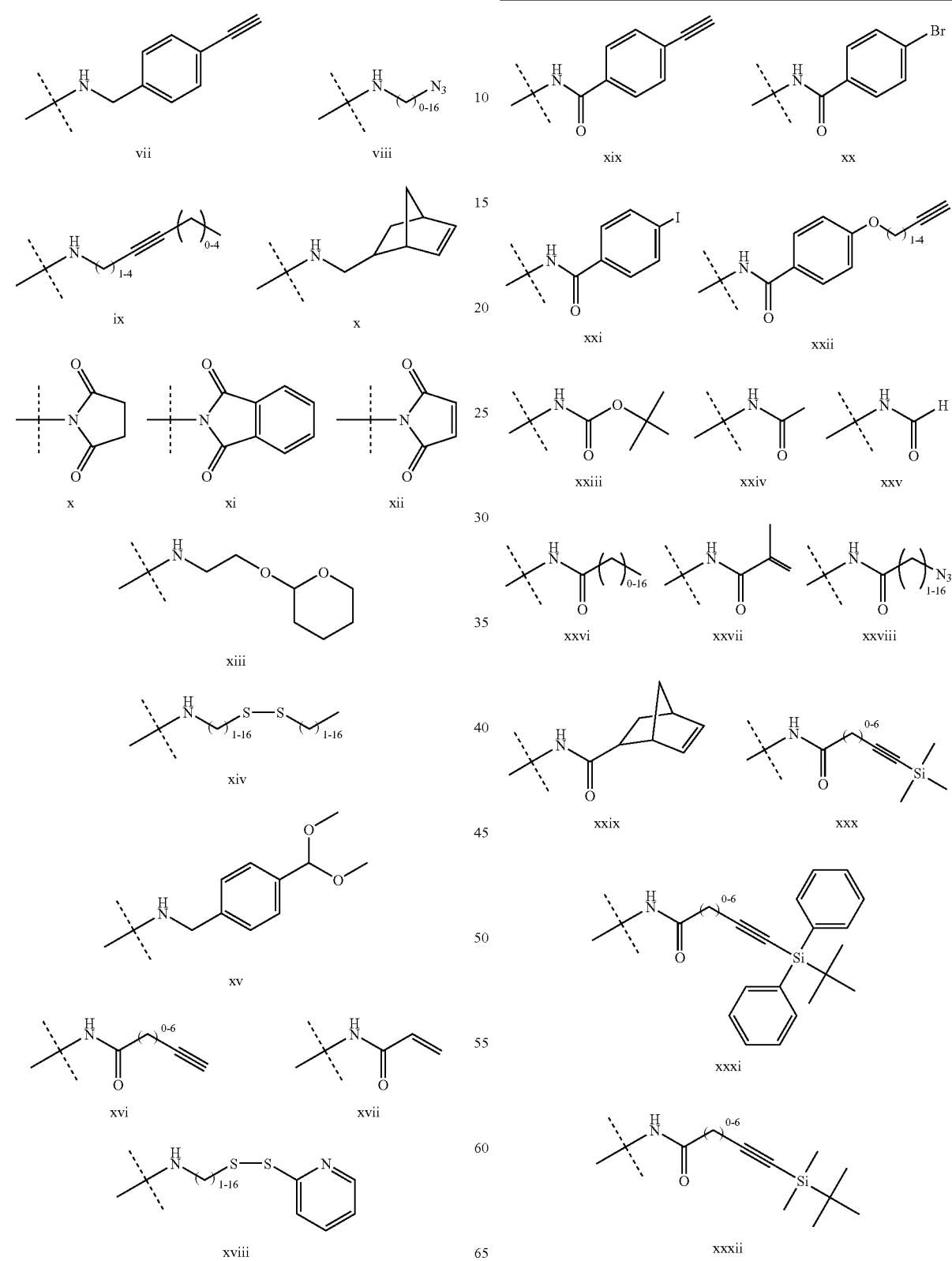

TABLE 6-continued

Representative $R^{2a}$ Groups

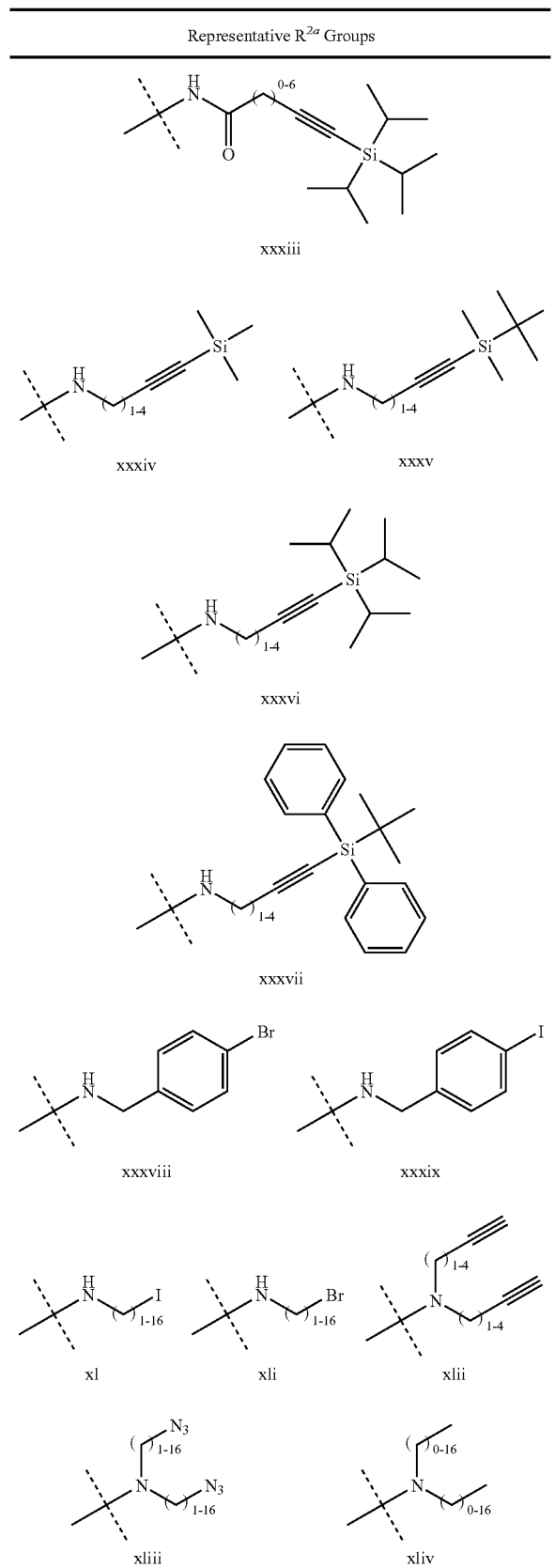

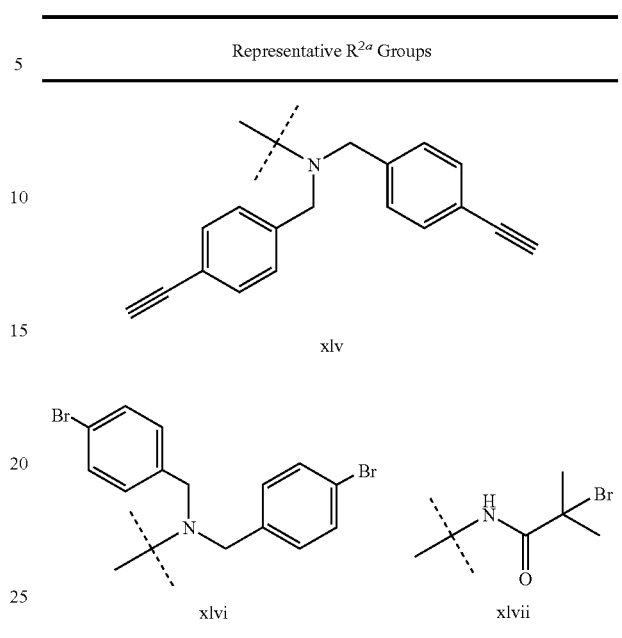

In certain embodiments, the $R^{2a}$ group of any of formulae I, II, and III is selected from any of those $R^{2a}$ groups depicted in Table 6, supra. In other embodiments, the $R^{2a}$ group of any of formulae I, II, and III is group v, viii, xvi, xix, xxii, xxx, xxxi, xxxii, xxxiii, xxxiv, xxxv, xxxvi, xxxvii, or xlii. In yet other embodiments, the $R^{2a}$ group of any of formulae I, II, and III is xv, xviii, xx, xxi, xxxviii, or xxxix. In certain embodiments, the $R^{2a}$ group of any of formulae I, II, and III is xxxiv.

According to another embodiment, the $R^{2a}$ group of any of formulae I, II, and III is selected from any of those $R^{2a}$ groups depicted in Tables 1-4, supra.

One of ordinary skill in the art would recognize that certain $R^{2a}$ groups depicted in Table 6 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 6 are also contemplated. According to another embodiment, the $R^{2a}$ group of any of formulae I, II, and III is selected from a deprotected group of Table 6.

C. Drug Loading

As described generally above, in certain embodiments the present invention provides a drug-loaded micelle comprising a multiblock copolymer which comprises a polymeric hydrophilic block, a crosslinked poly(amino acid) block, and a poly(amino acid block), characterized in that said micelle has a drug-loaded inner core, a crosslinked outer core, and a hydrophilic shell. As described herein, micelles of the present invention can be loaded with any hydrophobic or ionic therapeutic agent.

According to another embodiment, the present invention provides a drug-loaded micelle comprising a multiblock copolymer of formula I:

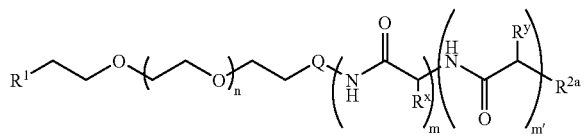

wherein:
n is 10-2500;
m is 1 to 1000;
m' is 1 to 1000;
$R^x$ is a natural or unnatural amino acid side-chain group that is capable of crosslinking;
$R^y$ is a hydrophobic or ionic, natural or unnatural amino acid side-chain group;
$R^1$ is $-Z(CH_2CH_2Y)_p(CH_2)_tR^3$, wherein:
  Z is —O—, —S—, —C≡C—, or —CH$_2$—;
  each Y is independently —O— or —S—;
  p is 0-10;
  t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments with respect to each of the $R^1$, $R^{2a}$, Q, $R^x$, $R^y$, n, m, and m' groups of formula I, are as described in various classes and subclasses, both singly and in combination, herein.

In certain embodiments, $R^x$ is a crosslinkable amino acid side-chain group and $R^y$ is a hydrophobic amino acid side-chain group. Such hydrophilic, or crosslinkable, amino acid side-chain groups include tyrosine, serine, cysteine, threonine, aspartic acid (also known as aspartate, when charged), glutamic acid (also known as glutamate, when charged), asparagine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH$_2$C(O)CH, an aspartic acid side-chain, —CH$_2$CH$_2$C(O)OH, a cystein side-chain, —CH$_2$SH, a serine side-chain, —CH$_2$OH, an aldehyde containing side-chain, —CH$_2$C(O)H, a lysine side-chain, —(CH$_2$)$_4$NH$_2$, an arginine side-chain, —(CH$_2$)$_3$NHC(=NH)NH$_2$, a histidine side-chain, —CH$_2$-imidazol-4-yl.

As defined generally above, the $R^{2a}$ group of formula I is a mono-protected amine, a di-protected amine, —NHR$^4$, —N(R$^4$)$_2$, —NHC(O)R$^4$, —NR$^4$C(O)R$^4$, —NHC(O)NHR$^4$, —NHC(O)N(R$^4$)$_2$, —NR$^4$C(O)NHR$^4$, —NR$^4$C(O)N(R$^4$)$_2$, —NHC(O)OR$^4$, —NR$^4$C(O)OR$^4$, —NHSO$_2$R$^4$, or —NR$^4$SO$_2$R$^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

One of ordinary skill in the art will recognize that the $R^{2a}$ moiety can interact with the encapsulated drug. In certain embodiments, the $R^{2a}$ moiety is hydrophobic when the encapsulated drug is hydrophobic. Such hydrophobic $R^{2a}$ groups include linear and branched alkanes. In other embodiments, the $R^{2a}$ moiety is ionic when the encapsulated drug is ionic. Such ionic $R^{2a}$ groups include alkyl amines when the encapsulated drug is a cationic therapeutic (i.e. DNA and RNA therapeutics, oligopeptide and protein therapeutics). Other ionic $R^{2a}$ groups include alkyl carboxylic, sulfonic, and phosponic acids when the encapsulated drug is an anionic therapeutic (i.e. oligopeptide and protein therapeutics).

The accomodation of structurally diverse therapeutic agents within a micelle of the present invention is effected by adjusting the poly(amino acid) block, i.e., the block comprising $R^y$. For example, when $R^y$ is a hydrophobic natural or unnatural amino acid side-chain, micelles of the present invention are useful for encapsulating hydrophobic therapeutic agents.

In certain embodiments, micelles of the present invention are loaded with a hydrophobic drug. In accordance with such embodiments, $R^y$ is a natural or unnatural hydrophobic amino acid side-chain group. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates, or mixtures thereof. One of ordinary skill in the art would recognize that protection of a polar or hydrophilic amino acid side-chain can render that amino acid non-polar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^y$ are as described herein.

In other embodiments, the $R^y$ group of formula I comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

Hydrophobic small molecule drugs suitable for loading into micelles of the present invention are well known in the art. In certain embodiments, the present invention provides a drug-loaded micelle as described herein, wherein the drug is a hydrophobic drug selected from those described herein, infra.

In other embodiments, when the $R^y$ group of formula I is an ionic natural or unnatural amino acid side-chain, micelles of the present invention are useful for encapsulating ionic, or charged, therapeutic agents. Exemplary ionic $R^y$ moieites include polylysine, polyarginine, poly aspartic acid, polyhistidine, and polyglutamic acid.

Exemplary ionic, or charged, therapeutic agents include DNA plasmids, short interfering RNAs (siRNAs), micro RNAs (miRNAs), short hairpin RNAs (shRNAs), antisense RNAs, and other RNA-based therapeutics. Other ionic, or charged, therapeutic agents include oligopeptides, peptides, monoclonal antibodies, cytokines, and other protein therapeutics.

In other embodiments, the present invention provides a drug-loaded micelle comprising a multiblock copolymer of formula II:

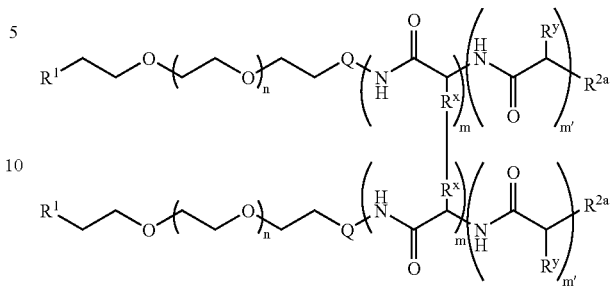

wherein:
n is 10-2500;
m is 1 to 1000;
m' is 1 to 1000;
$R^x$ is a natural or unnatural amino acid side-chain group that is crosslinked;
$R^y$ is a hydrophobic or ionic, natural or unnatural amino acid side-chain group;
$R^1$ is $-Z(CH_2CH_2Y)_p(CH_2)_tR^3$, wherein:
  Z is —O—, —S—, —C≡C—, or —CH$_2$—;
  each Y is independently —O— or —S—;
  p is 0-10;
  t is 010; and
$R^3$ is —N$_3$, —CN, a mono-protected amine, a di-protected amine, a protected aldehyde, a protected hydroxyl, a protected carboxylic acid, a protected thiol, a 9-30-membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, $-N(R^4)_2$, $-NR^4C(O)R^4$, $-NR^4C(O)N(R^4)_2$, $-NR^4C(O)OR^4$, or $-NR^4SO_2R^4$; and
each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:

two R⁴ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments with respect to each of the $R^1$, $R^{2a}$, Q, $R^x$, $R^y$, n, m, and m' groups of formula II, are as described in various classes and subclasses, both singly and in combination, herein.

In certain embodiments, $R^x$ is a crosslinked amino acid side-chain group and $R^y$ is a hydrophobic amino acid side-chain group. Such hydrophilic, or crosslinkable, amino acid side-chain groups include tyrosine, serine, cysteine, threonine, aspartic acid (also known as aspartate, when charged), glutamic acid (also known as glutamate, when charged), asparagine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a crosslinked natural or unnatural amino acid side-chain group. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH₂C(O)CH, an aspartic acid side-chain, —CH₂CH₂C(O)OH, a cystein side-chain, —CH₂SH, a serine side-chain, —CH₂OH, an aldehyde containing side-chain, —CH₂C(O)H, a lysine side-chain, —(CH₂)₄NH₂, an arginine side-chain, —(CH₂)₃NHC(=NH)NH₂, a histidine side-chain, —CH₂-imidazol-4-yl.

In still other embodiments, the present invention provides a drug-loaded micelle comprising a multiblock copolymer of formula III:

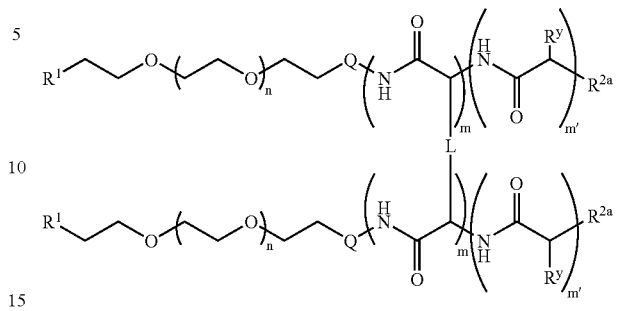

wherein:
n is 10-2500;
m is 1 to 1000;
m' is 1 to 1000;
L is a bivalent, saturated or unsaturated, straight or branched $C_{1-12}$ alkylene chain, wherein 0-6 methylene units of L are independently replaced by -M-, -Cy-, —O—, —NH—, —S—, —OC(O)—, —C(O)O—, —C(O)—, —SO—, —SO—, —NHSO₂—, —SO₂NH—, —NHC(O)—, —C(O)NH—, —OC(O)NH—, or —NHC(O)O—, wherein:
-M- is a suitable bivalent metal;
-Cy- is an optionally substituted 5-8 membered bivalent, saturated, partially unsaturated, or aryl ring having 0-4 heteroatoms independently selected from nitrogen, oxygen, or suflfur, or an optionally substituted 8-10 membered bivalent saturated, partially unsaturated, or aryl bicyclic ring having 0-5 heteroatoms independently selected from nitrogen, oxygen, or suflfur;
$R^y$ is a hydrophobic or ionic, natural or unnatural amino acid side-chain group;
$R^1$ is -Z(CH₂CH₂Y)$_p$(CH₂)$_t$R³, wherein:
Z is —O—, —S—, —C≡C—, or —CH₂—;
each Y is independently —O— or —S—;
p is 0-10;
t is 0-10; and
$R^3$ is —N₃, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO₂—, —NHSO₂—, —SO₂NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments with respect to each of the $R^1$, $R^{2a}$, L, Q, $R^y$, n, m, and m' groups of formula III, are as described in various classes and subclasses, both singly and in combination, herein.

In certain embodiments, $R^y$ is a hydrophobic amino acid side-chain group. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol functional groups of $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

In certain embodiments, micelles of the present invention are loaded with a hydrophobic drug. In accordance with such embodiments, the $R^y$ group of formula III is a natural or unnatural hydrophobic amino acid side-chain group. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates, or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^y$ are as described herein.

In certain embodiments, the $R^y$ group of formula III comprises a mixture of hydrophobic and hydrophilic amino acid side-chain groups such that the overall poly(amino acid) block comprising $R^y$ is hydrophobic. In other embodiments, $R^y$ comprises a mixture of phenylalanine and tyrosine. By way of example, this particular copolymer is used to encapsulate one or more of DOX, CPT, and paclitaxel in the hydrophobic phenylalanine/tyrosine inner core. Although only sparingly soluble in water, these drugs possess polar functionalities (e.g. amine, alcohol, and phenols), which makes the incorporation of tyrosine, a polar amino acid, advantageous for effective encapsulation. By utilizing this particular core composition, relatively high DOX, CPT, and paclitaxel loadings are achieved. In certain embodiments, the present invention provides a micelle comprising a compound of formula III characterized in that DOX, CPT, and paclitaxel are encapsulated in the hydrophobic phenylalanine/tyrosine inner core and the poly(aspartic acid) outer core is crosslinked with zinc. In certain embodiments, m and m' add up to about 30 to about 60. In still other embodiments, m' is 1-20 repeat units and m' is 10-50 repeat units. In certain embodiments, the phenylalanine/tyrosine ratio of m' is 4:1. In other embodiments the phenylalanine/tyrosine ratio of m' is 9:1. In still other embodiments, the phenylalanine/tyrosine ratio of m' is 3:1. In other embodiments, $R^y$ comprises 4-8 tyrosine repeat units and 20-32 phenylalanine. In still other embodiments, $R^y$ comprises 2-40 tyrosine and 10-100 phenylalanine repeat units.

Hydrophobic small molecule drugs suitable for loading into micelles of the present invention are well known in the art. In certain embodiments, the present invention provides a drug-loaded micelle as described herein, wherein the drug is a hydrophobic drug selected from analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

In other embodiments, the hydrophobic drug is selected from one or more analgesics, anti-bacterial agents, anti-viral agents, anti-inflammatory agents, anti-depressants, anti-diabetics, anti-epileptics, anti-hypertensive agents, anti-migraine agents, immunosuppressants, anxiolytic agents, sedatives, hypnotics, neuroleptics, β-blockers, gastro-intestinal agents, lipid regulating agents, anti-anginal agents, Cox-2 inhibitors, leukotriene inhibitors, macrolides, muscle relaxants, opioid analgesics, protease inhibitors, sex hormones, cognition enhancers, anti-urinary incontinence agents, and mixtures thereof.

According to one aspect, the present invention provides a micelle, as described herein, loaded with a hydrophobic drug selected from any one or more of acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, essential fatty acid sources, etodolac, etoposide, famotidine, fenofibrate, fentanyl, fexofenadine, fmasteride, fluconazole, flurbiprofen, fluvastatin, fosphenyloin, frovatriptan, furazolidoneu, gabapentin, gemfibrozil, glibenclamide, glipizide, glyburide, glimepiride, griseoulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfmavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

According to another embodiment, the present invention provides a micelle, as described herein, loaded with a hydrophobic antiproliferative or chemotherapeutic drug. One of ordinary skill in the art will appreciate that many anticancer agents are hydrophobic. In certain embodiments, the hydrophobic antiproliferative or chemotherapeutic drug is selected from any one or more of a taxane (e.g., paclitaxel), vincristine, adriamycin, vinca alkaloids (e.g., vinblastine), anthracyclines (e.g., doxoribicin), epipodophyllotoxins (e.g., etoposide), cisplatin, methotrexate, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, and metronidazole, among others.

In certain embodiments, the present invention provides a micelle, as described herein, loaded with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, hrinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

According to another embodiment, the present invention provides a micelle, as described herein, loaded with a treatment for Alzheimer's Disease such as Aricept® or Excelon®; a treatment for Parkinson's Disease such as L-DOPA/carbidopa, entacapone, ropinrole, pramipexole, bromocriptine, pergolide, trihexephendyl, or amantadine; an agent for treating Multiple Sclerosis (MS) such as beta interferon (e.g., Avonex® and Rebif®), Copaxone®, or mitoxantrone; a treatment for asthma such as a steroid, albuterol or Singulair®; an agent for treating schizophrenia such as zyprexa, risperdal, seroquel, or haloperidol; an anti-inflammatory agent such as corticosteroids, TNF blockers, IL-1 RA, azathioprine, cyclophosphamide, or sulfasalazine; an immunomodulatory and immunosuppressive agent such as cyclosporin, tacrolimus, rapamycin, mycophenolate mofetil, interferons, corticosteroids, cyclophophamide, azathioprine, or sulfasalazine; a neurotrophic factor such as acetylcholinesterase inhibitors, MAO inhibitors, interferons, anti-convulsants, ion channel blockers, riluzole, or anti-Parkinsonian agents; an agent for treating cardiovascular disease such as beta-blockers, ACE inhibitors, diuretics, nitrates, calcium channel blockers, or statins; an agent for treating liver disease such as corticosteroids, cholestyramine, interferons, or anti-viral agents; an agent for treating blood disorders such as corticosteroids, anti-leukemic agents, or growth factors; and an agent for treating immunodeficiency disorders such as gamma globulin.

In other embodiments, when the $R^y$ group of formula III is an ionic natural or unnatural amino acid side-chain, micelles of the present invention are useful for encapsulating ionic, or charged, therapeutic agents. Exemplary ionic $R^y$ moieites include polylysine, polyarginine, poly aspartic acid, polyhistidine, and polyglutamic acid.

Exemplary ionic, or charged, therapeutic agents include DNA plasmids, short interfering RNAs (siRNAs), micro RNAs (miRNAs), short hairpin RNAs (shRNAs), antisense RNAs, and other RNA-based therapeutics. Other ionic, or charged, therapeutic agents include oligopeptides, peptides, monoclonal antibodies, cytokines, and other protein therapeutics.

Targeting the delivery of potent, cytotoxic agents specifically to cancer cells using responsive nanovectors would have a clear impact on the well-being of the many thousands of people who rely on traditional small molecule therapeutics for the treatment of cancer. In certain embodiments, the present invention provides micelle-encapsulated forms of the common chemotherapy drugs, doxorubicin (adriamycin), a topoisomerase II inhibitor, camptothecin (CPT), a topoisomerase I inhibitor, or paclitaxel (Taxol), an inhibitor of microtubule assembly. These drugs are both effective chemotherapy agents but suffer from clinical problems which are effectively addressed by cancer-specific delivery. For example, the cytotoxic nature of these drugs affects tumors and healthy tissue alike, resulting in a multitude of side effects such as dermatitis, hair loss, and nausea. DOX side effects such as acute cardiotoxicity and bone marrow suppression are particularly problematic. Neutral doxorubicin, camptothecin, and paclitaxel are poorly soluble in water (i.e., hydrophobic), making them candidates for micellar delivery. Camptothecin, which possesses a hydrolytically degradable lactone ring, has a short half-life in aqueous solution, especially at elevated pH. Without wishing to be bound by any particular theory, it is believed that encapsulation in the hydrophobic micelle core will significantly increase the half-life of the drug. A multitude of drug delivery systems have been employed to reduce the aforementioned problems associated with doxorubicin, camptothecin, and paclitaxel, with varying degrees of success.

D. Polymer Conjugation

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. *Vector. Gene Ther.* 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.,; Weinberg, B. D. P., J.; Boothman, D. A.; Gao, J. *Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J.* 2001, 356, 867-873; Kurschus, F. C.; Kleinschmidt, M.; Fellows, E.; Dornmair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

Compounds of any of formulae I, II, and III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of any of formulae I, II, and III to a macromolecule via Click chemistry. Yet another embodiment of the present invention provides a macromolecule conjugated to a compound of any of formulae I, II, and III via the $R^1$ group.

After incorporating the poly (amino acid) block portions into the multi-block coploymer of the present invention resulting in a multi-block copolymer of the form W—X—X', the other end-group functionality, corresponding to the $R^1$ moiety of any of formulae I, II, and III, can be used to attach targeting groups for cell specific delivery including, but not limited to, attach targeting groups for cell specific delivery including, but not limited to, proteins, oliogopeptides, antibodies, monosaccharides, oligosaccharides, vitamins, or other small biomolecules. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopedptides), and vitamins (e.g. folate). Alternatively, the $R^1$ moiety of any of formulae I, II, and III is bonded to a biomolecule, drug, cell, or other suitable substrate.

In other embodiments, the $R^1$ moiety of any of formulae I, II, and III is bonded to biomolecules which promote cell entry and/or endosomal escape. Such biomolecules include, but are not limited to, oligopeptides containing protein transduction domains such as the HIV Tat peptide sequence (GRKKRRQRRR) or oligoarginine (RRRRRRRRR). Oligopeptides which undergo conformational changes in varying pH environments such oligohistidine (HHHHH) also promote cell entry and endosomal escape.

In other embodiments, the $R^1$ moiety of any of formulae I, II, and III is bonded to detectable moieties, such as fluorescent dyes or labels for positron emission tomography including molecules containing radioisotopes (e.g. $^{18}F$) or ligands with bound radioactive metals (e.g. $^{62}Cu$). In other embodiments, the $R^1$ moiety of any of formulae I, II, and III is bonded to a contrast agents for magnetic resonance imaging such as gadolinium, gadolinium chelates, or iron oxide (e.g $Fe_3O_4$ and $Fe_2O_3$) particles. In other embodiments, the $R^1$ moiety of any of formulae I, II, and III is bonded to a semiconducting nanoparticle such as cadmium selenide, cadmium sulfide, or cadmium telluride or bonded to other metal nanoparticles such as colloidal gold. In other embodiments, the $R^1$ moiety of any of formulae I, II, and III is bonded to natural or synthetic surfaces, cells, viruses, dyes, drugs, chelating agents, or used for incorporation into hydrogels or other tissue scaffolds.

In one embodiment, the $R^1$ moiety of any of formulae I, II, and III is an acetylene or an acetylene derivative which is capable of undergoing [3+2] cycloaddition reactions with complementary azide-bearing molecules and biomolecules. In another embodiment, the $R^1$ moiety of any of formulae I, II, and III is an azide or an azide derivative which is capable of undergoing [3+2] cycloaddition reactions with complementary alkyne-bearing molecules and biomolecules (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukheiji, M.; Chin, J. W.; Anderson, C.; Schultz, P. G. *J. Am. Chem. Soc.* 2003, 125, 11782-11783.

In another embodiment, the [3+2] cycloaddition reaction of azide or acetylene-bearing nanovectors and complimentary azide or acetylene-bearing biomolecules are transition metal catalyzed. Copper-containing molecules which catalyze the "click" reaction include, but are not limited to, copper bromide (CuBr), copper chloride (CuCl), copper sulfate ($CuSO_4$), copper iodide (CuI), $[Cu(MeCN)_4](OTf)$, and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In another embodiment, the $R^1$ moiety of any of formulae I, II, and III is an hydrazine or hydrazide derivative which is capable of undergoing reaction with biomolecules containing aldehydes or ketones to form hydrazone linkages. In another embodiment, the $R^1$ moiety of any of formulae I, II, and III is an aldehyde or ketone derivative which is capable of undergoing reaction with biomolecules containing a hydrazine or hydrazide derivative to form hydrazone linkages.

In another embodiment, the $R^1$ moiety of any of formulae I, II, and III is a hydroxylamine derivative which is capable of undergoing reaction with biomolecules containing aldehydes or ketones. In another embodiment, the $R^1$ moiety of any of formulae I, II, and III is an aldehyde or ketone which is capable of undergoing reaction with biomolecules containing a hydroxylamine, or a hydroxylamine derivative.

In yet another embodiment, the $R^1$ moiety of any of formulae I, II, and III is an aldehyde or ketone derivative which is capable of undergoing reaction with biomolecules containing primary or secondary amines to form imine linkages. In another embodiment, the $R^1$ moiety of any of formulae I, II, and III is a primary or secondary amine which is capable of undergoing reaction with biomolecules containing an aldehyde or ketone functionality to form imine linkages. It will be appreciated that imine linkages can be further converted to stable amine linkages by treatment with a suitable reducing agent (e.g. lithium aluminum hydride, sodium borohydride, sodium cyanoborohydride, etc.)

In yet another embodiment, the $R^1$ moiety of any of formulae I, II, and III is an amine (primary or secondary) or alcohol which is capable of undergoing reaction with biomolecules containing activated esters (e.g. 4-nitrophenol ester, N-hydroxysuccinimide, pentafluorophenyl ester, ortho-pyridylthioester), to form amide or ester linkages. In still other embodiments, the $R^1$ moiety of any of formulae I, II, and III is an activated ester which is capable of undergoing reaction with biomolecules possessing amine (primary or secondary) or alcohols to form amide or ester linkages.

In still other embodiments, the $R^1$ moiety of any of formulae I, II, and III is an amine or alcohol which is bound to biomolecules with carboxylic acid functionality using a suitable coupling agent. In still other embodiments, the $R^1$ moiety of any of formulae I, II, and III is a carboxylic acid functionality which is bound to biomolecules containing amine or alcohol functionality using a suitable coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, the $R^1$ moiety of any of formulae I, II, and III is an electrophile such as maleimide, a maleimide derivative, or a bromoacetamide derivative, which is capable of reaction with biomolecules containing thiols or amines. In another embodiment, the $R^1$ moiety of any of formulae I, II, and III is a nucleophile such as an amine or thiol which is capable or reaction with biomolecules containing electrophilic functionality such as maleimide, a maleimide derivative, or a bromoacetamide derivative.

In still other embodiments, the $R^1$ moiety of any of formulae I, II, and III is a orthopyridyl disulfide moiety which undergoes disulfide exchange with biomolecules containing thiol functionality. In still other embodiments, the $R^1$ moiety of any of formulae I, II, and III is a thiol or thiol derivative which undergoes disulfide exchange with biomolecules containing orthopyridyl disulfide functionality. It will be appreciated that such exchange reactions result in a disulfide linkage which is reversible in the presence of a suitable reducing agent (e.g. glutathione, dithiothreitol (DTT), etc.).

In certain embodiments, micelles of the present invention are mixed micelles comprising one or more compounds of formula I, II, or III. It will be appreciated that mixed micelles having different $R^1$ groups, as described herein, can be conjugated to multiple other compounds and/or macromolecules. For example, a mixed micelle of the present invention can have one $R^1$ group suitable for Click chemistry and another $R^1$ group suitable for covalent attachment via a variety of coupling reacions. Such a mixed micelle can be conjugated to different compounds and/or macromolecules via these different $R^1$ groups. Such conjugation reactions are well known to one of ordinary skill in the art and include those described herein.

4. General Methods for Providing Compounds of the Present Invention

Multiblock copolymers of the present invention are prepared by methods known to one of ordinary skill in the art and those described in detail in U.S. patent application Ser. No. 11/325,020 filed Jan. 4, 2006, the entirety of which is hereby incorporated herein by reference. Generally, such multiblock copolymers are prepared by sequentially polymerizing one or more cyclic amino acid monomers onto a hydrophilic polymer having a terminal amine salt wherein said polymerization is initiated by said amine salt. In certain embodiments, said polymerization occurs by ring-opening polymerization of the cyclic amino acid monomers. In other embodiments, the cyclic amino acid monomer is an amino acid NCA, lactam, or imide.

Scheme 2

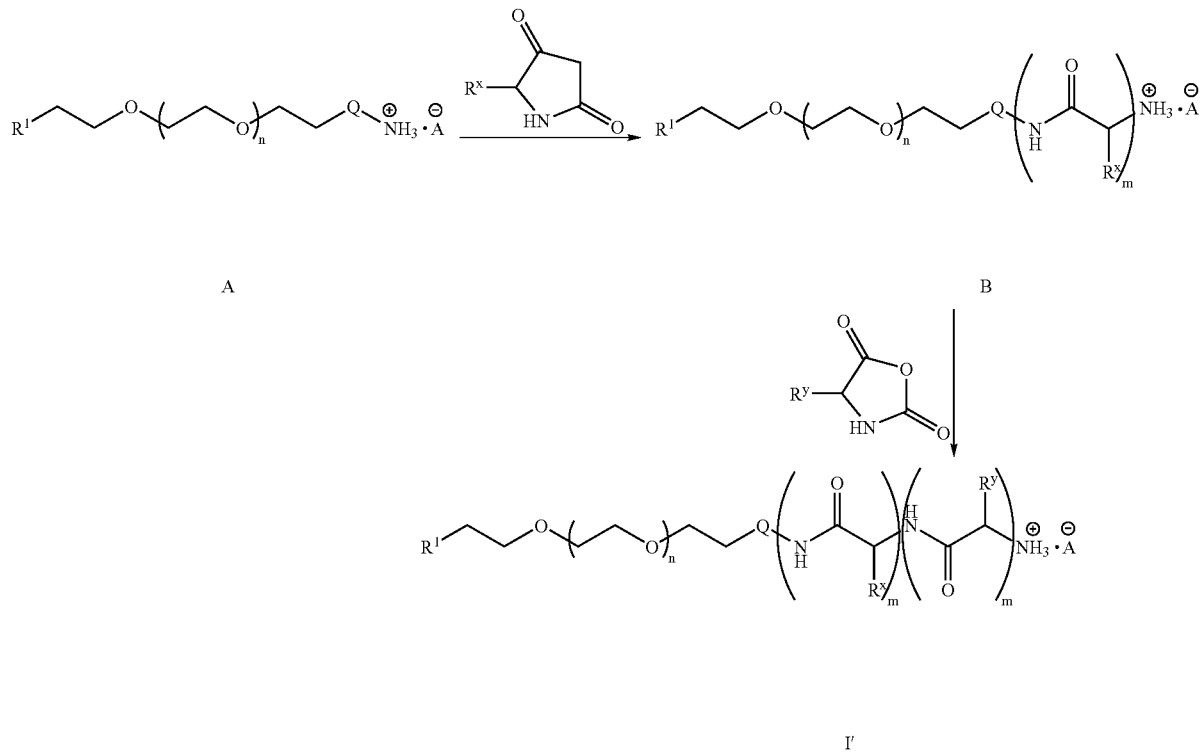

I'

Scheme 2 above depicts a general method for preparing multiblock polymers of the present invention. A macroinitiator of formula A is treated with a first amino acid NCA to form a compound of formula B having a first amino acid block. The second amino acid NCA is added to the living polymer of formula B to form a compound of formula I' having two differing amino acid blocks. Each of the $R^1$, A, n, Q, $R^x$, $R^y$, m, and m' groups depicted in Scheme 2 are as defined and described in classes and subclasses, singly and in combination, herein.

One step in the preparation of a compound of formula I comprises terminating the living polymer chain-end of the compound of formula I' with a suitable polymerization terminator to afford a compound of formula I. One of ordinary skill in the art would recognize that the polymerization terminator provides the $R^{2a}$ group of formula I. Accordingly, embodiments directed to the $R^{2a}$ group of formula I as set forth above and herein, are also directed to the suitable polymerization terminator itself, and similarly, embodiments directed to the suitable polymerization terminator, as set forth above and herein, are also directed to the $R^{2a}$ group of formula I.

As described above, compounds of formula I are prepared from compounds of formula I' by treatment with a suitable terminating agent. One of ordinary skill in the art would recognize that compounds of formula I are also readily prepared directly from compounds of formula I'. In such cases, and in certain embodiments, the compound of formula I' is treated with a base to form the freebase compound prior to, or concurrent with, treatment with the suitable terminating agent. For example, it is contemplated that a compound of formula I' is treated with a base and suitable terminating agent in the same reaction to form a freebase of that compound. In such cases, it is also contemplated that the base may also serve as the reaction medium.

One of ordinary skill in the art would also recognize that the above method for preparing a compound of formula I may be performed as a "one-pot" synthesis of compounds of formula I that utilizes the living polymer chain-end to incorporate the $R^2$ group of formula I. Alternatively, compounds of formula I may also be prepared in a multi-step fashion. For example, the living polymer chain-end of a compound of formula I' may be quenched to afford an amino group which may then be further derivatized, according to known methods, to afford a compound of formula I.

One of ordinary skill in the art will recognize that a variety of polymerization terminating agents are suitable for the present invention. Such polymerization terminating agents include any $R^{2a}$-containing group capable of reacting with the living polymer chain-end of a compound of formula I', or the free-based amino group of formula I', to afford a compound of formula I. Thus, polymerization terminating agents include anhydrides, and other acylating agents, and groups that contain a suitable leaving group LG that is subject to nucleophilic displacement.

Alternatively, compounds of formula I' may be coupled to carboxylic acid-containing groups to form an amide thereof. Thus, it is contemplated that the amine group of formula I' or freease thereof, may be coupled with a carboxylic acid moiety to afford compounds of formula I wherein $R^{2a}$ is —NHC(O)$R^4$. Such coupling reactions are well known in the art. In certain embodiments, the coupling is achieved with a suitable coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, 5$^{th}$ Ed., pp. 351-357, John Wiley and Sons, N.Y.

A "suitable leaving group that is subject to nucleophilic displacement" is a chemical group that is readily displaced by a desired incoming chemical moiety. Suitable leaving groups are well known in the art, e.g., see, March. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitrophenylsulfonyloxy (nosyloxy), and bromo-phenylsulfonyloxy (brosyloxy).

According to an alternate embodiment, the suitable leaving group may be generated in situ within the reaction medium. For example, a leaving group may be generated in situ from a precursor of that compound wherein said precursor contains a group readily replaced by said leaving group in situ.

Alternatively, when the $R^{2a}$ group of formula I is a mono- or di-protected amine, the protecting group(s) is removed and that functional group may be derivatized or protected with a different protecting group. It will be appreciated that the removal of any protecting group of the $R^{2a}$ group of formula I is performed by methods suitable for that protecting group. Such methods are described in detail in Green.

In other embodiments, the $R^{2a}$ group of formula I is incorporated by derivatization of the amino group of formula I', or freebase thereof, via anhydride coupling, optionally in the presence of base as appropriate. One of ordinary skill in the art would recognize that anhydride polymerization terminating agents containing an azide, an aldehyde, a hydroxyl, an alkyne, and other groups, or protected forms thereof, may be used to incorporate said azide, said aldehyde, said protected hydroxyl, said alkyne, and other groups into the $R^{2a}$ group of compounds of formula I. It will also be appreciated that such anhydride polymerization terminating agents are also suitable for terminating the living polymer chain-end of a compound of formula I', or freebase thereof. Such anhydride polymerization terminating agents include, but are not limited to, those set forth in Table 7, below.

TABLE 7

Representative Anhydride Polymerization Terminating Agents

TABLE 7-continued

Representative Anhydride Polymerization Terminating Agents

In other embodiments, the $R^4$ moiety of the $R^{2a}$ group of formula III is incorporated by derivatization of the amino group of formula I', or freebase thereof, via reaction with a polymerization terminating agent having a suitable leaving group. It will also be appreciated that such polymerization terminating agents are also suitable for terminating the living polymer chain-end of a compound of formula I', or freebase thereof. Examples of these polymerization terminating agents include, but are not limited to, those set forth in Table 8, below.

TABLE 8
Representative Polymerization Terminating Agents
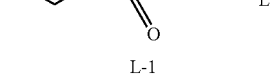

TABLE 8-continued

Representative Polymerization Terminating Agents

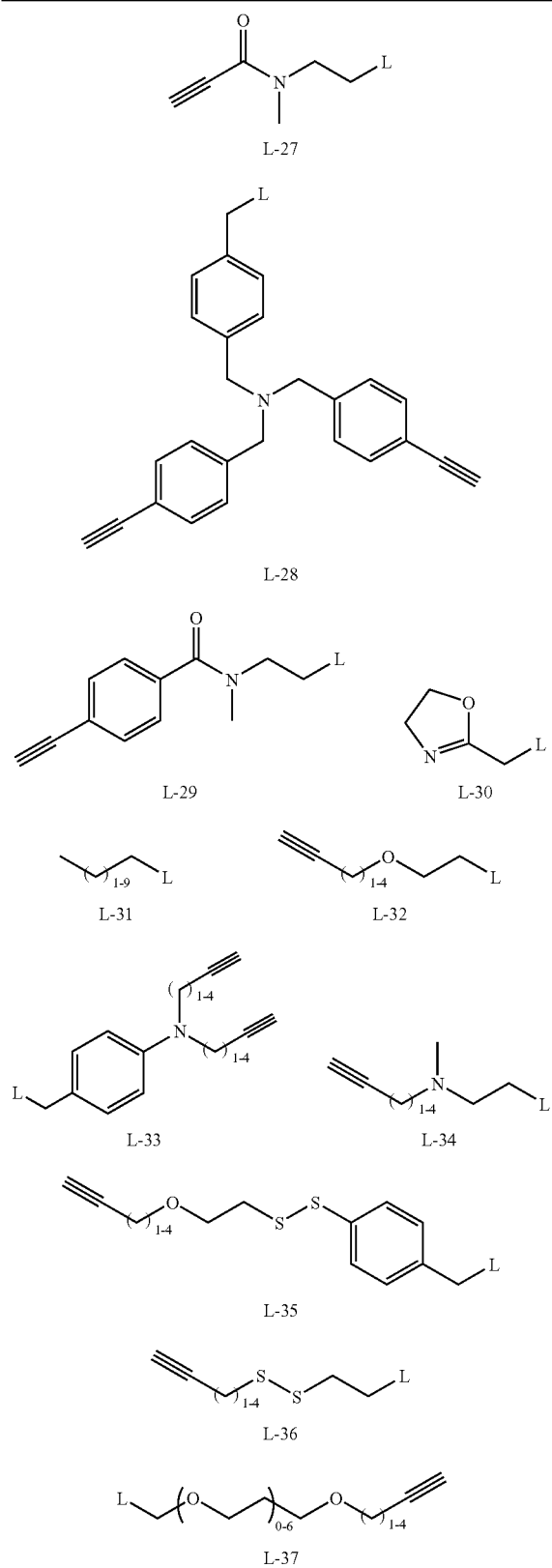

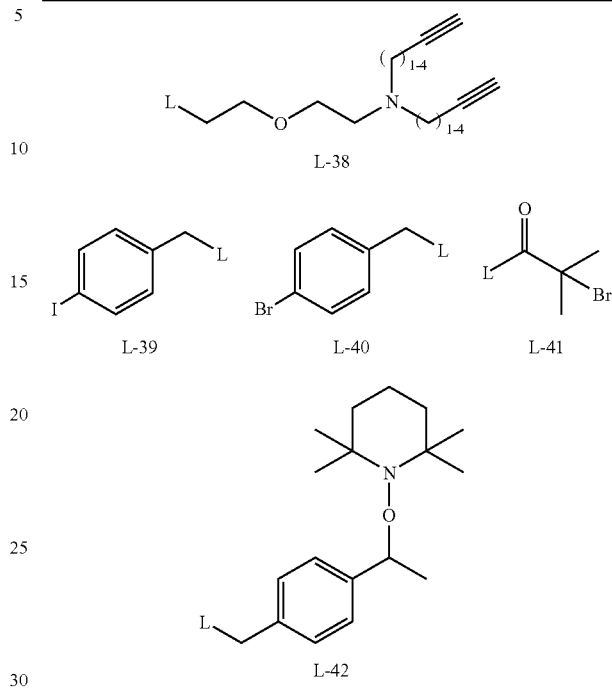

wherein each L is a suitable leaving group as defined above and in classes and subclasses as described above and herein.

In certain embodiments, the hydrophilic polymer block is poly(ethylene glycol) (PEG) having a terminal amine salt ("PEG macroinitiator"). This PEG macroinitiator initiates the polymerization of NCAs to provide the multiblock copolymers of the present invention. Such polymers having a terminal amine salt may be prepared from synthetic polymers having a terminal amine. Such synthetic polymers having a terminal amine group are known in the art and include PEG-amines. PEG-amines may be obtained by the deprotection of a suitably protected PEG-amine. Preparation of such suitably protected PEG-amines, and methods of deprotecting the same, is described in detail in U.S. patent application Ser. No. 11/256,735, filed Oct. 24, 2005 the entirety of which is hereby incorporated herein by reference.

As described in U.S. Ser. No. 11/256,735, suitably protected PEG-amines may be formed by terminating the living polymer chain end of a PEG with a terminating agent that contains a suitably protected amine. The suitably protected amine may then be deprotected to generate a PEG that is terminated with a free amine that may subsequently be converted into the corresponding PEG-amine salt macroinitiator. In certain embodiments, the PEG-amine salt macroinitiator of the present invention is prepared directly from a suitably protected PEG-amine by deprotecting said protected amine with an acid. Accordingly, in other embodiments, the terminating agent has suitably protected amino group wherein the protecting group is acid-labile.

Alternatively, suitable synthetic polymers having a terminal amine salt may be prepared from synthetic polymers that contain terminal functional groups that may be converted to amine salts by known synthetic routes. In certain embodiments, the conversion of the terminal functional groups to the amine salts is conducted in a single synthetic step. In other embodiments, the conversion of the terminal functional groups to the amine salts is achieved by way of a multi-step sequence. Functional group transformations that afford amines, amine salts, or protected amines are well known in the art and include those described in Larock, R. C., "Comprehensive Organic Transformations," John Wiley & Sons, New York, 1999.

used when micelles are formed from poorly aqueous soluble copolymes. The copolymer is dissolved in a water miscible organic solvent such as N-methyl pyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. Alternatively,

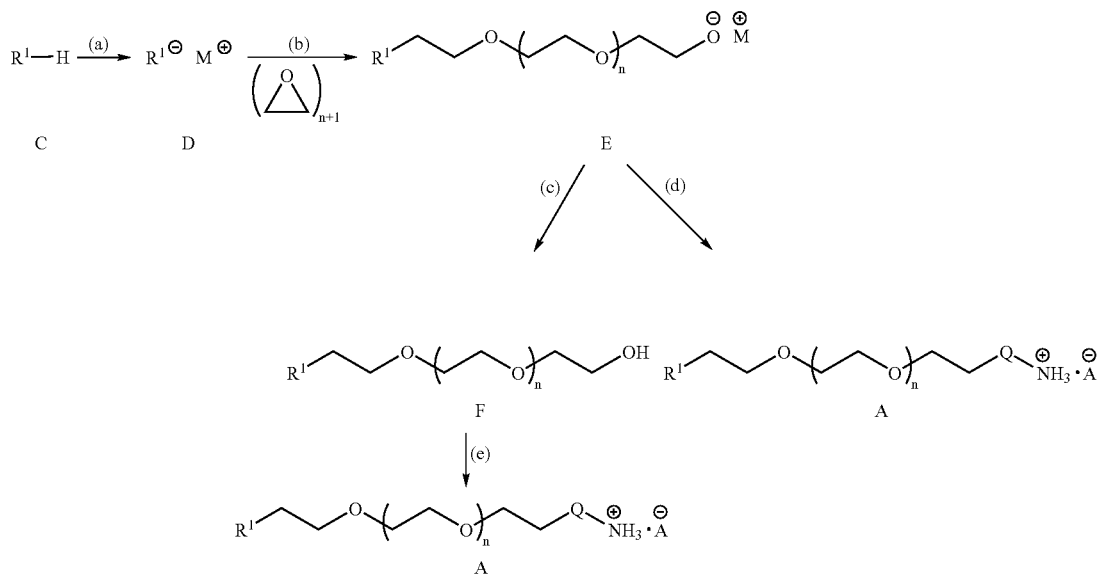

Scheme 3 above shows one exemplary method for preparing the bifunctional PEGs used to prepare the multiblock copolymers of the present invention. At step (a), the polymerization initiator is treated with a suitable base to form D. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer E. Polymer E can be transformed at step (d) to a compound of formula A directly by terminating the living polymer chain-end of E with a suitable polymerization terminator to afford a compound of formula A. Alternatively, polymer E may be quenched at step (c) to form the hydroxyl compound F. Compound F is then derivatized to afford a compound of formula A by methods known in the art, including those described herein. Each of the $R^1$, A, n, and Q groups depicted in Scheme 3 are as defined and described in classes and subclasses, singly and in combination, herein.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

Methods of preparing micelles are known to one of ordinary skill in the art. Micelles can be prepared by a number of different dissolution methods. In the direct dissolution method, the block copolymer is added directly to an aqueous medium with or without heating and micelles are spontaneously formed up dissolution. The dialysis method is often the block copolymer can be dissolved in a water miscible organic solvent such as N-methyl pyrollidinone, dimethylformamide, dimethylsulfoxide, tetrahydrofuran, or dimethylacetamide and added dropwise to water or another aqueous medium. The micelles can then be isolated by filtration or lyophilization.

In one embodiment, drug-loaded miclles possessing carboxylic acid functionality in the outer core are crosslinked by addition of zinc chloride to the micelle solution along with a small amount of sodium bicarbonate to neutralize any hydrochloric acid by-product. In this basic pH environment, the reaction of zinc chloride with the poly(aspartic acid) crosslinking block should be rapid and irreversible.

In another embodiment, drug loaded micelles possessing amine functionality in the outer core are crosslinked by the addition of a bifunctional, or multi-functional aldehyde-containing molecule which forms pH-reversible imine crosslinks. In another embodiment, drug loaded micelles possessing aldehyde functionality in the outer core are crosslinked by the addition of a bifunctional, or multi-functional amine-containing molecule which forms pH-reversible imine crosslinks.

In another embodiment, drug loaded micelles possessing alcohol or amine functionality in the outer core are crosslinked by the addition of a bifunctional, or multi-functional carboxylic acid-containing molecules and a coupling agent to form amide or ester crosslinks. In yet another embodiment, drug loaded micelles possessing carboxylic acid functionality in the outer core are crosslinked by the addition of a bifunctional, or multi-functional amine or alcohol-containing molecules and a coupling agent to form amide or ester crosslinks. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, drug loaded micelles possessing aldehyde or ketone functionality in the outer core are crosslinked by the addition of a bifunctional, or multifunctional hydrazine or hydrazide-containing molecule to form pH-reversible hydrazone crosslinks. In still other embodiments, drug loaded micelles hydrazine or hydrazide-functionality in the outer core are crosslinked by the addition of a bifunctional, or multifunctional aldehyde or ketone-containing molecule to form pH-reversible hydrazone crosslinks.

In another embodiment, drug loaded micelles possessing thiol functionality in the outer core are crosslinked by the addition of an oxidizing agent (e.g. metal oxides, halogens, oxygen, peroxides, ozone, peroxyacids, etc.) to form disulfide crosslinks. It will be appreciated that disulfide crosslinks are reversible in the presence of a suitable reducing agent (e.g. glutathione, dithiothreitol (DTT), etc.).

In yet another embodiment, drug loaded micelles possessing both carboxylic acid and thiol functionality in the outer core can be dual crosslinked by the addition of an oxidizing agent (e.g. metal oxides, halogens, oxygen, peroxides, ozone, peroxyacids, etc.) to form disulfide crosslinks followed by the addition of zinc chloride to the micelle solution along with a small amount of sodium bicarbonate to neutralize any hydrochloric acid by-product. It will be appreciated that such a dual-crosslinked micelle is reversible only in the presence of acid and a reducing agent (e.g. glutathione, dithiothreitol (DTT), etc.).

According to another aspect, the present invention provides a method for preparing a micelle comprising a multi-block copolymer which comprises a polymeric hydrophilic block, a crosslinked poly(amino acid block), and a poly(amino acid) block, characterized in that said micelle has an inner core, a crosslinked outer core, and a hydrophilic shell, said method comprising the steps of:

(a) providing a multiblock copolymer of formula I:

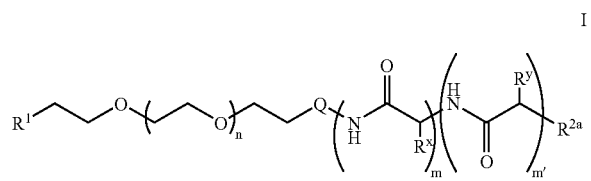

I wherein:
n is 10-2500;
m is 1 to 1000;
m' is 1 to 1000;
$R^x$ is a natural or unnatural amino acid side-chain group that is capable of crosslinking;
$R^y$ is a hydrophobic or ionic, natural or unnatural amino acid side-chain group;
$R^1$ is -Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C$_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, (b) combining said compound of formula I with a therapeutic agent; and
(c) treating the resulting micelle with a crosslinking reagent to crosslink $R^x$.

In one embodiment, drugs are loaded into the micelle inner core by adding an aliquot of a copolymer solution in water to the drug to be incorporated. For example, a stock solution of the drug in a polar organic solvent is made and allowed to evaporate, and then the copolymer/water solution is added. In another embodiment, the drug is incorporated using an oil in water emulsion technique. In this case, the drug is dissolved in an organic solvent and added dropwise to the micelle solution in water, and the drug is incorporated into the micelle during solvent evaporation. In another embodiment, the drug is dissolved with the copolymer in a common polar organic solvent and dialyzed against water or another aqueous medium. See Allen, C.; Maysinger, D.; Eisenberg A. *Colloid Surface B* 1999, 16, 3-27.

In still another embodiment, the loading and crosslinking of drug-filled micelles is carried out by dissolving neutral doxorubicin, camptothecin, or paclitaxel and the block copolymer in a polar solvent such as acetone or ethanol, followed by slow addition to water or buffer solution. Due to the limited solubility of DOX and CPT in water, the drug is forced into the core of the micelle, effectively encapsulating the drug.

5. Uses, Methods, and Compositions

As described herein, micelles of the present invention can encapsulate a wide variety of therpaeutic agents useful for treating a wide variety of diseases. In certain embodiments, the present invention provides a drug-loaded micelle, as described herein, wherein said micelle is useful for treating the disorder for which the drug is known to treat. According to one embodiment, the present invention provides a method for treating one or more disorders selected from pain, inflammation, arrhythmia, arthritis (rheumatoid or osteoarthritis), atherosclerosis, restenosis, bacterial infection, viral infection, depression, diabetes, epilepsy, fungal infection, gout, hypertension, malaria, migraine, cancer or other proliferative disorder, erectile dysfunction, a thyroid disorder, neurological disorders and hormone-related diseases, Parkinson's disease, Huntington's disease, Alzheimer's disease, a gastro-intestinal disorder, allergy, an autoimmune disorder, such as asthma or psoriasis, osteoporosis, obesity and comorbidities, a cognitive disorder, stroke, AIDS-associated dementia, amyotrophic lateral sclerosis (ALS, Lou Gehrig's disease), multiple sclerosis (MS), schizophrenia, anxiety, bipolar disorder, tauopothy, a spinal cord or peripheral nerve injury, myocardial infarction, cardiomyocyte hypertrophy, glaucoma, an attention deficit disorder (ADD or ADHD), a sleep disorder, reperfusion/ischemia, an angiogenic disorder, or urinary incontinence, comprising adminsitering to a patient a micelle comprising a multiblock copolymer which comprises a polymeric hydrophilic block, a crosslinked poly(amino acid block), and a poly(amino acid block), characterized in that said micelle has a drug-loaded inner core, a crosslinked outer core, and a hydrophilic shell, wherein said micelle encapsulates a therapeutic agent suitable for treating said disorder.

In other embodiments, the present invention provides a method for treating one or more disorders selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, comprising adminsitering to a patient a micelle comprising a multiblock copolymer which comprises a polymeric hydrophilic block, a crosslinked poly(amino acid block), and a poly(amino acid block), characterized in that said micelle has a drug-loaded inner core, a crosslinked outer core, and a hydrophilic shell, wherein said micelle encapsulates a therapeutic agent suitable for treating said disorder.

In certain embodiments, drug-loaded micelles of the present invention are useful for treating cancer. Accordingly, another aspect of the present invention provides a method for treating cancer in a patient comprising adminsitering to a patient a micelle comprising a multiblock copolymer which comprises a polymeric hydrophilic block, a crosslinked poly(amino acid block), and a poly(amino acid block), characterized in that said micelle has a drug-loaded inner core, a crosslinked outer core, and a hydrophilic shell, wherein said micelle encapsulates a chemotherapeutic agent. According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering a micelle in accordance with the present invention wherein said micelle encapsulates a chemotherapeutic agent suitable for treating said cancer.

P-glycoprotein (Pgp, also called multidrug resistance protein) is found in the plasma membrane of higher eukaryotes where it is responsible for ATP hydrolysis-driven export of hydrophobic molecules. In animals, Pgp plays an important role in excretion of and protection from environmental toxins; when expressed in the plasma membrane of cancer cells, it can lead to failure of chemotherapy by preventing the hydrophobic chemotherapeutic drugs from reaching their targets inside cells. Indeed, Pgp is known to transport hydrophobic chemotherapeutic drugs out of tumor cells. According to one aspect, the present invention provides a method for delivering a hydrophobic chemotherapeutic drug to a cancer cell while preventing, or lessening, Pgp excretion of that chemotherapeutic drug, comprising administering a drug-loaded micelle comprising a multiblock polymer of the present invention loaded with a hydrophobic chemotherapeutic drug. Such hydrophobic chemotherapeutic drugs are well known in the art and include those described herein.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In other embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXAMPLES

Preparation of Bifunctional PEGs and Multiblock Copolymers of the Present Invention As described generally above, multiblock copolymers of the present invention are prepared using the heterobifunctional PEGs described herein and in U.S. patent application Ser. No. 11/256,735, filed Oct. 24, 2005, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006, the entirety of which is hereby incorporated herein by reference.

Example 1

Dibenzylamino-poly(ethylene glycol)-t-butyldiphenylsilylpropene: To a stirred solution of dibenzylaminoethanol (482 mg, 2 mmol) in anhydrous THF (200 mL) was added a solution of potassium naphthalenide in THF (0.2 M, 10 mL, 2 mmol). The resulting solution was cooled to 0° C., then ethylene oxide (20 g, 454 mmol) was introduced to the alkoxide solution using Schlenk techniques. Upon complete addition of the ethylene oxide, the flask was backfilled with Argon, sealed and stirred at 40° C. After 24 h, t-butyldiphenylsilylpropargyl bromide (3.54 g, 10 mmol) was added to the reaction using Schlenk techniques. The solution was stirred for and additional 12 h at 40° C., allowed to cool, and the solvent removed. The resulting viscous liquid was purified by solid phase extraction (The liquid was loaded onto 400 mL silica gel which was rinsed with 3% MeOH in CHCl$_3$ (1 L) followed by 10% MeOH in CHCl$_3$ (1 L) which contained the polymer product) then precipitation into cold diethyl ether to give a white powder (14.4 g, 72% yield). $^1$H NMR (400 MHz, DMSO-d$_6$, δ) 7.8-7.2 (m, Ar—H), 4.39 (s, CH$_2$-allyne), 3.7-3.3 (br-m, —O—CH$_2$—CH$_2$—) 1.03 (s, t-butyl). Mn~9800 by $^1$H NMR.

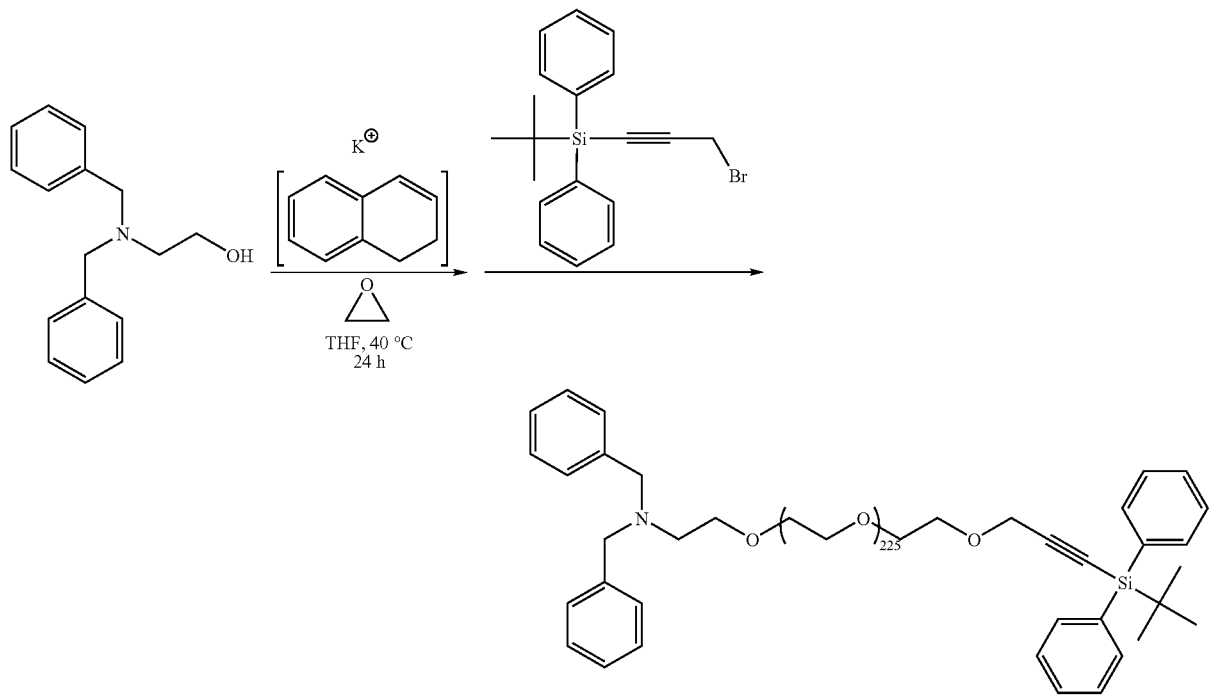

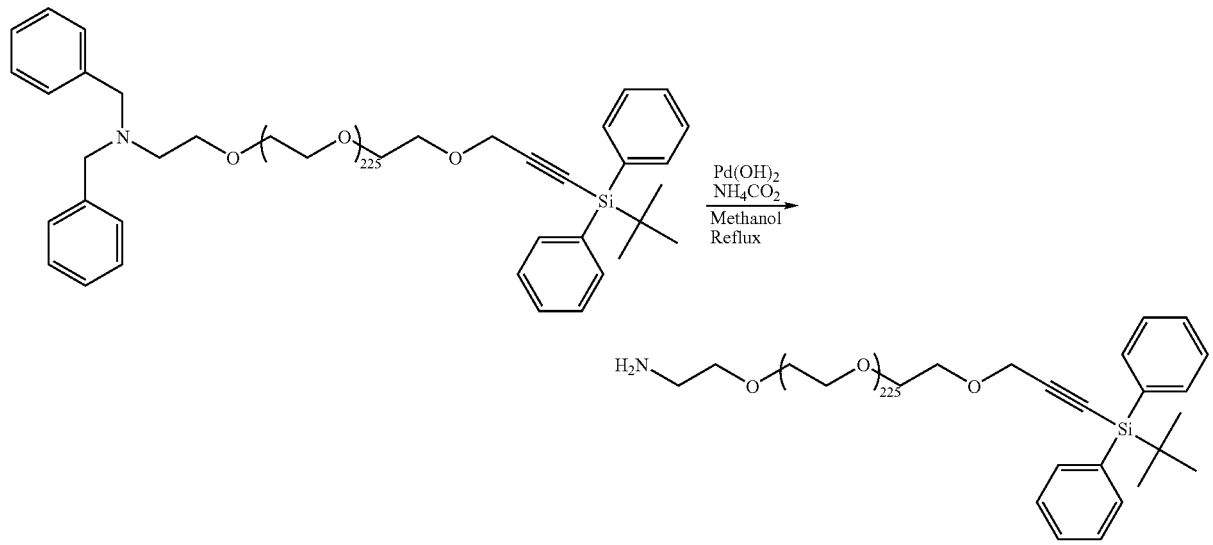

Amino-poly(ethylene glycol)-t-butyldiphenylsilylpropene: To a 100 mL round bottom flask was added 10% palladium hydroxide on carbon (0.2 g) and methanol (200 mL). Dibenzylamino-poly(ethylene glycol)-t-butyldiphenylsilylpropene (2 g) and ammonium formate (2 g) was added and the reaction heated to reflux. After 6 hours, potassium carbonate (4 g) was added and the solution stirred for an additional 3 hours at reflux. The solution was diluted with chloroform (200 mL), allowed to cool, then filtered over basic alumina. The solvent was evaporated and the polymer product precipitated into cold diethyl ether and recovered as a white powder following filtration (1.2 g, 60% yield). $^1$H NMR (400 MHz, DMSO-$d_6$, δ) 7.6-7.3 (m, Ar—H), 4.19 (s, $CH_2$-alkyne), 3.7-3.3 (br-m, —O—$CH_2$—$CH_2$—O—), 0.96 (s, t-butyl).

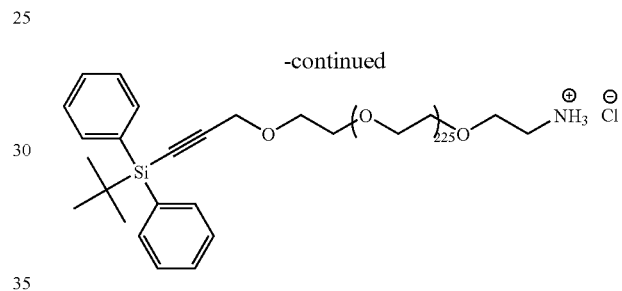

Ammonium chloride-poly(ethylene glycol)-t-butyldiphenylsilylpropene: To a 50 mL round bottom flask with stir bar was added amino-poly(ethylene glycol)-t-butyldiphenylsilylpropene (1.2 g, 0.1 mmol) and THF (5 mL). The solution was stirred at room temperature until a homogeneous solution was present. 4 M HCl in dioxane (5 mL) was then added and the solution stirred for 1 hour. The polymer was precipitated into cold ether to give a white powder (1 g, 83% yield). $^1$H NMR (400 MHz, DMSO-$d_6$, δ) 7.85 (br-s, —$NH_3Cl$, 7.58 (m, Ar—H), 7.45 (m, Ar—H), 7.41 (m, Ar—H), 4.17 (s, $CH_2$-alkyne), 3.7-3.3 (br-m, —O—$CH_2$—$CH_2$—), 0.97 (s, t-butyl).

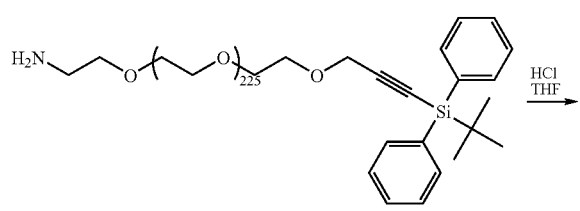

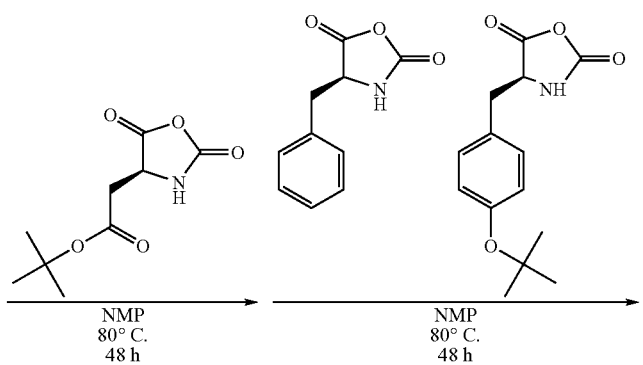

-continued

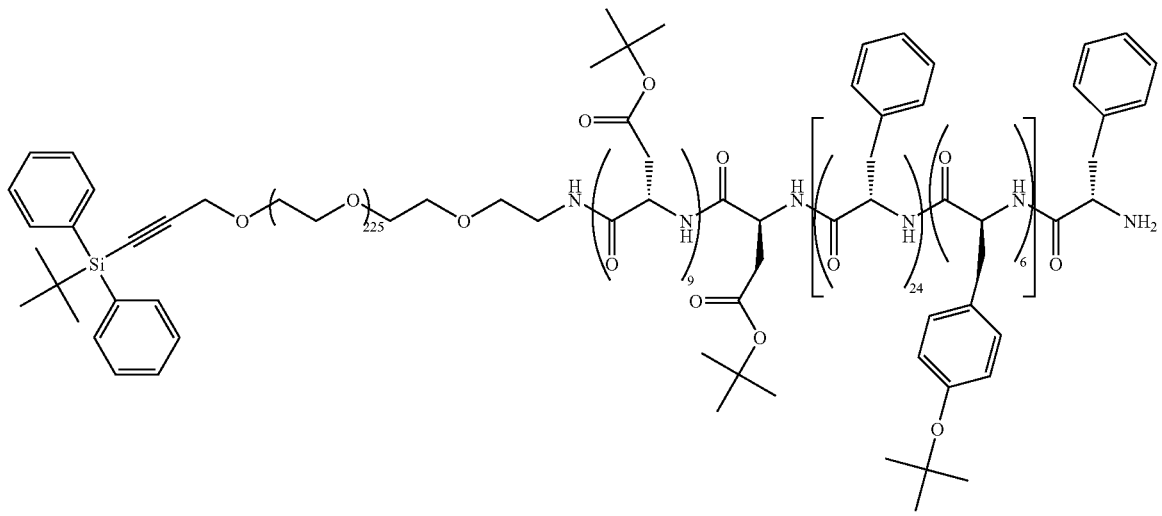

TBDPS-propyne-poly(ethylene glycol)-b-poly(t-butyl aspartic acid)-b-[poly(phenylalanine)-co-poly(t-butyl tyrosine)]: To a 100 mL reaction vessel equipped with glass stir bar and Teflon valve was added ammonium chloride-poly(ethylene glycol)-t-butyldiphenylsilylpropene (0.6 g, 0.05 mmol) and t-butyl aspartic acid NCA (0.11 g, 0.5 mmol). The flask was evacuated for 1 h then backfilled with Ar. Anhydrous NMP (7 mL) was added via syringe then the flask sealed under and Ar atmosphere and stirred at 80° C. After 48 h, phenylalanine NCA (0.32 g, 1.2 mmol) and t-butyl tyrosine (0.08 g, 0.3 mmol) were dried under vacuum, dissolved in anhydrous NMP (4 mL), and added to the reaction solution using Schlenk techniques. The resulting solution was stirred at 80° C. for an additional 48 h. The polymerization was then allowed to cool and the product precipitated into cold ether, giving a white powder (0.7 g, 65%). $^1$H NMR (400 MHz, DMSO-$d_6$, δ) 9.10, 8.04, 7.56, 7.41, 7.14, 6.95, 6.60, 4.51, 3.7-3.2, 2.92, 2.70, 1.37, 1.31, 0.97. Mn~14,500 by $^1$H NMR.

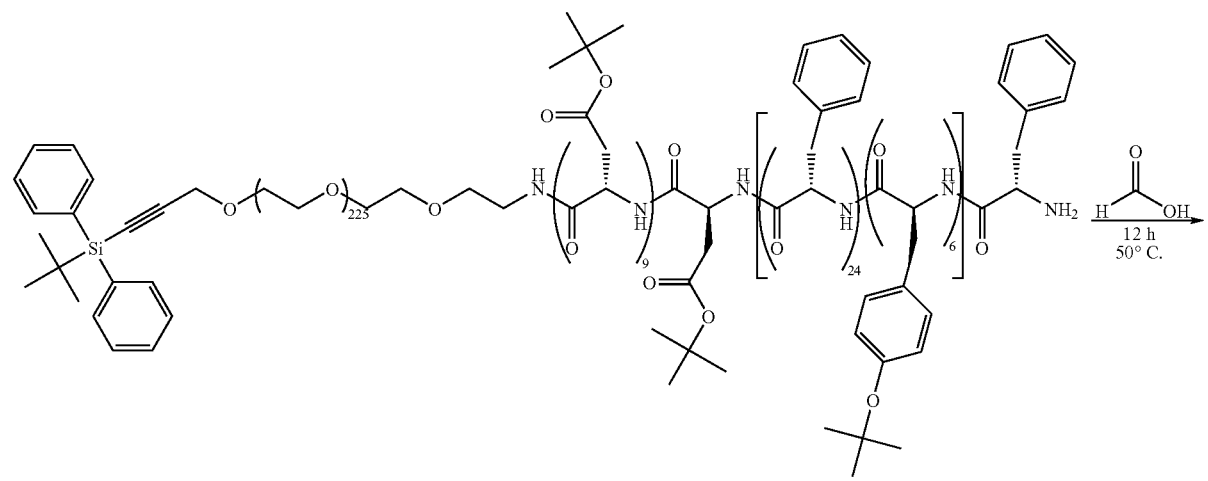

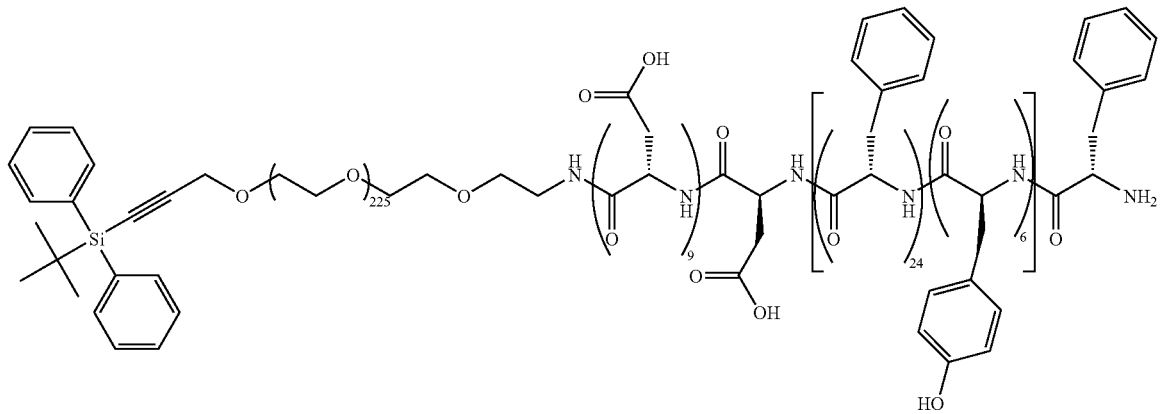

TBDPS-propyne-poly(ethylene glycol)-b-poly(aspartic acid)-b-[poly(phenylalanine)-co-poly(tyrosine)]: To a 50 mL round bottom flask with stir bar was added TBDPS-propyne-poly(ethylene glycol)-b-poly(t-butyl aspartic acid)-b-[poly(phenylalanine)-co-poly(t-butyl tyrosine)] (0.5 g) and formic acid (10 mL). The solution was stirred at 50° C. for 12 h, then the solvent evaporated. The residue was dissolved in methanol and the solvent again evaporated. The residue was again dissolved in methanol then precipitated into cold ether, giving a white powder (0.4 g, 80% yield). $^1$H NMR (400 MHz, DMSO-$d_6$, δ) 9.17, 8.14, 8.05, 7.56, 7.41, 7.21, 7.15, 6.96, 6.60, 4.51, 3.7-3.2, 2.93, 2.71, 0.97.

Example 2

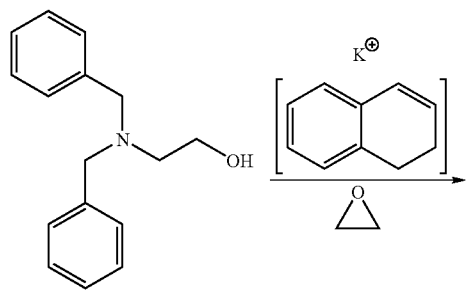

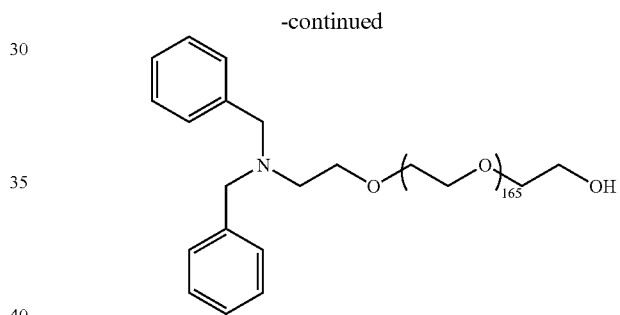

Dibenzylamino-polyethylene glycol-alcohol: To a stirred solution of dibenzylaminoethanol (242 mg, 1 mmol) in anhydrous THF (100 mL) was added a solution of potassium naphthalenide in THF (0.2 M, 1 mL, 1 mmol). The resulting solution was stirred for 5 minutes then cooled to 0° C. Ethylene oxide (10 g, 227 mmol) was introduced to the alkoxide solution using Schlenk techniques. Upon complete additon of the ethylene oxide, the flask was backfilled with Argon, sealed and stirred at 40° C. for 24 h. The reaction was quenched with water (1 mL) followed by the removal of solvent under reduced pressure. The resulting viscous liquid was purified by solid phase extraction (The liquid was loaded onto 200 mL silica gel which was rinsed with 3% MeOH in CHCl$_3$ (1 L) followed by 10% MeOH in CHCl$_3$ (1 L) which contained the polymer product) then precipitation into cold diethyl ether to give a white powder (6.8 g, 68% yield). $^1$H NMR (400 MHz, DMSO-$d_6$, δ) 7.4-7.2 (m, Ar—H), 4.63 (t, CH$_2$OH), 3.7-3.3 (br-m, —O—CH$_2$—CH$_2$—). GPC (DMF, PEG standards) $M_n$=7,300; PDI=1.03.

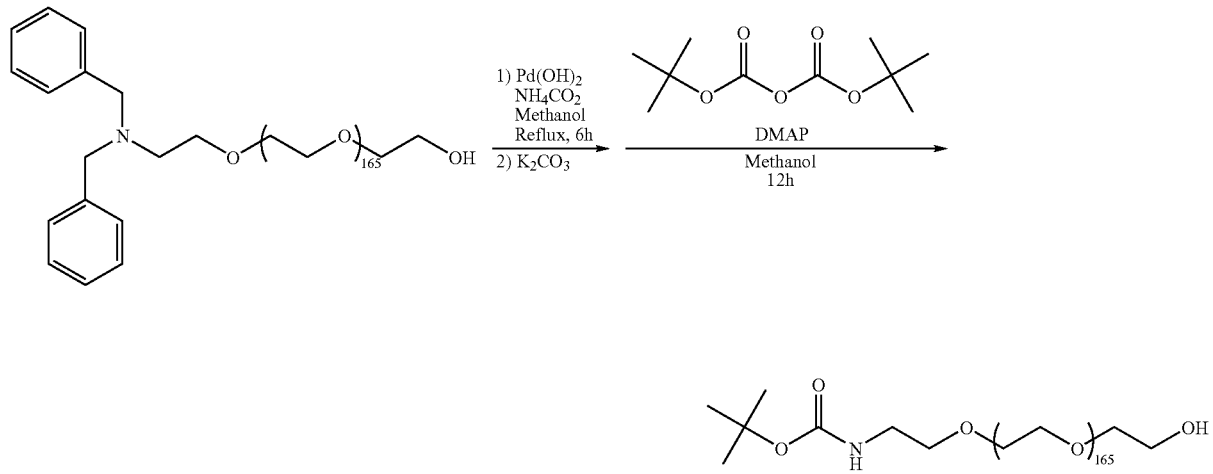

BOC-amino-poly(ethylene glycol)-alcohol: To a 250 mL round bottom flask was added 10% palladium hydroxide on carbon (1 g) and methanol (100 mL). Dibenzylamino-poly(ethylene glycol)-alcohol (5 g) and ammonium formate (5 g) was added and the reaction heated to reflux. After 6 hours, potassium carbonate (10 g) was added and the solution stirred for an additional 3 hours at reflux. The solution was diluted with chloroform (300 mL), allowed to cool, then filtered over basic alumina. The solvent was evaporated and the polymer redissolved in methanol (100 mL). BOC anhydride (3 g) and DMAP (1 g) were added and the solution stirred at room temperature for 12 h. The solvent was removed and the residue was purified by solid phase extraction (The liquid was loaded onto 200 mL silica gel which was rinsed with 3% MeOH in CHCl$_3$ (1 L) followed by 10% MeOH in CHCl$_3$ (1 L) which contained the polymer product) then precipitation into cold diethyl ether to give a white powder (4.2 g, 84% yield). $^1$H NMR (400 MHz, DMSO-d$_6$, δ) 6.82 (br-s, CH$_2$—NH—CO—), 4.63 (t, CH$_2$OH), 3.7-3.3 (br-m, —O—CH$_2$—CH$_2$—O—), 1.40 (s, —C—(CH$_3$)$_3$).

BOC-amino-poly(ethylene glycol)-aryl-propyne: To a 50 mL round bottom flask with stir bar was added propargyl phenol (0.37 g, 2.5 mmol), triphenylphosphine (0.53 g, 2 mmol), BOC-amino-poly(ethylene glycol)-alcohol (3.6 g, 0.5 mmol) and THF (10 mL). The reaction was stirred at room temperature until a homogeneous solution was present then DIAD (0.3 g, 1.5 mmol) was added and the reaction stirred at room temperature for 16 hours. The solvent was then removed under reduced pressure and the resulting viscous liquid was purified by solid phase extraction (The liquid was loaded onto 200 mL silica gel which was rinsed with 3% MeOH in CHCl$_3$ (1 L) followed by 10% MeOH in CHCl$_3$ (1 L) which contained the polymer product). Pure product was obtained as a white powder following precipitation into cold ether (2.8 g, 77% yield). $^1$H NMR (400 MHz, DMSO-d$_6$, δ) 6.92 (m, Ar—H), 4.68 (s, O—CH$_2$-alkyne), 4.04 (s, Ar—O—CH$_2$), 3.7-3.3 (br-m, —O—CH$_2$—CH$_2$—), 2.55 (t, alkyne-H), 1.42 (s, —C—(CH$_3$)$_3$).

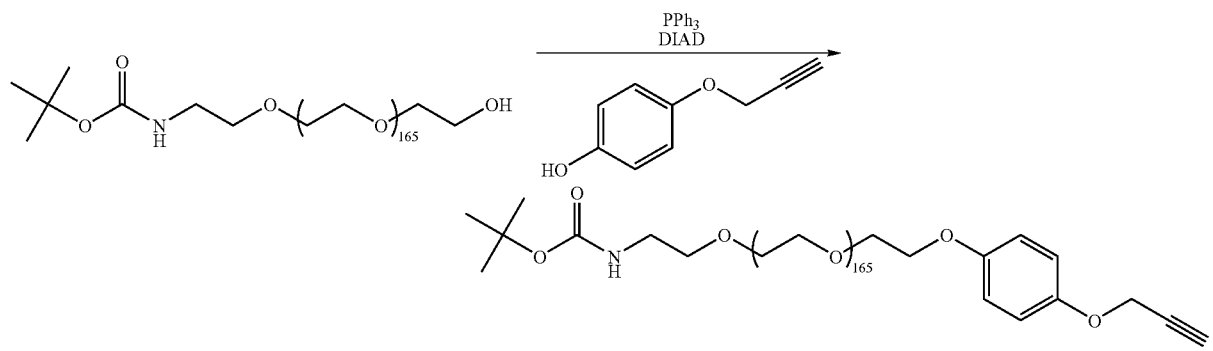

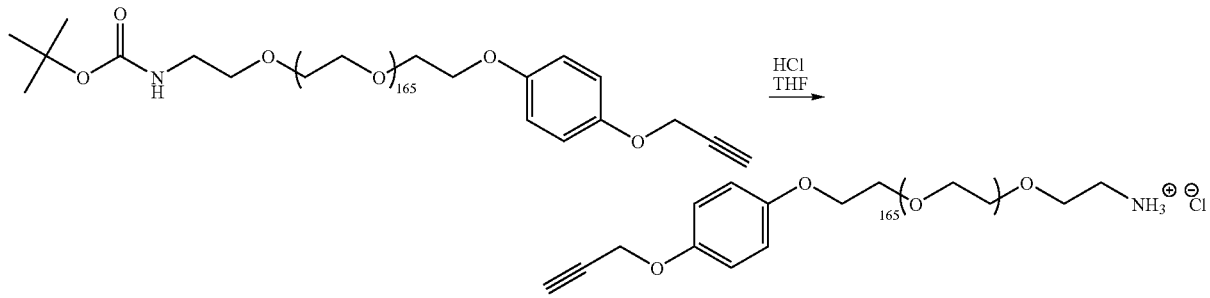

Propyne-aryl-poly(ethylene glycol)-ammonium chloride: To a 50 mL round bottom flask with stir bar was added BOC-amino-poly(ethylene glycol)-aryl-propyne (2 g, 0.1 mmol) and THF (5 mL). The solution was stirred at room temperature until a homogeneous solution was present. 4 M HCl in dioxane (5 mL) was then added and the solution stirred for 2 hours. The polymer was precipitated into cold ether to give a white powder (1.7 g, 85% yield). $^1$H NMR (400 MHz, DMSO-$d_6$, δ) 7.76 (br-s, —$NH_3Cl$), 6.90 (s, Ar—H), 4.71 (s, O—$CH_2$-alkyne), 4.02 (s, Ar—O—$CH_2$), 3.7-3.3 (br-m, —O—$CH_2$—$CH_2$—).

Propyne-aryl-poly(ethylene glycol)-b-poly(t-butyl aspartic acid)-b-[poly(phenylalanine)-co-poly(t-butyl tyrosine)]: To a 100 mL reaction vessel equipped with glass stir bar and Teflon valve was added Propyne-aryl-poly(ethylene glycol)-ammonium chloride (1.46 g, 0.2 mmol) and t-butyl aspartic acid NCA (0.43 g, 2 mmol). The flask was evacuated for 1 h then backfilled with Ar. Anhydrous NMP (20 mL) was added via syringe then the flask sealed under and Ar atmosphere and stirred at 80° C. After 48 h, phenylalanine NCA (1.26 g, 4.8 mmol) and t-butyl tyrosine (0.3 g, 1.2 mmol) were dried under vacuum, dissolved in anhydrous NMP (15 mL), and added to

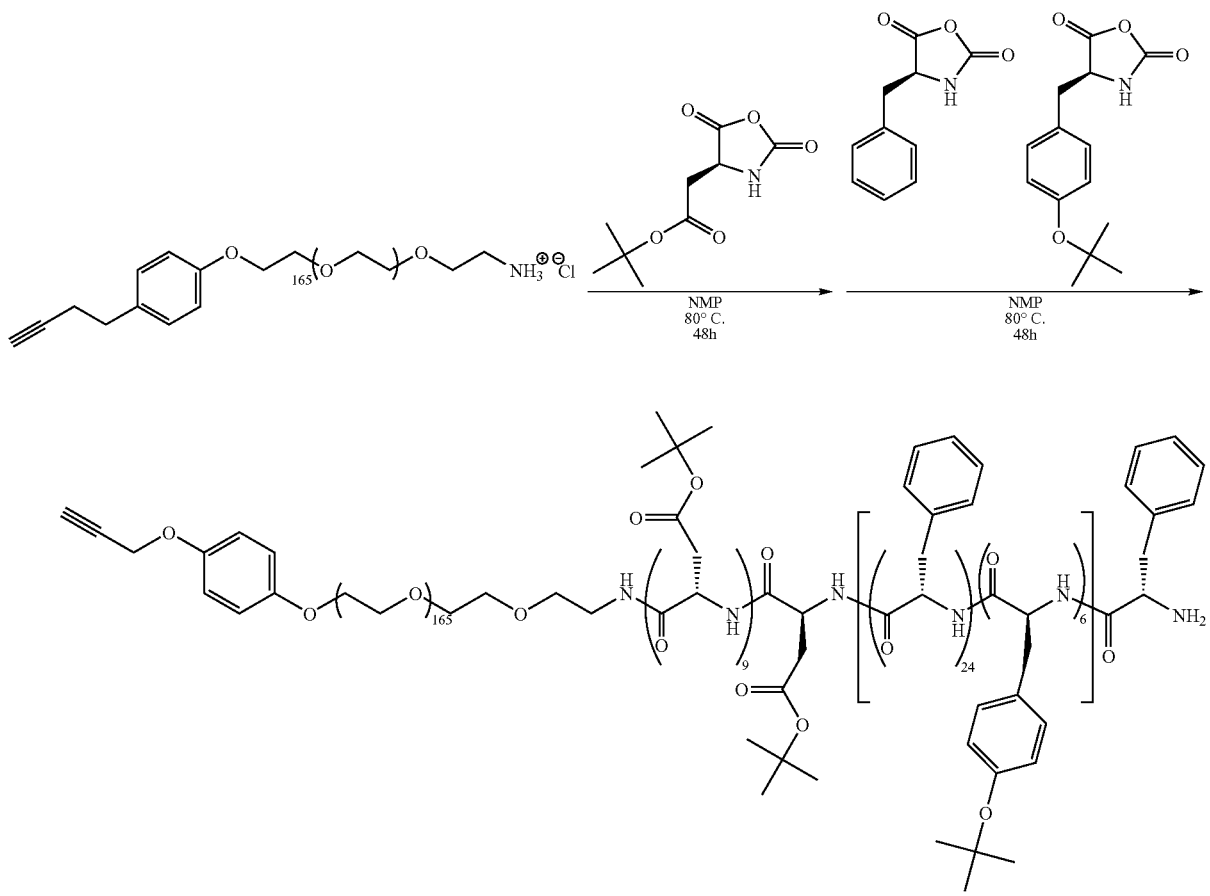

the reaction solution using Schlenk techniques. The resulting solution was stirred at 80° C. for an additional 48 h. The polymerization was then allowed to cool and the product precipitated into cold ether, giving a white powder (1.6 g, 54%). $^1$H NMR (400 MHz, DMSO-d$_6$, δ) 8.16, 8.08, 7.95, 7.21, 7.16, 6.91, 6.67, 4.70, 4.52, 4.02, 3.7-3.2, 3.04, 2.69, 2.19, 1.91, 1.37. Mn~11,600 by $^1$H NMR.

berg, A. "Critical Micellization Phenomena in Block Copolymer Polyelectrolyte Solutions" *Macromolecules* 1993, 26, 7339-7352.) To perform these experiments, a constant concentration of pyrene ($5 \times 10^{-7}$ M) was equilibrated with varying concentrations of block copolymer ($5 \times 10^{-4}$ M to $1 \times 10^{-8}$ M) in water at 50° C. for 2 hours, then stirred overnight. Examination of each sample's fluorescence excitation spectra

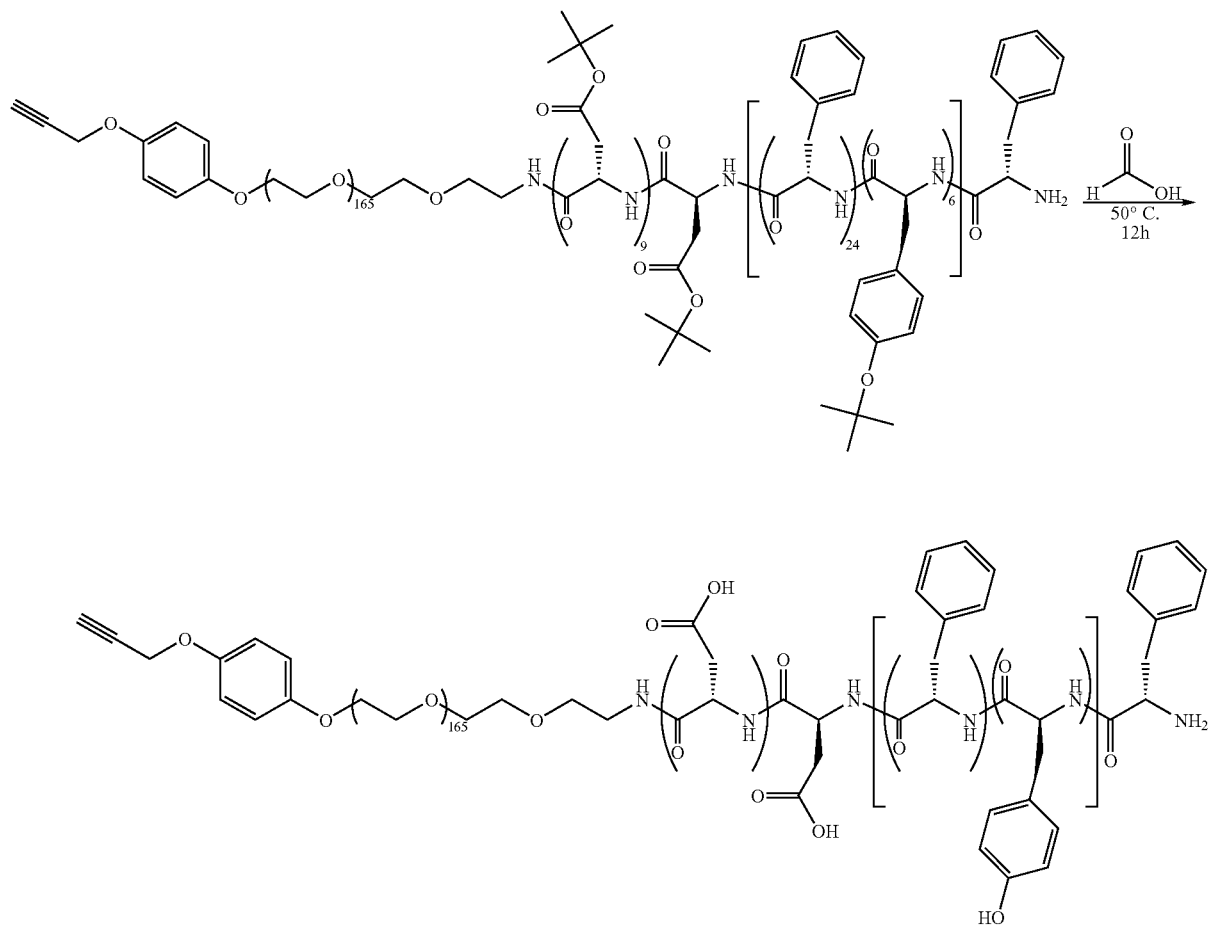

Propyne-aryl-poly(ethylene glycol)-b-poly(aspartic acid)-b-[poly(phenylalanine)-co-poly(tyrosine)]: To a 50 mL round bottom flask with stir bar was added Propyne-aryl-poly(ethylene glycol)-b-poly(t-butyl aspartic acid)-b-[poly(phenylalanine)-co-poly(t-butyl tyrosine)] (1 g) and formic acid (10 mL). The solution was stirred at 50° C. for 12 h, then the solvent evaporated. The residue was dissolved in methanol and the solvent again evaporated. The residue was again dissolved in methanol then precipitated into cold ether, giving a white powder. $^1$H NMR (400 MHz, DMSO-d$_6$, δ) 8.13, 8.07, 7.21, 7.18, 7.15, 7.00, 6.87, 6.60, 4.71, 4.52, 4.02, 3.7-3.2, 2.94, 2.74.

Example 3

Figure 11:
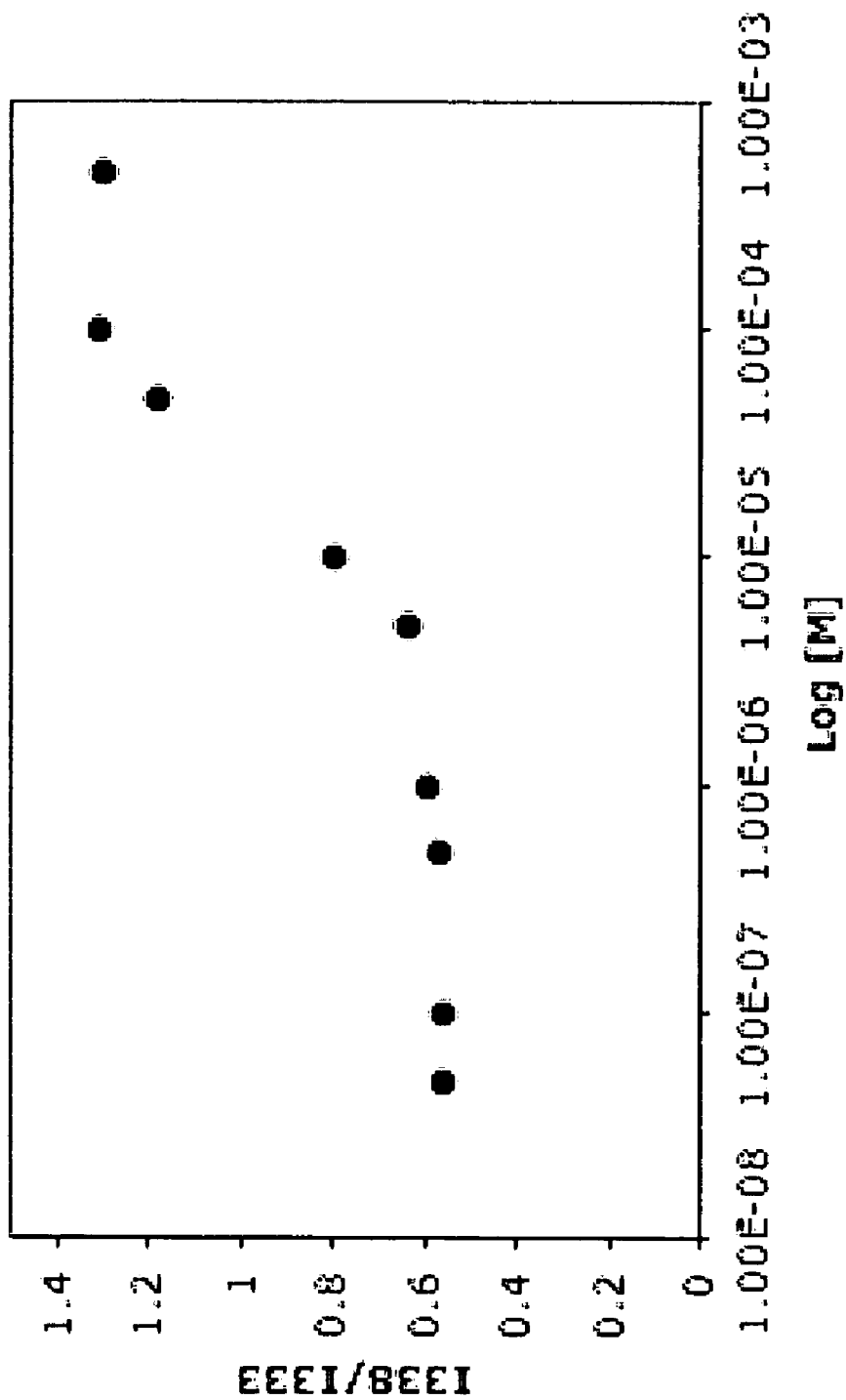
FIG. 11 shows the CMC experimental data for propyne-aryl-poly(ethylene glycol)-b-poly(aspartic acid)-b-[poly(phenylalanine)-co-poly(tyrosine)].

CMC Calculations: The CMC of micelles prepared from multiblock copolymers were determined using the method described by Eisnberg. (Astafieva, I.; Zhong, X. F.; Eisen- (excited at 390 nm) revealed whether the pyrene was encapsulated in the diblock copolymer micelle ($\lambda_{max}$=338 nm) or free in aqueous solution ($\lambda_{max}$=333 nm). Plotting the ratio of the intensities between 338 nm and 333 nm ($I_{338}/I_{333}$) vs. log of the block copolymer concentration allows for the graphical interpretation of the CMC value. In these experiments, $I_{338}/I_{333}$ values of 1.3-1.5 represent pyrene encapsulated in block copolymer micelles and $I_{338}/I_{333}$ values of 0.5-0.6 correspond to pyrene free in solution (no micelles are present). CMC experimental data for propyne-aryl-poly(ethylene glycol)-b-poly(aspartic acid)-b-[poly(phenylalanine)-co-poly(tyrosine)] (shown below) afforded a CMC value of $5 \times 10^{-6}$ M. See FIG. 11.

161
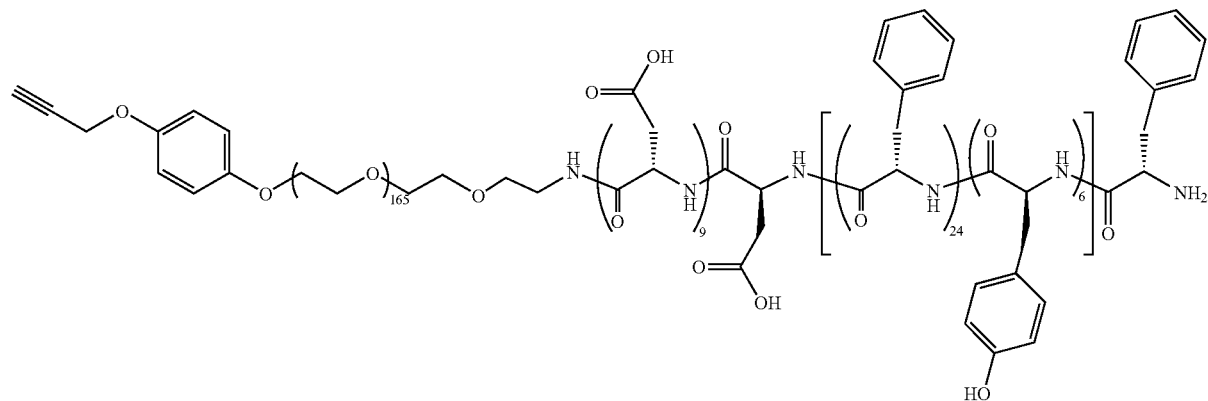
Example 4
162
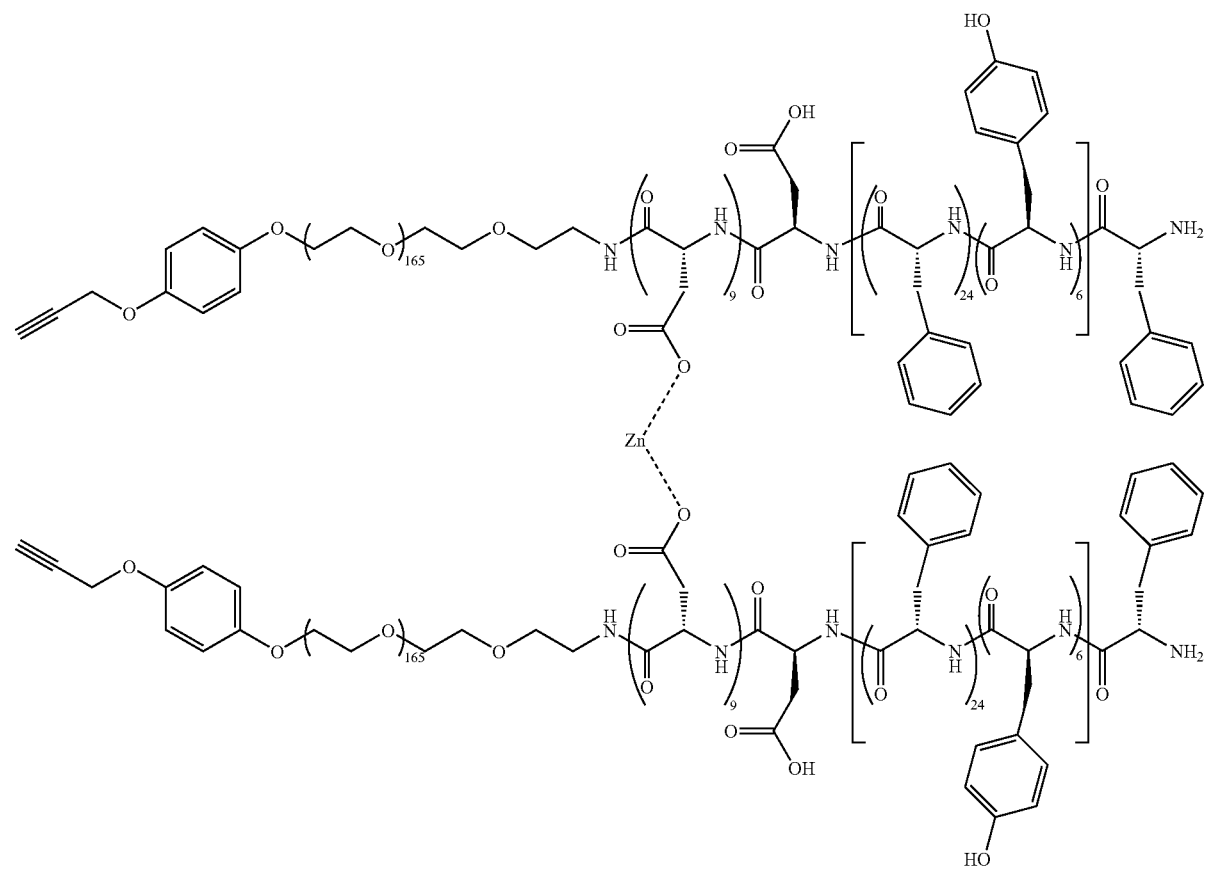
Zinc Crosslinked

-continued

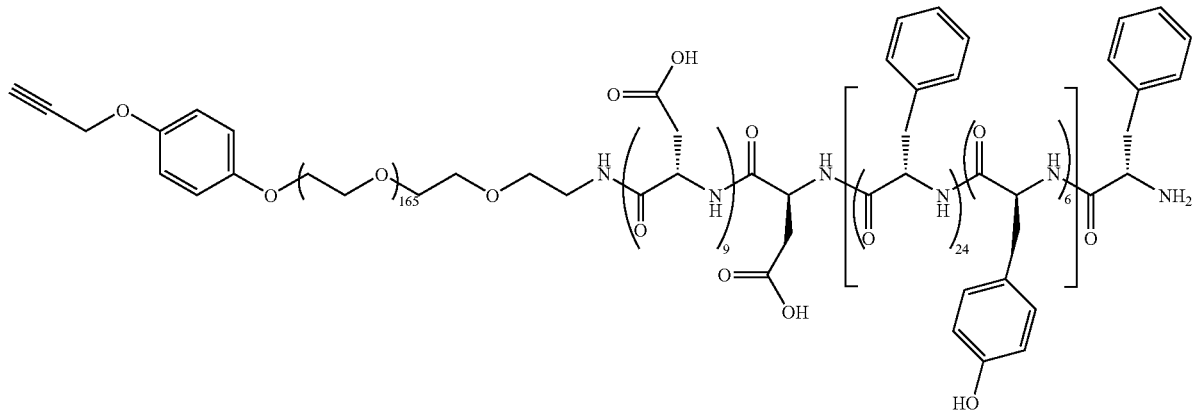

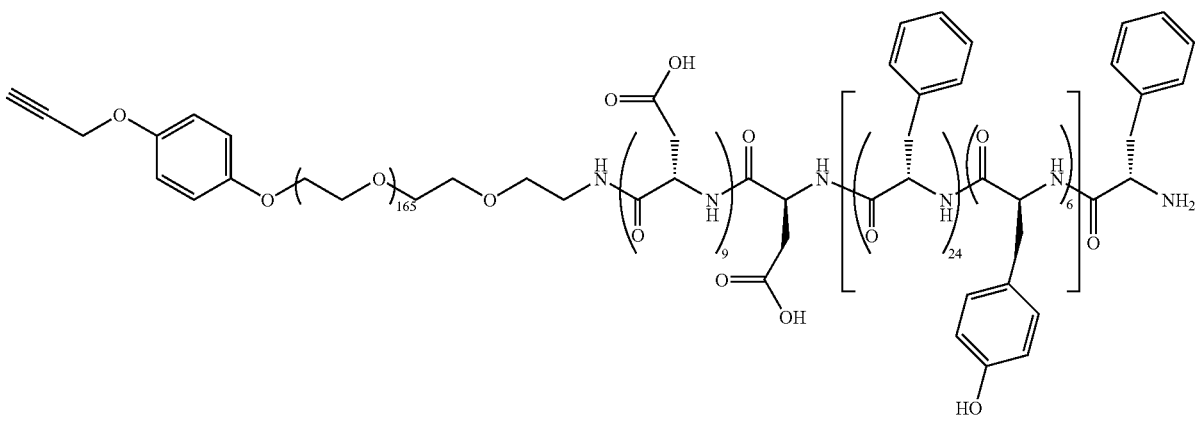

Uncrosslinked

Figure 12:
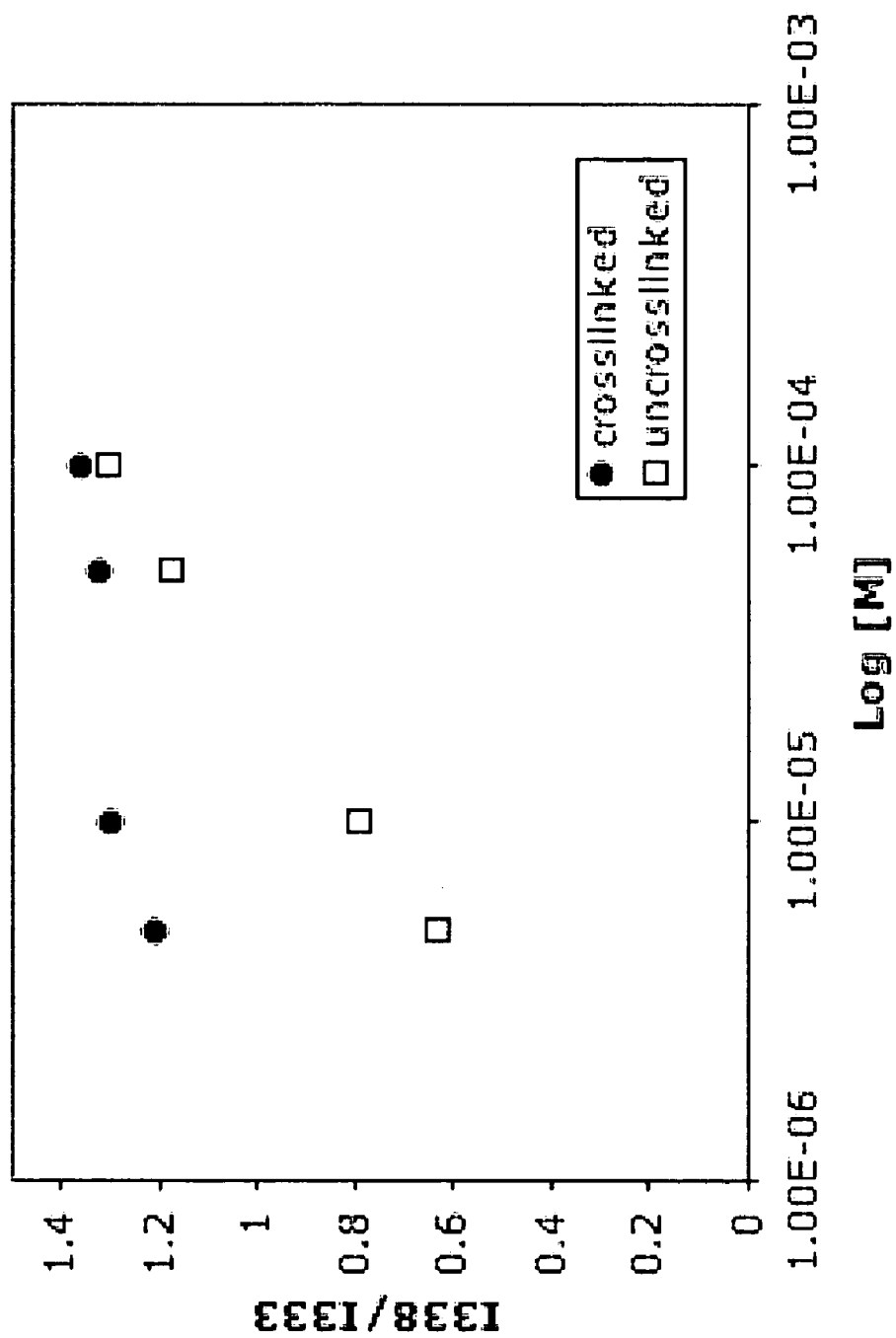
FIG. 12 shows a graphical comparison between zinc crosslinked micelles and uncrosslinked control experiments.

Preparation of zinc crosslinked micelles with encapsulated pyrene: Crosslinked micelles containing encapsulated pyrene were prepared by stirring pyrene and propyne-aryl-poly(ethylene glycol)-b-poly(aspartic acid)-b-[poly(phenylalanine)-co-poly(tyrosine)] in an aqueous zinc chloride solution at 50° C. for two hours then an additional 16 hours at room temperature ($2.5 \times 10^{-4}$ M polymer, 0.5 M $ZnCl_2$, $5 \times 10^{-7}$ M pyrene). 2 mL of 0.5 M $NaHCO_3$ was added, raising the pH to 8.2 from 3.1, and resulting solution was allowed to stir for an additional 2 hours. The solution was diluted to give samples with polymer concentrations of $1 \times 10^{-4}$, $5 \times 10^{-5}$, $1 \times 10^{-5}$, $5 \times 10^{-6}$ M. Examination of each sample's fluorescence excitation spectra (excited at 390 nm) revealed whether the pyrene was encapsulated in the diblock copolymer micelle ($\lambda_{max}$=338 nm) or free in aqueous solution ($\lambda_{max}$=333 nm). Plotting the ratio of the intensities between 338 nm and 333 nm ($I_{338}/I_{333}$) vs. log of the block copolymer concentration allows for the graphical interpretation of the CMC value. In these experiments, $I_{338}/I_{333}$ values of 1.3-1.5 represent pyrene encapsulated in block copolymer micelles and $I_{338}/I_{333}$ values of 0.5-0.6 correspond to pyrene free in solution (no micelles are present). A control experiment was performed in the absence of zinc chloride to show the effect of dilution on uncrosslinked micelles. Comparison between the zinc crosslinked micelles and uncrosslinked control experiments is shown in FIG. 12.

Example 5

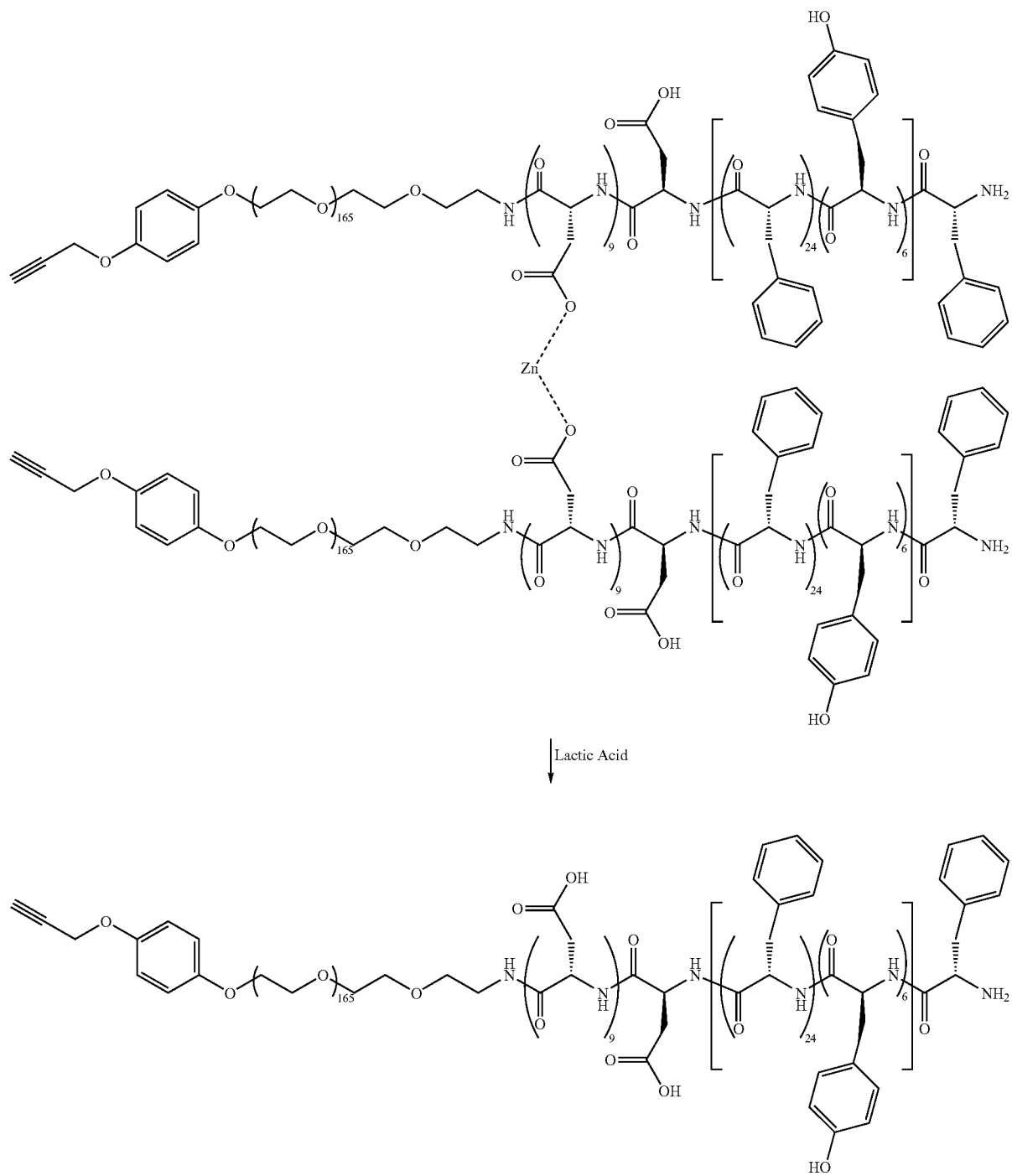

Figure 13:
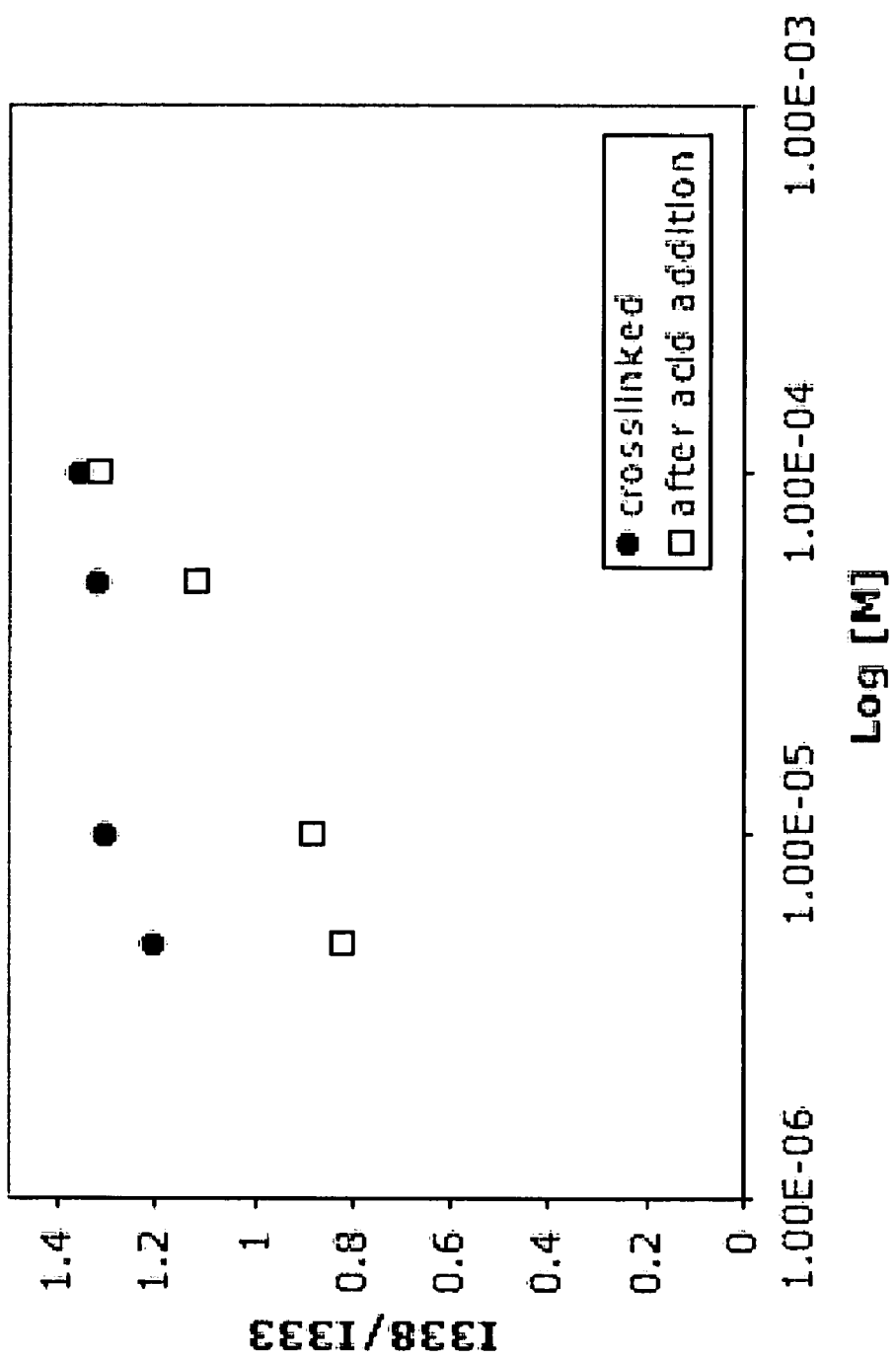
FIG. 13 depicts a graph of pyrene loaded crosslinked micelles before and after the addition of lactic acid.

Reversing of Zinc Crosslink by pH Adjustment: The pyrene loaded crosslinked micelles were uncrosslinked with the addition of acid. For these experiments, lactic acid (100 uL) was added to each of the crosslinked micelle samples and the fluorescence excitation apectra of pyrene recorded. The pH of the samples was lowered to pH 3.1 after the addition of the lactic acid (from 8.2 for the crosslinked micelles). Graph of the pyrene loaded crosslinked micelles before and after the addition of lactic acid is shown in FIG. 13.

Example 6
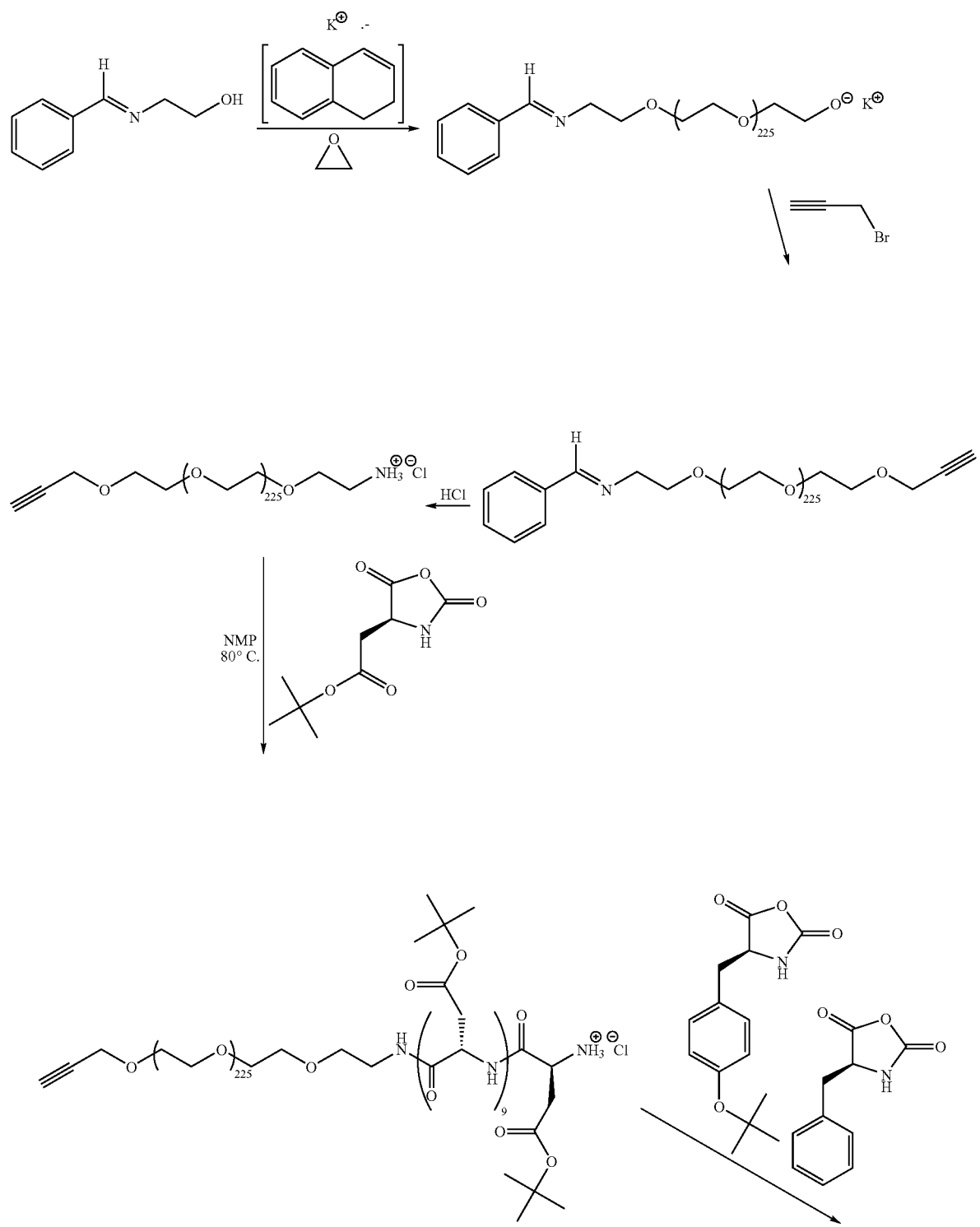

-continued

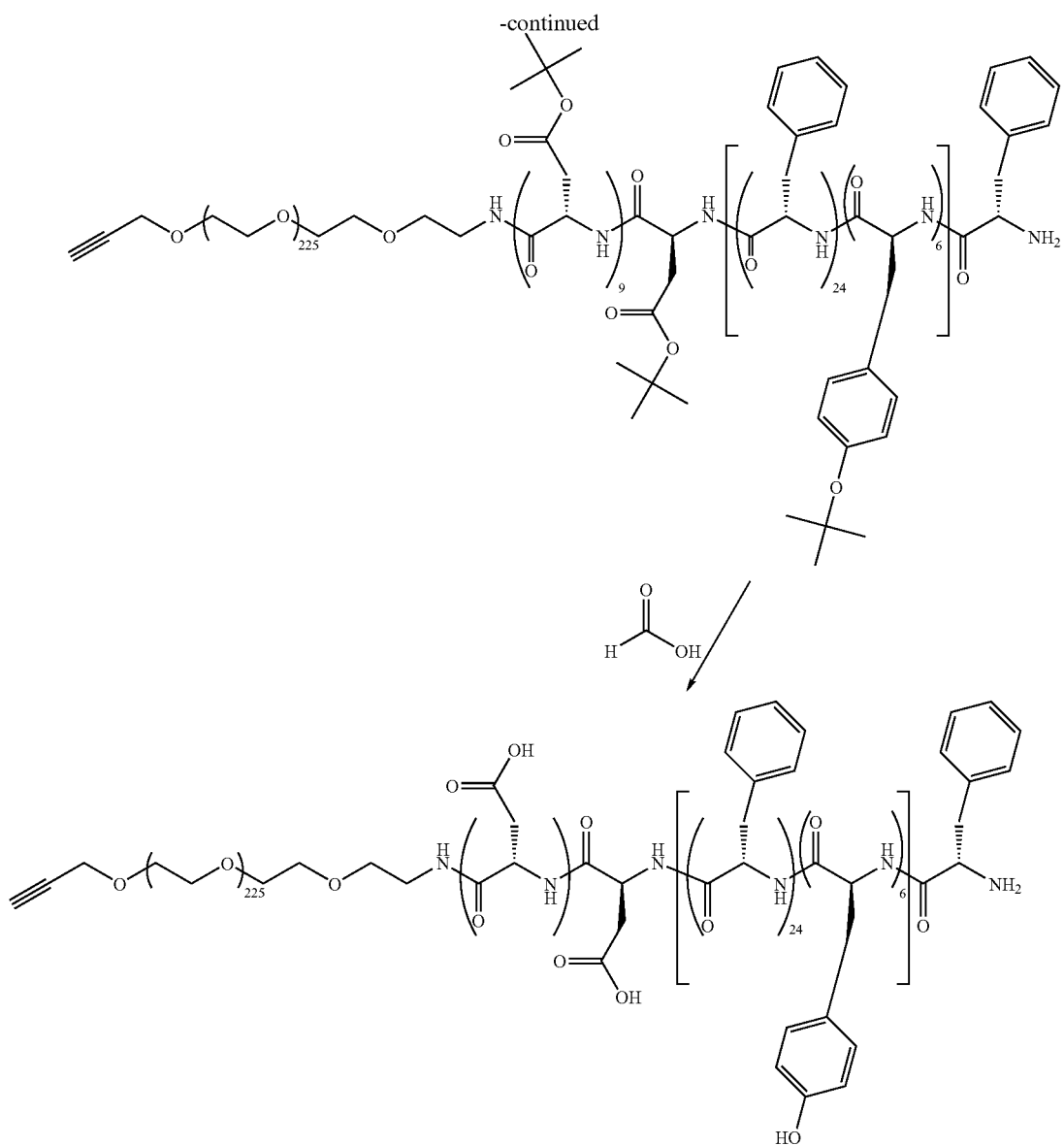

Example 7

Drug Loading and Crosslinking: Experimentally, the loading and crosslinking of drug-filled micelles is carried out by dissolving neutral doxorubicin and the block copolymer in a polar solvent such as ethanol, followed by slow addition to water or buffer solution. Due to the limited solubility of DOX and CPT in water, the drug is forced into the core of the micelle, effectively encapsulating the drug. Crosslinking is achieved by addition of zinc chloride to the micelle solution along with a small amount of sodium bicarbonate to neutralize any hydrochloric acid by-product. In this basic pH environment, the reaction of zinc chloride with the poly(aspartic acid) crosslinking block is rapid and irreversible. The crosslinked nanovectors are isolated using ultrafiltration membranes (Amicon Ultracel YM-30 membranes) and subsequently lyophilized before storage and/or characterization. Unencapsulated drug is removed by the ultrafiltration process, and drug-loading is quantified by dissolving known quantities of the drug-loaded, micelle powder in DMF and quantifying drug concentration by UV-Vis spectroscopy based on a previously determined extinction coefficients ($\epsilon$ for neutral DOX and CPT (DOX absorbance at 485 nm, CPT absorbance at 370 nm).

Drug-loaded, polymer micelles are characterized before and after zinc chloride addition to confirm the effectiveness of crosslinking and to quantify the pH at which micelle dissociation occurs. Fluorescence spectroscopy is an appropriate method to determine drug release from crosslinked polymer micelles in response to environmental changes since the fluorescence of micelle encapsulated DOX and CPT is negligible due to self-quenching in the micelle core but is highly fluorescent in its free form. After reversible crosslinking, qualitative fluorescence experiments are performed to confirm effective crosslinking and stability of drug-loaded micelles. For example, crosslinked micelles are treated with sodium dodecyl sulfate (SDS), a common surfactant known to disrupt uncrosslinked micelles. After treatment with SDS, drug-filled micelles, both crosslinked and uncrosslinked, are evaluated using fluorescence spectroscopy to detect the presence of released DOX (excitation at 485 nm, emission at 590 nm) or CPT (excitation at 370 nm, emission at 432 nm). In the case of uncrosslinked micelles, fluorescence arising from free DOX or CPT in water is be observed due to SDS-induced micelle dissociation.

Example 8

Fluorescence Assay

In another set of experiments, samples of each of crosslinked polymer micelles, uncrosslinked polymer micelles, and free doxorubicin are incubated separately at 37° C. in Dulbecco's Modified Eagle's Medium (DMEM) supplemented with 10% fetal bovine serum (FBS) for 24 hours. This commonly used cell growth medium is used to simulate the ion and pH environment encountered at physiological conditions. The concentration of DOX or CPT in the three samples are adjusted to an equivalent value (e.g. 100 µg/mL) and evaluated for dilution stability using fluorescence spectroscopy. In these experiments, all three samples are diluted to concentrations below the CMC of the polymer micelles (determined using pyrene fluorescence experiments described below). Fluorescence should be observed for the free DOX sample and DOX released from the dissociated, uncrosslinked micelles. If metal-mediated crosslinking is successful, fluorescence from the crosslinked micelles should not be observed, indicating enhanced micelle stability and limited drug release.

Quantitative, acid titration experiments is performed on crosslinked, drug-loaded micelles to determine precise pH values or the pH range at which reversible micelle crosslinking occurs. These titration experiments are carried out by measuring fluorescence (reported in relative fluorescence units) at pH values ranging from ~7.4 (DMEM with serum) to 4.0. The pH of the DOX-loaded, crosslinked micelle solution is adjusted by the incremental addition of lactic acid or hydrochloric acid (HCl) and is measured directly in a stirred, fluorescence cell using a small pH probe (Lazar Ultra-M micro pH electrode). Titration curves are constructed by plotting fluorescence versus solution pH, and the pH at which reversible crosslinking occurs is determined by extrapolation, similar to the pyrene-CMC experiments described in Item D. Utilizing dilution volumes which are below the copolymer CMC values is required since rapid micelle dissociation and drug release, as determined by an increase in quantum yield, are required to quantify pH reversibility. Titration experiments are repeated with crosslinked micelles made with various zinc chloride/block copolymer ratios with the ultimate goal of determining which micellar formulations undergo rapid dissociation at pH 6.8 (solid tumor microenvironment) and pH 5.0-5.5 (endosomal compartments). Fluorescence experiments analyzing the change in quantum yield of the free drug versus pH (control experiment) will also be undertaken to minimize the likelihood of a false positive result. Identical experiments, using encapsulated camptothecin and free CPT, are repeated for successful formulations to determine whether pH-sensitive dissociation and release varies with different encapsulated drugs. We anticipate that reversible crosslinking is independent of the drug utilized, permitting the use of a wide range of hydrophobic drugs. It is understood that carboxylic acid-containing therapeutics may require additional considerations when used in conjunction with zinc-mediated crosslinking.

In addition to fluorescence experiments, light scattering analysis of polymer micelles is performed to determine both micelle size and morphology, which are important to future pharmacokinetic and biodistribution studies. The polymer micelles are analyzed by dynamic and static light scattering experiments at 37° C. in phosphate buffer solution to determine average micelle size (e.g. hydrodynamic radius (Rh)) and micelle size distribution before and after drug loading. The ratio of radius of gyration (Rg), obtained by static light scattering, to Rh offers important information about particle morphology (i.e. spherical micelle, worm-like micelle, vesicle, etc.) before and after crosslinking reactions.

Example 9

In Vitro Studies of Cancer-responsive, Drug-loaded Micelles

In vitro testing of block copolymer micelles and drug-loaded nanovectors provides direct feedback on both the cellular uptake of nanovectors and potential toxicity of the block copolymers, crosslinking reagents, and the by-products of the reversible crosslinking reaction. Utilizing the inherent fluorescence of both doxorubicin and camptothecin as well as other common dyes, cellular uptake is monitored and trafficking of drug-filled and dye-filled nanovectors in cells lines such as MCF-7 (breast cancer), DOX-resistant MCF-7 (breast cancer), HeLa (cervical cancer), HepG2 (liver cancer), and Chinese hamster ovary (control) using confocal laser scanning microscopy. In addition, cell viability studies are performed comparing micelle-encapsulated forms of CPT and DOX to the free drugs in the five cell lines mentioned above.

Cellular Uptake of Nanovectors and Release of Small Molecule Therapeutics in vitro Fluorescence microscopy is a frequently used method to investigate the interactions and intracellular fate of nanoparticulate drug carriers, such as liposomes and micelles, within target cells. To evaluate the uptake and cellular trafficking of cancer-responsive nanovectors, micelles are prepared with encapsulated dyes that fluoresce inside the micelle (Oregon Green or Cy5) and monitored by CLSM. Small amounts of Cy5 are incorporated due to its high quantum yield and its tendency to self-quench at high concentrations in the micelle core. The dye-loaded micelles are evaluated in MCF-7 (ATCC, HTB-22™), DOX-resistant MCF-7 (prepared according to literature protocol), HeLa (ATCC, CCL-2™), HepG2 (ATCC, HB-8065™), and Chinese hamster ovary (ATCC, CCL-61™) cell lines to assay the background rate of uptake of crosslinked micelles by pinocytosis. Unless otherwise stated, HeLa, HepG2, and Chinese hamster ovary cells are grown in DMEM supplemented with 10% fetal bovine serum (FBS). MCF-7 and DOX-resistant MCF-7 cells are grown in Roswell Park Memorial Institute (RPMI) media with 10% heat-inactivated FBS. For confocal studies, cells are incubated in the presence of both non-loaded, crosslinked micelles (to establish any background fluorescence) and dye-filled, crosslinked micelles (dye—1 µg/mL) directly on cover slips to a confluence of 60-70%, incubated with fluorescent nanovectors for 0.5, 1, or 4 hours, and mounted on glass slides using a fluorophore-free mounting medium. In the case of MCF-7 and DOX-resistant MCF-7 cells, the cells are washed three times with PBS pH 7.4 and then fixed to the cover slips with a 1% formaldehyde solution in PBS for 10 minutes prior to mounting on the glass slides. Since both DOX and CPT require cellular entry and cytoplasmic delivery to be of therapeutic value, these basic uptake studies in a variety of cell cultures are an important benchmark in determining their potential clinical usefulness. In general, micelles with diameters of 100 nm or less are taken up by cells, albeit indiscriminately, by pinocytosis. However, recent studies have shown that drug-loaded nanoparticles also undergo rapid exocytosis if endosomal escape is not achieved, and this phenomenon ultimately results in the reduced efficacy of the encapsulated drug. Notwithstanding this phenomenon, these same studies suggest that targeted nanovectors, which undergo uptake by receptor-mediated endocytosis (RME), are more apt to avoid exocytosis and may enter the cell through a different intracellular pathway.[78]

Figure 14:
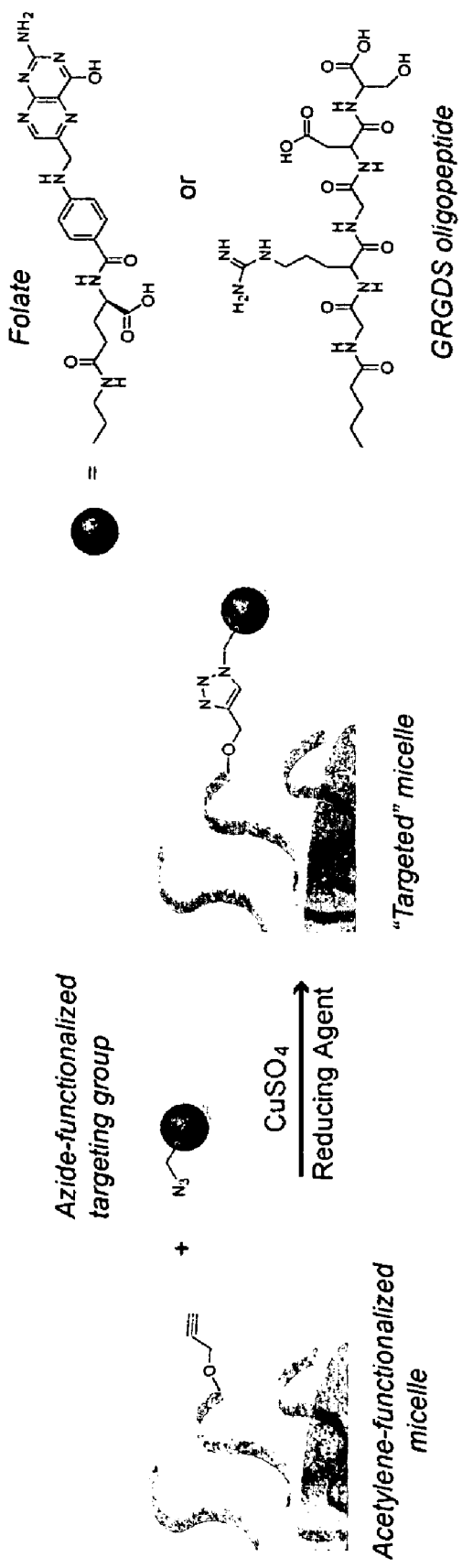
FIG. 14 shows the conjugation of acetylene-functionalized micelles with azide-containing folate or an azide-containing GRGDS oligopeptide by click chemistry.

Preliminary studies involving cell-targeted nanovectors are undertaken to compare micelle uptake by pinocytosis and RME. To accomplish this, acetylene-functionalized micelles are conjugated with azide-containing folate or an azide-containing GRGDS oligopeptide by click chemistry as shown in FIG. 14. Relative to normal cells and tissue, the folate receptor is over-expressed in many epithelial malignancies, such as ovarian, colorectal, and breast cancer and has been identified as a tumor marker. RGD-containing oligopeptides have been shown to bind to $\alpha_v\beta_3$ integrins which are over-expressed on actively proliferating endothelium around cancerous tissue. Both targeting groups have been used extensively in drug delivery systems and have been shown to promote cellular uptake by cancer cells. Cellular uptake and distribution of cell-targeted, dye-filled micelles are evaluated in the five previously described cell lines. Previous studies involving folate-conjugated polymer micelles suggest that receptor-mediated endocytosis is a more efficient method of cellular entry when compared to simple pinocytosis. Micelle formulations which achieve the highest levels of cellular entry, as judged by intracellular fluorescence, are deemed the most promising. Using the click conjugation approach, a range of azide-functional, cell-targeting moieties are attached, making this approach advantageous for quickly evaluating multiple targeting groups in multiple different cell lines.

Cellular uptake experiments using dye-filled or dye-conjugated, crosslinked nanovectors are complemented with other confocal studies involving doxorubicin and camptothecin-filled micelles, which provide a signal indicating both uptake and release. As previously discussed, DOX and CPT are inherently fluorescent, but their quantum yield is significantly reduced in the micelle core due to self quenching. Utilizing this feature, drug distribution analysis of DOX- and CPT-loaded micelles are performed in the five previously described cell lines using confocal microscopy. Each cell line is incubated for 2 to 24 hours with no DOX or CPT (control), free DOX or CPT (1 µM), and drug-loaded micelles (both uncrosslinked and zinc-crosslinked, micelle concentration adjusted to achieve 1 µM DOX and CPT). The nucleus of the cells is stained with Hoechst 33342 (Molecular Probes), and the culture media is replaced with phosphate buffer solution prior to confocal microscopy. DOX and CPT are topoisomerase inhibitors and require access to the nucleus to achieve therapeutic effects. If the drug-loaded micelles are taken up by cells and can escape endosomal compartments, then fluorescence from DOX and CPT should be observed in both the cytoplasm and the nucleus of the cell. Successful micelle formulations will result in high concentrations of the released drugs in the cell nucleus. Special observation is made in experiments involving folate-targeted micelles and non-targeted micelles in DOX-resistant MCF-7 cells. Drug-resistant cancer cells have over-expressed proteins which minimize chemotherapeutic entry (e.g. P-glycoprotein (Pgp) expression) or mechanisms to sequester weakly-basic drugs in acidic organelles (e.g. recycling endosome, lysosome, and trans-Golgi network).

Drug-loaded nanovectors, particularly the folate-targeted micelles, are taken up by the DOX-resistant MCF-7 cells and rendered virtually invisible to cancer cells, offering a potentially effective approach to overcoming multi-drug resistance. Studies using drug-loaded micelles may also answer questions regarding the time-dependant release from the zinc-crosslinked micelles. For example, in comparison with free DOX and CPT, drug release from the crosslinked micelle formulation may be sustained over a much longer time period. Previously reported studies on uncrosslinked, DOX-loaded micelles suggest that similar therapeutic effects are achieved with fewer doses and lower concentrations of micellar DOX.[84]

Example 11

Cytotoxicity Analysis

While the block copolymer components and reagents used in these studies are generally recognized as safe, experiments are conducted to determine their cytotoxic concentration limits, if any, in five cell lines: MCF-7, DOX-resistant MCF-7, HeLa, HepG2, and Chinese hamster ovary. Cell viability tests are performed using a highly sensitive, ATP-based assay (Celltiter-Glo™, Promega) which uses the luciferase reaction to measure the number of viable cells in culture. The reagent is prepared by mixing with an appropriate buffer and then added directly to multi-well plates containing the cells to be tested. After mixing for two minutes, the plates are allowed to equilibrate at room temperature for 10 minutes and then luminescence is measured using a luminometer equipped with a plate reader. This particular method was chosen because it is homogeneous with only a few plate-handling steps, data is collected within minutes after adding the Celltiter-Glo™ reagent, and it is more sensitive than traditional colormetric and fluorometric assays (e.g MTT, alamarBlue, Calcein-AM). In addition to luminescence response due to apoptosis or necrosis, one must consider other variables which may change the cell number to luminescence relationship using this particular assay. These include the use of multi-well plates suitable for luminescence measurements, ATP variations due to cell density, and adequate mixing to ensure lysis and extraction of ATP from cells. Before cytotoxicity measurements are made, each cell line is seeded at ten different densities ranging from 0 to 50,000 cells per well, and the cell viability is tested using the cell viability assay described above. Since a linear relationship exists between luminescence (relative luminescence units) and the number of cells in culture, potential assay problems should be evident by large deviations from the standard, linear relationship. Also, an ATP standard curve, prepared using multi-well plates with varying concentrations of ATP in growth medium and recording luminescence following addition of the Celltiter-Glo™ reagent, are also useful in identifying procedural errors in the assay. In general, a tetrazolium salt MTT cell viability assay, which measures mitochondria function, are used in place of the ATP-based assay.

To ascertain the cytotoxicity of the nanovectors and crosslinking reagents, viability studies comparing various concentrations of the block copolymer micelles (without DOX or CPT) using the five cell lines described previously are performed in triplicate using the previously detailed ATP-based assay. Specifically, each of the five cell lines are grown to 80% confluence and seeded at 7000 cells per well and incubated for 1 day at 37° C. in a humidified atmosphere with 5% $CO_2$. Following incubation, the culture media is replaced with an equal volume of media containing 0 (control), 5, 10, 20, or 40 µg/mL concentration of the multiblock copolymer. It should be noted that all of these concentrations are above the critical micelle concentration (approximately 3 μg/mL), and therefore, the majority of the block copolymer is present in micellar form. Zinc-crosslinked micelles (without DOX or CPT) will also be evaluated in each of the cell lines at similar concentrations as described above. Assays are performed at 1, 3, and 5 days with no media change over the 5 day period, and cell viability is expressed as a percentage relative to samples grown without the block copolymer (control).

Once the biocompatibility of the zinc-crosslinked and uncrosslinked multi-block copolymer micelles has been demonstrated, detailed cell viability studies are performed comparing free DOX and CPT versus their crosslinked and uncrosslinked micellar analogues. MCF-7, DOX-resistant MCF-7, HeLa, HepG2, and Chinese hamster ovary cells are plated into a 96-well plates (7,000 cells/well) and incubated in appropriate media for 1 day. Free DOX and CPT are added to the media in concentrations of 0, 0.001, 0.01, 0.1, 1, and 10 μM, and the cells are incubated for 1, 3, and 5 days without media change. Cell viability assays are performed in triplicate using the Celltiter-Glo™ reagent according the previously described protocol, and the data is averaged and plotted against drug concentration as a best fit sigmoidal curve by using a nonlinear curve-fitting algorithm. $IC_{50}$ values are reported as the drug concentration resulting in 50% cell viability. These experiments are repeated with uncrosslinked micelles, crosslinked micelles, and folate (in MCF-7 cells) or RGD-conjugated, crosslinked micelles (in HepG2 cells). The quantity of multiblock copolymer is adjusted, based on calculated micelle drug-loading values, to achieve comparable drug concentrations of 0, 0.001, 0.01, 0.1, 1, and 10 μM. $IC_{50}$ values are calculated for each sample set to determine which formulation is most efficient in killing cancer cells. Cell viability is monitored over a five day period to ensure that adequate data points are obtained to properly evaluate all micelle formulations. For example, after 24 hours, free DOX might demonstrate enhanced cytotoxicity when compared to a crosslinked, micellar formulation, but over longer time periods (i.e. 5 days), the micelle formulation may prove to be more effective due to slow release from the micelle core.

Hemolysis studies comparing various concentrations of neutral doxorubicin and camptothecin versus drug-loaded micelles, both crosslinked and uncrosslinked, are performed using red blood cells (RBC) isolated from whole human blood. Stock solutions containing isolated RBC in PBS (108 RBC per 200 μL) at pH values of 5.8, 6.6, 7.4 are prepared, and various concentrations of the drugs, polymer micelles, and drug-loaded micelles are incubated at 37° C. for 1 hour in each of the three RBC stock solutions. Following incubation, each RBC solution is subjected to centrifugation, and the hemoglobin release is determined spectrophotometrically at 541 nm. Hemolytic activity of each sample at varying pH values are expressed as a percentage of hemoglobin release relative to a 1% v/v Triton X-100 solution (positive control), which is assumed to give close to 100% hemolysis. Free DOX and CPT are evaluated at concentrations of 0 (negative control), 50, 100, 200, and 400 μg/mL at each of the three pH values. Drug-loaded, multi-block copolymer micelles, both zinc-crosslinked and uncrosslinked, are assayed at pH 5.8, 6.6, and 7.4 and compared to the hemolytic activity of the free drug. The total polymer concentrations are adjusted, depending on known micelle drug loading, to achieve comparable DOX and CPT concentrations of 0, 50, 100, 200, and 400 μg/mL. We anticipate that the hemolytic activity of the micelle-encapsulated drug is dramatically reduced when compared to the free drug. Previous hemolysis studies of DOX-loaded PEG-b-poly(caprolactone) (PCL) showed no hemolytic activity of DOX in micelle form up to 225 μg/mL as compared to significant hemolysis (>10%) observed for the free DOX at similar concentrations.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A drug-loaded micelle comprising a triblock copolymer, wherein said micelle has a drug-loaded inner core, a crosslinked outer core, and a hydrophilic shell, wherein the multiblock copolymer is of formula III:

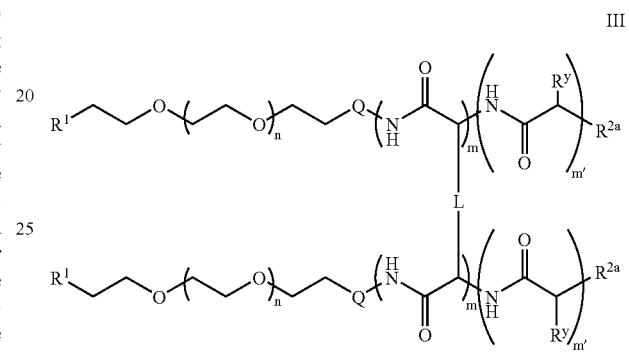

wherein:
  n is 10-2500;
  m is 5-50;
  m' is 5-50;
  L is a metal crosslinked amino acid side-chain group;
  $R^y$ is a hydrophobic or ionic, natural or unnatural amino acid side-chain group;
  $R^1$ is -Z(CH$_2$CH$_2$Y)$_p$(CH$_2$)$_t$R$^3$, wherein:
    Z is —O—;
    Y is —O—;
    p is 0-10;
    t is 0-10; and
    $R^3$ is —N$_3$;
  Q is a valence bond;
  $R^{2a}$ is —NR$^4$C(O)R$^4$; and
  each $R^4$ is independently hydrogen or an optionally substituted aliphatic.

2. The drug-loaded micelle according to claim 1, wherein the metal is zinc.

3. The drug-loaded micelle according to claim 2, wherein the crosslinked amino acid is aspartic acid or glutamic acid.

4. The drug-loaded micelle according to claim 2, wherein the amino acid is histidine.

5. The drug-loaded micelle according to claim 1, wherein said micelle is a mixed micelle.

6. The drug-loaded micelle according to claim 1, wherein $R^1$ is $$N_3\frown O\frown$$

7. The drug-loaded micelle according to claim 1, wherein $R^{2a}$ is selected from the group consisting of:

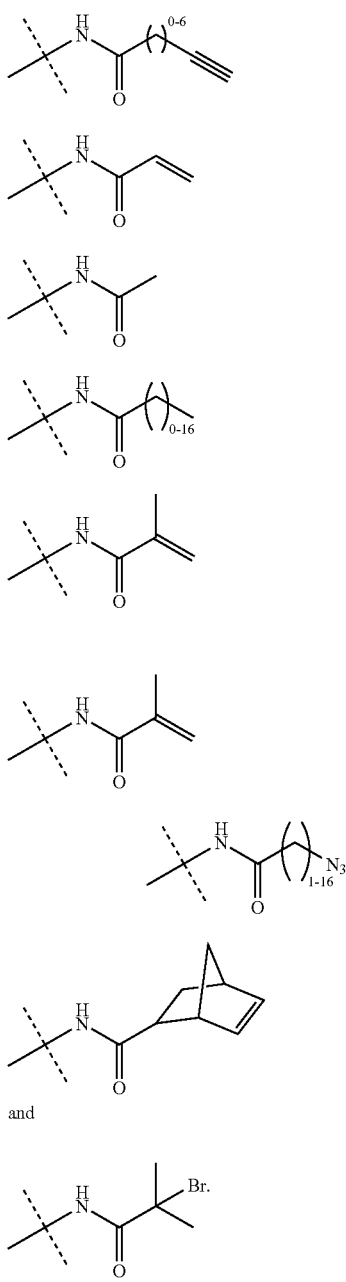

xvi xvii xxiv xxvi xxvii xxvii xxviii xxix and xlvii

8. The drug-loaded micelle according to claim 1, wherein $R^y$ is a hydrophobic amino acid side-chain is a side chain of phenylalanine, alanine benzyl glutamate, alkyl glutamate, benzyl aspartate, alkyl aspartate, leucine, tyrosine, serine, threonine, glutamic acid, aspartic acid, or a combination thereof, wherein the overall amino acid side chain is hydrophobic.

9. The drug-loaded micelle according to claim 8, wherein $R^y$ is a hydrophobic amino acid side-chain selected from a mixture of phenylalanine and tyrosine or a mixture of leucine and tyrosine, such that the overall amino acid side chain is hydrophobic.

10. The drug-loaded micelle according to claim 1, wherein:
n is about 200 to about 300;
m is 5-25;
m' is 10-50; and
$R^{2a}$ is —NHC(O)CH$_3$.

11. The drug-loaded micelle according to claim 1, wherein the micelle encapsulates a hydrophobic chemotherapeutic drug selected from Abarelix, Aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin, Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin acetate, Hydroxyurea, Ibritumomab, Idarubicin, Ifosfamide, Imatinib Mesylate, Interferon alfa-2a, Interferon alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Vairubicin, Vinbiastine, Vincristine, Vinorelbine, Zoledronate, or Zoledronic acid.

12. The drug-loaded micelle according to claim 11, wherein the hydrophobic chemotherapeutic drug is Doxorubicin or Doxorubicin hydrochloride.

13. The drug-loaded micelle according to claim 11, wherein the hydrophobic chemotherapeutic drug is Gemcitabine.

14. The drug-loaded micelle according to claim 11, wherein the hydrophobic chemotherapeutic drug is Letrozole.

\* \* \* \* \*

UNITED STATES PATENT AND TRADEMARK OFFICE
CERTIFICATE OF CORRECTION

PATENT NO. : 7,638,558 B2 Page 1 of 1
APPLICATION NO. : 11/396872
DATED : December 29, 2009
INVENTOR(S) : Breitenkamp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 940 days.

Signed and Sealed this

Ninth Day of November, 2010

David J. Kappos
*Director of the United States Patent and Trademark Office*